(12) United States Patent
Watkins et al.

(10) Patent No.: US 6,774,128 B2
(45) Date of Patent: Aug. 10, 2004

(54) METHODS FOR PREVENTION AND TREATMENT OF GASTROINTESTINAL DISORDERS

(75) Inventors: Crystal C. Watkins, Timonium, MD (US); Solomon H. Snyder, Baltimore, MD (US); Christopher D. Ferris, Franklin, TN (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/840,014

(22) Filed: Apr. 19, 2001

(65) Prior Publication Data

US 2002/0128171 A1 Sep. 12, 2002

Related U.S. Application Data

(60) Provisional application No. 60/198,545, filed on Apr. 19, 2000.

(51) Int. Cl.[7] .............................................. A61K 31/415
(52) U.S. Cl. ....................................... 514/258; 544/262
(58) Field of Search ................................ 514/3, 4, 258; 544/262

(56) References Cited

U.S. PATENT DOCUMENTS

| | | | | |
|---|---|---|---|---|
| 5,856,498 A | * | 1/1999 | Dorziotis et al. ............ | 546/339 |
| 5,859,034 A | * | 1/1999 | Warrellow et al. ........... | 514/357 |
| 5,891,904 A | * | 4/1999 | Stief et al. ................... | 514/423 |
| 6,004,927 A | * | 12/1999 | Benet et al. .................... | 514/9 |
| 6,417,208 B1 | * | 7/2002 | Michaeli ...................... | 514/359 |
| 6,451,813 B1 | * | 9/2002 | Cutler et al. ................. | 514/312 |
| 2002/0012633 A1 | * | 1/2002 | Gmunder et al. ............. | 424/48 |

FOREIGN PATENT DOCUMENTS

EP 656898 B1 * 1/1997

OTHER PUBLICATIONS

Bortolotti et al. Effects of Sildenafil on Esophogeal Motility . . . Gastroenterology. Feb. 2000, vol. 118, No. 2, pp. 253–257.*
Watkins et al. Loss of Neuronal Nitric Oxide Synthase . . . Society For Neuroscience Abstracts. 2000, vol. 30, Part 2, p. 1435, Abstract 537.1.*
Gastroenterology. Apr. 2000, vol. 118, No. 4, Suppl 2, Abstract 3207 (Eherer er al), Abstract 3667 (Watkins et al), and Abstract 4770 (Bortolotti et al).*

* cited by examiner

Primary Examiner—Jeffrey Edwin Russel
(74) Attorney, Agent, or Firm—Foley & Lardner LLP

(57) ABSTRACT

Disclosed are methods for preventing or treating a gastrointestinal (GI) disorder in a mammal such as a human patient. In one embodiment, the methods include administering to the mammal a therapeutically effective amount of a compound that modulates a nitric oxide (NO) signaling pathway, particularly in GI neurons. Methods of the invention are particularly useful for the treatment (including prophylactic treatment) of diabetic gastropathies and other GI disorders.

7 Claims, 11 Drawing Sheets

METHODS FOR PREVENTION AND TREATMENT OF GASTROINTESTINAL DISORDERS

CROSS-REFERENCE TO RELATED APPLICATION

This application claims the benefit of U.S. provisional application No. 60/198,545 filed on Apr. 19, 2000, the disclosure of which application is incorporated herein by reference.

STATEMENT OF U.S. GOVERNMENT SUPPORT

Funding for the present invention was provided in part by the Government of the United States by virtue of Grant No. DA-00266, Research Scientist Award No. DA-00074 and Fellowship No. MH-19547 from the U.S. Public Health Service. Accordingly, the Government of the United States has certain rights in this invention.

BACKGROUND OF THE INVENTION

1. Field of the Invention

The present invention generally relates to methods for preventing or treating gastrointestinal (GI) disorders. In one aspect, the invention provides methods for treating the disorders by modulating nitric oxide (NO) signaling pathways particularly in GI neurons. Methods of the invention typically involve administering at least one compound that modulates the pathway by increasing one or more of NO activity or levels of neuronal nitric oxide synthase (nNOS). The invention has a wide spectrum of useful applications including treating a variety of gastropathies by administering a therapeutic amount of at least one ofinsulin or a phosphodiesterase (PDE) inhibitor such as sildenafil (Viagra™).

2. Background

Hypomotility is one feature of a wide spectrum of gastrointestinal (GI) disorders. For example, gastric hypomotility accompanied by delayed emptying has been described. Stasis impacting the intestine, for example, is also known. See generally McCallum, R. W.(1989) in *Gastrointestinal Disease*, $4^{th}$ ed. (Sleisenger, M. H. and Fordtran, J. S. eds.) W. B. Saunders Co., Philadelphia; and references cited therein.

Symptoms of most GI disorders generally include nausea, vomiting, heartburn, post-prandial discomfort and indigestion. In some instances, acid reflux within the GI tract can cause ulceration leading to internal bleeding and infection. The pain associated with many of the GI disorders can lead to costly and potentially life-threatening misdiagnoses of asthma or myocardial infarction. See Brunton, L. L. in *The Pharmacological Basis of Therapeutics*, $8^{th}$ ed. (Gilman, A. G et al. eds) McGraw-Hill, Inc. New York.

Particular diseases are associated with hypomotility or stasis in the GI tract. For example, diabetic neuropathy, anorexia nervosa, and achlorhydria are frequently accompanied by gastric hypomotility. Damage to the GI tract following surgical intervention, for instance, can result in substantial gastric stasis.

Current treatment of gastric hypomotility generally involves administration of a prokinetic agent, typically domperidone, cisapride, or metoclopramide. It has been reported however that such drugs do not always impact gastric stasis and may be associated with side-effects. See Brunton, L. L., supra.

Diabetes is a common disorder worldwide resulting in significant complications including GI dysfunction. gastrointestinal dysfunction. See Porse, D. and Halter, J. B. (1999) in *Diabetic Neuropathy* (Dyck, P. J. and Thomas, P. K, eds) W. B Saunders Co. Philadelphia, Pa.; and Poster, D. W. (1998) in *Harrison's Principles of Internal Medicine* (A. S. Fauci et al. eds) McGraw-Hill New York.

There have been attempts to study human diabetes by employing animal models. Such models include streptozotocin-induced (STZ-induced) diabetes and rodent mutants such as NOD (non-obese diabetic) mice.

There has been recognition that diabetic gastropathies involve perturbation in the normal relaxation of the pyloric sphincter; an organ that helps coordinate gastric emptying.

The NOS enzyme has attracted much attention. Under appropriate conditions, the enzyme produces nitric oxide (NO). See e.g., U.S. Pat. Nos. 5,439,938; 6,103,872; and 6,168,926 to S. H. Snyder et al. for general disclosure relating to NOS and NO. See also Zakhary, R. et al. (1997) *PNAS (USA)* 94: 14848.

There is almost universal recognition that NO functions as a neurotransmitter. There is emerging evidence that NO provides functions in the GI tract, particularly the intestine, stomach and pylorus. See e.g, Huang, P. L. et al. (1993) *Cell* 75: 1273.

In particular, loss of pyloric nNOS has been associated with gastric outflow obstruction. NO has also been implicated in reducing of isolated pyloric pressure waves, altering distribution of liquid glucose within the stomach, slowing gastric emptying, and reducing stomach tone.

There have been problems establishing firm relationship between NO effects and GI function.

For example, there is belief that NO may inhibit gastric emptying in humans, although in some animal models, nNOS is thought to delay that process. In addition, it has been difficult to establish how nNOS expression is regulated, particularly in vivo. These and other drawbacks have impeded efforts to develop therapies that involve increasing or decreasing endogenous NO levels.

There is general understanding that cyclic guanosine monophosphate (cGMP) is an important cell messenger molecule. Enzymes termed phosphodiesterase (PDE) are primarily responsible for destroying cGMP, typically by catalyzing hydrolytic reaction between the cGMP and water. There have been reports of ten (10) PDE families with each have a distinctive tissue, cellular and subcellular distribution. Some PDE families are thought to prefer cyclic adenosine monophosphate (cAMP) as a substrate instead of cGMP.

Numerous PDE inhibitors have been disclosed. For example, PDE type III and IV inhibitors have been reported. See eg., U.S. Pat. Nos. 4,753,945; 4,837,239; 4,971,972; 5,091,431; 6,054,475; 6,127,363; and 6,156,753; as well as referenced cited therein. See also Komas et al. in *Phosphodiesterase Inhibitors* (1996) (Schudt et al. eds) Academic Press, San Diego, Calif.

Particular attention has focussed on inhibitors of type V PDE, one of the cGMP preferred enzymes. For example, certain of the inhibitors such as sildenafil (Viagra™) have been reported to treat male erectile dysfunction. See e.g, U.S. Pat. Nos. 6,100,270; 6,207,829 and references cited therein.

There has been much work addressing the biological action of insulin. See generally Kahn, C. R. et al in *The Pharmacological Basis of Therapeutics*, $8^{th}$ ed. (Gilman, A. G et al. eds) McGraw-Hill, Inc. New York.

See also U.S. Pat. Nos. 4,916,212; 4,701,440; H245 filed on Jun. 27, 1984; U.S. Pat. Nos. 4,652,547; and 4,652,525 (disclosing a variety of insulin molecules).

It would be useful to have methods for treating gastrointestinal (GI) disorders that involve modulating nitric oxide (NO) signaling. It would be especially desirable to have methods for treating GI disorders that enhance or preferably restore normal NO signaling in the presence of pathological levels of neuronal nitric oxide synthase (nNOS).

SUMMARY OF THE INVENTION

The present invention generally includes methods for preventing or treating gastrointestinal (GI) disorders. In one aspect, the invention provides methods for treating the disorders by modulating nitric oxide (NO) signaling pathways particularly in GI neurons. Preferred invention methods involve administering at least one compound that modulates the pathways by increasing one or more of NO activity or levels of neuronal nitric oxide synthase (nNOS). The invention has a wide spectrum of useful applications including treating a variety of gastropathies by administering a therapeutic amount of at least one of insulin or a phosphodiesterase (PDE) inhibitor such as sildenafil (Viagra™).

We have discovered that by modulating NO signaling pathways in GI neurons it is possible to prevent or treat a wide spectrum of disorders. In particular, it has been found that particular NO signaling pathways are damaged in many mammalian GI disorders. Preferred invention methods generally prevent or treat such disorders by enhancing activity of certain identified molecules in the pathway, typically the NO molecule or the enzyme that facilitates production of that molecule ie., the nNOS enzyme. Preferred invention methods suitably increase and more preferably restore normal neuronal NO signaling, thereby helping to prevent, reduce the severity of, or eliminate symptoms associated with many GI disorders.

More particularly, we have found that many, if not all, GI disorders are associated with abnormal neuronal NO signaling. For example, and as will be discussed below, it is believed that many such disorders involve loss of key NO signaling molecules, particularly nNOS enzyme and the NO molecule. Downstream signaling pathways are thought to suffer from this loss. Without wishing to be bound to theory, that loss of key signaling components is thought to negatively impact a wide variety of cell functions important for normal GI function. That is, the cell functions are removed from significant and normal NO modulation. Loss of that control is believed to facilitate the onset of or aggravate the GI disorders. Increasing or restoring that control is thus a key objective of this invention. Importantly, the invention provides, for the first time, therapeutic methods for preventing or treating the GI disorders by modulating NO signaling pathways. As discussed, preferred invention methods provide at least one of more nNOS enzyme or increasing activity of the NO molecule particularly in GI neurons.

Accordingly, and in one aspect, the invention provides methods for preventing or treating at least one and preferably one gastrointestinal disorder in a mammal suffering from or susceptible to the disorder. In one embodiment, the method includes administering to the mammal a therapeutically effective amount of at least one compound that preferably achieves at least one of:

a) increased nitric oxide (NO) activity e.g. in gastrointestinal neurons or interstitial cells of Cajal as measured in a standard gastric emptying assay (such assay defined herein), or b) provides for increased nitric oxide synthase (nNOS) levels e.g. in the gastrointestinal neurons or the interstitial cells as measured in a standard nNOS protein expression assay (such assay defined herein).

The foregoing general invention method suitably modulates the NO signaling pathway. More particularly, the method provides, for the first time, a way of therapeutically amplifying this important pathway in the presence of abnormal levels of NO or nNOS enzyme. Thus, the method beneficially provides to "at risk" or diseased GI neurons at least one of increased NO activity or increased levels of the nNOS enzyme. This important invention feature desirably increases and preferably restores NO signaling typical of normal GI neurons. Additionally, the methods of the invention may provide supra-physiologic (higher than normal) levels of NO, nNOS, cGMP, etc. which can have important therapeutic benefits, for instance in the treatment of irritable bowel syndrome and other disorders. Without being bound by any theory, by such actions, the GI disorder thus can be prevented or treated by practice of the method.

In some invention embodiments, the recited compound suitably increases both the NO activity and levels of nNOS. However in most embodiments, preferred compounds will increase only one of those characteristics optimally.

In other embodiments, the invention provides for administration of at least two of the compounds discussed above in which a first compound preferably increases the NO activity and a second compound preferably provides for increased levels of the nNOS enzyme. This illustration of the invention is significant because it exemplifies a "two-pronged" approach to increasing NO signaling therapeutically ie., by boosting NO activity with the first compound and increasing nNOS levels with the second compound. This therapeutic strategy may be indicated in settings in which subjects suffer from or are susceptible to especially hard-to-manage or chronic GI disorders. Administration of the first and second compounds can be conducted as needed e.g., at substantially the same time (co-administration of the first and second compounds) or different times to achieve an intended therapeutic outcome.

Preferred methods in accord with the invention employ mammals, preferably a primate, rabbit, or rodent, more preferably a human subject, which mammal has been identified and selected for therapeutic treatment according to the invention. That is, the mammals have been identified and selected to benefit from an increase in at least one of the NO activity or the nNOS level as discussed above. In this instance, at least one of the compounds is then administered to the mammal that has been identified and selected. In embodiments in which administration of two or more compounds is intended, such administration can be simultaneous or at one or more different times as needed to prevent or treat a specific GI disorder.

In other examples of the invention method, the amount of the administered compound is generally sufficient to increase neuronal cyclic guanosine 3'-monophosphate (cGMP) levels suitably as measured by a standard cGMP assay. As discussed above, cGMP is an important molecule "downstream" in relation to NO that is believed to assist signal transmission to the cell. By enhancing the cGMP levels, the invention facilitates such transmission particularly under conditions of less than optimal NO molecule or nNOS enzyme levels. The standard cGMP assay is provided in the discussion and examples that follow.

Therapies of the invention are especially effective for the prevention or treatment of a wide spectrum of GI disorders. Preferred GI disorders are those that can be prevented or treated in accord with this invention, preferably by modulating the NO signaling pathways in neurons associated with the GI tract. Additionally preferred disorders include those characterized by hypomotility or hypermotility in at least one of the small intestine, large intestine, colon, esophagus or stomach. Such preferred GI disorders are further characterized by at least one of the following indications: nausea, vomiting, heartburn, postprandial discomfort, diarrhea, constipation, indigestion or related symptoms.

Further preferred GI disorders in accord with the invention are associated with at least one of diabetes, anorexia nervosa, bulimia, achlorhydria, achalasia, anal fissure, irritable bowel syndrome, intestinal pseudoobstruction, scleroderma, or a related disorder. An example of a particular GI disorder is a gastropathy typically associated with diabetes.

Additionally preferred GI disorders suitably prevented or treated by the invention include more particular intestinal pseudoobstruction, preferably at least one of colonic pseudoobstruction (Ogilvie's syndrome), idopathic gastroparesis, and idiopathic constipation (megacolon).

Still further preferred GI disorders suitably prevents or treated by the invention are those arising from intended or accidental damage to the GI tract eg., stemming from impact or surgical intervention. Other preferred GI disorders in accord with this invention include hypertrophic pyloric stenosis, functional bowel disorder, and gastroesophageal reflux disease (GERD). Preferably, the functional bowel disorder is at least one of irritable bowel syndrome or functional dyspepsia.

The invention also includes methods to treat or prevent (i.e. prophylactic treatment) of Crohn's disease and ulcerative colitis, comprising administering to a patient suffering or susceptible to such disorders an effective amount of one or more PDE inhibitors and/or insulin or biologically active variant thereof.

Practice of the invention is compatible with a wide spectrum of compounds that have capacity to modulate cell signaling pathways. Examples of such compounds include, but are not limited to, phosphodiesterase (PDE) inhibitors. Particular PDE inhibitors in accord with the invention have been previously reported in U.S. Pat. Nos. 6,100,270; 6,006,735; 6,143,757; 6,143,746; 6,140,329; 6,117,881; 6,043,252; 6,001,847; 5,981,527; and 6,207,829 B1; the disclosures of which patents are incorporated herein by reference.

See also PCT/EP95/04065; WO-A-93/06104; WO-A-93/07149; WO-A-93/12095; WO-A-94/00453; EP 0 463756 B1; and WO-A-94/05661.

See also U.S. Pat. Nos. 4,753,945; 5,010,086; 6,121,279; 6,156,753; 6,054,475; 5,091,431; 6,127,363 and 6,040,309.

See also Komas et al., supra (disclosing additional PDE inhibitors suitable for use with the present invention).

Preferred PDE inhibitors for use with the invention include, but are not limited to, particular bicyclic heterocylic PDE inhibitors, more preferably pyrazolo[4,3-d] prymidin-7-ones, pryazolo[3,4-d] pyrimidin4-ones, quinazolin-4-ones, purin-6-ones, pyrido[3,2-d]pyrimidin-4-ones; as well as pharmaceutically acceptable salts thereof.

A specifically preferred pyrazolo[4,3-d]prymidin-7-one is sildenfil (Viagra™) also known as 5-[2-ethoxy-5-(4-methylpiperazin-1-ylsulphonyl)phenyl]-1-methyl-3-n-propyl-1,6-dihydro-7H-pyrazolo[4,3d]pyrimidin-7-one; as well as pharmaceutically acceptable salts thereof.

Additionally preferred compounds in accord with the invention include insulin or biologically active variants thereof including alleleic varients. A preferred insulin is primate, rabbit, or rodent insulin, more preferably human insulin provided in recombinant form. A wide variety of acceptable insulin molecules have been disclosed. Additional preferred compounds for use in accordance with the invention, particularly in a co-administration regime with a PDE inhibitor is one or more compounds that can boost insulin effects or levels (e.g. by enhancing insulin release, or increasing cell sensitivity to insulin or enhancing insulin's actions) of a subject upon administration.

Other aspects of the present invention are described below.

DETAILED DESCRIPTION OF THE INVENTION

Figure 1A:
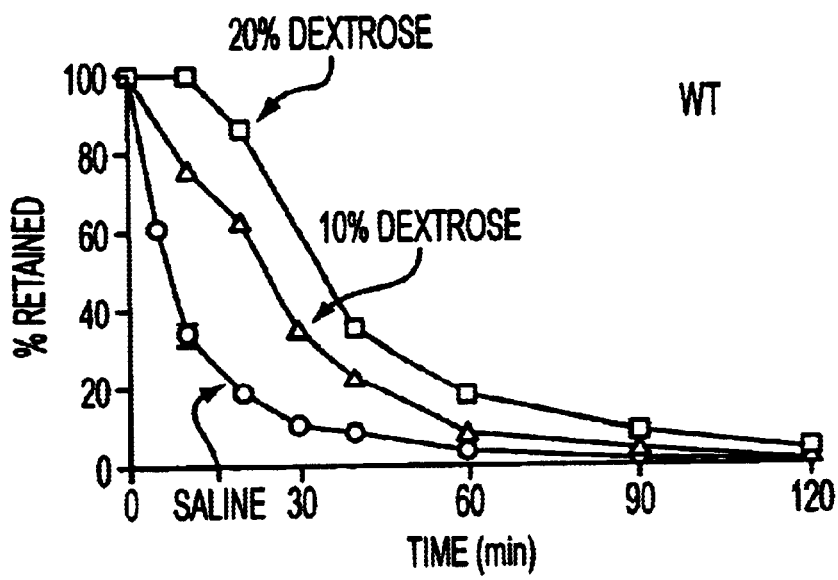
FIGS. 1A–D are graphs showing that nNOS$^{-/-}$ mice have delayed gastric emptying and loss of NO-dependent nonadrenergic, noncholinergic (NANC) relaxation.

As discussed above, the present invention features therapeutic methods for the prevention and treatment of a wide variety of gastrointestinal (GI) disorders modulated by aberrant NO signaling. Such methods generally include administering to a mammal and preferably a human patient in need of such treatment, a therapeutically effective amount of a compound that increases at least one of nitric oxide (NO) activity in gastrointestinal neurons or interstitial cells of Cajal as measured in a standard gastric emptying assay, or provides increased nitric oxide synthase (nNOS) levels in the gastrointestinal neurons or the interstitial cells as measured in a standard nNOS protein expression assay.

Without being bound by theory, methods of the invention can induce, promote or otherwise result in NO being form in neurons and which then diffuses into adjacent muscle where it stimulates the formation of cyclic GMP whose levels are increased by the administered PDE inhibitor compound and/or insulin, insulin variant or other insulin-promoter compound.

Preferred invention compounds include PDE inhibitors such as those impacting types I–V phosphodiesterases. Particularly preferred PDE inhibitors for use in the methods of the invention are disclosed below.

Other preferred compounds include primate, rodent, or rabbit insulin including biologically active variants thereof including allelic variants, more preferably human insulin available in recombinant form. Specifically preferred sources of human insulin include pharmaceutically acceptable and sterile formulations such as those available from Eli Lilly (Indianapolis, Ind. 46285) as Humulin™ (human insulin rDNA origin). See the *The Physician's Desk Reference*, 55th Ed. (2001) Medical Economics, Thomson Healthcare (disclosing other suitable human insulins). Still additional preferred compounds include agents that can boost insulin effects or levels of a subject upon administration, e.g. glipizide and/or rosiglitazone.

As also discussed, it has been discovered that by modulating NO signaling pathways associated with GI neurons, it is possible to prevent or treat a wide spectrum of GI disorders. That is, by providing for enhanced NO signaling in "at risk" or diseased GI neurons, the invention can alter the development or severity of such disorders and related indications. More specifically, it has been found that by increasing levels of the enzyme that provides neuronal NO (nNOS) and/or enhancing neuronal NO function especially when less NO is available to the neurons, it is possible to increase or restore beneficial NO signaling. This and other invention features provides a highly useful therapeutic effect that can prevent or treat one or a variety of GI disorders.

Therapies of the present invention generally include administering a therapeutically effective amount of at least one compound in accord with the invention such as a phosphodiesterase (PDE) inhibitor to a subject in need of such treatment. Illustrative subjects include mammals, particularly primates, rodents and rabbits. A preferred primate is a human subject in need of the therapies provided by this invention.

More typical subjects in accord with the invention include mammals such as human patient suffering from or susceptible to those GI disorders disclosed above, GI disorders preferably by modulating NO signaling pathways operative in GI neurons, especially those typified by hypomotility or hypermotility in at least one of the small intestine, large intestine, colon, esophagus or stomach. Further preferred mammalian subjects include those suffering from or susceptible to those GI disorders characterized by at least one of nausea, vomiting, heartburn, postprandial discomfort, diarrhea, constipation, indigestion or related symptoms.

Further mammalian subjects include those human patients suffering from or susceptible to GI disorders associated with at least one of diabetes, anorexia nervosa, bulimia, achlorhydria, achalasia, anal fissure, irritable bowel syndrome, intestinal pseudoobstruction, scleroderma, or a related disorder. Particular subjects of interest include those suffering from or susceptible to a GI disorder associated with diabetes, especially a diabetic gastropathy.

Additionally preferred subjects include human patients suffering from or susceptible to GI disorders involving intestinal pseudoobstruction, preferably at least one of colonic pseudoobstruction (Ogilvie's syndrome), idiopathic gastroparesis, and idiopathic constipation (megacolon). As discussed above, the invention also includes treatment and prophylaxis of Crohn's disease and ulcerative colitis.

Still further preferred subjects in accord with the invention are human patient suffering from or susceptible to GI disorders relating to damage to the GI tract stemming from impact or surgical intervention, for example. Other preferred subjects suffer from or may be susceptible to GI disorders include hypertrophic pyloric stenosis, functional bowel disorder, and gastroesophageal reflux disease (GERD). Subjects also may be treated that suffer from or are susceptible to Barrett's metaplasia or Barrett's esophagus, which can be a complication of GERD. Preferably, the functional bowel disorder is at least one of irritable bowel syndrome or functional dyspepsia.

A subject is "susceptible to" a GI disorder or other disease or disorder to be treated in accordance with the invention if that subject has a pre-disposition to develop that disorder e.g., a genetic predisposition or pre-disposition impacted by medical history or planned therapeutic intervention such as, but not limited to, abdominal surgery.

As discussed, the invention is fully compatible with use of a wide spectrum of administered compounds including those impacting PDE. Simple testing e.g., by employing a standard in vivo and in vitro assays defined herein, can readily identify suitable compounds. In particular, suitable compounds can be identified through use of the in vivo gastric emptying assay discussed below in the examples which assay includes at least one and preferably all of the following steps a) through e): a) orally administering a detectably-labeled solution into the stomach of a living mouse, for example, a mouse having a nNOS$^{-/-}$ genotype; b) incubating the mouse with the administered solution for a time period of between from about 0 to about 4 hours; c) excising the stomach from the mouse; d) homogenizing the stomach; and e) measuring the amount of the detectably-labeled solution remaining in the stomach homogenate. References herein to a "standard in vivo gastric emptying assay" or "standard gastric emptying assay" or other similar term designate a protocol that includes those steps a) through e).

A preferred solution for use with the in vivo gastric emptying assay is a combination of dissolved sugar such as dextrose and phenol-red although other detectably-labeled solutions may also be used. Preferably, the candidate therapeutic compound is added before or during step a) of the method, usually between from about 1 minute to about one hour before performing step a). A suitable control is a saline or dissolved sugar solution without the compound to be tested.

The foregoing standard in vivo gastric emptying assay is readily adapted to test for other compounds including those that increase nitric oxide synthase (nNOS) levels in the gastrointestinal neurons or the interstitial cells of Cajal. For example, the method can be employed with NOD-diabetic mice in place of the mouse having the nNOS$^{-/-}$ genotype. As discussed below, the NOD mouse is understood to be genetically pre-disposed to develop diabetes. Alternatively, the method is appropriate for use with a mouse previously manipulated to incur diabetes eg., by administration of a toxic sugar such as streptozoticin (STZ). In these particular examples of the in vivo gastric empting assay, subject mice are prepared and gastric contents quantified along lines just discussed and in the examples section. Choice of a particular mouse type to use will be guided by understood parameters such as the type of compound for which screening is desired. See also the example below for more specific disclosure relating to the foregoing standard in vivo gastric emptying assay.

Preferred compounds for use with the therapeutic methods of the invention induce at least about a 10% increase in gastric emptying relative to the gastric emptying achieved in absence of the tested compound in such a standard in vivo gastric emptying assay, more preferably at least about a 15% or 20% increase in gastric emptying relative to a control, and still more preferably induce at least about 25%, 30%, 40%, 50%, 60%, 70%, 80%, 90% or about a 100% increase in gastric emptying relative to absence of the tested compound in a standard in vivo gastric emptying assay.

More particular inhibitor compounds exhibit a half time (t½, the time required to empty about 50% of the detectably-labeled solution) of between from about 1 minute to about one hour, preferably between from about 10 minutes to about 45 minutes, more preferably about 15 to about 30 minutes in the standard in vivo gastric emptying assay.

Additionally preferred compounds of the invention provide for increased nNOS levels in GI neurons and the interstitial cells of Cajal as measured in a standard in vitro nNOS protein expression assay. Suitable compounds can be identified by use of the expression assay as disclosed in the examples following and which includes the following steps a) through e): a) removing GI tissue from a mammalian subject, eg., NOD-diabetic mouse, b) homogenizing the tissue and separating the homogenate by SDS-PAGE gel electrophoresis, c) transferring the fractionated homogenate to an acceptable membrane such as PVDF, d) contacting the membrane with a suitable anti-nNOS antibody, and e) detecting the complex formed between the anti-nNOS antibody and the fractioned homogenate preferably by employing conventional Western blot procedures. The signal from such blots can be detected and quantified using standard densitometric analysis techniques. References herein to a "standard in vitro nNos protein expression assay" or "standard nNOS expression assay" or other similar term designates a protocol that includes those steps a) through e) immediately above.

In such a standard in vitro nNos protein expression assay, the candidate therapeutic compound is added before or during step a) of the method, usually between from about 1 minute to about 2 weeks before performing step a), more preferably about 8 hours to about a week before conducted that step. A suitable control is a saline or dissolved sugar solution without the compound. If desired, the subject mammal can be treated with a conventional NOS inhibitor such as 7-nitroindazole prior to step a), usually between from about 1 minute to about one to two days before performing that step.

Preferred compounds for use with the therapeutic methods of the invention induce at least about a 10% increase in nNOS protein expression relative to the nNOS protein produced in the absence of the tested compound in such a standard in vitro nNOS expression assay, more preferably at least about a 15% or 25% increase in nNOS protein expression relative to a control, and still more preferably induce at least about 25%, 30%, 40%, 50%, 60%, 70%, 80%, 90% or about a 100% increase in nNOS protein expression relative to absence of the tested compound in such a standard in vitro nNOS protein expression assay.

Still further preferred compounds in accord with this invention are sufficient to increase neuronal cyclic guanosine 3'-monophosphate (cGMP) in the neurons as measured by any one of the standard in vitro cGMP assays known in the field. Such assays have been reported in *The Handb. Exp. Pharmacol.* (1983) 58: entitled "Cyclic Nucleotides", Pt. I: Biochemistry, J. A Nathanson, J. W. Kobabian, Eds. (Springer-Verlag, New York), the disclosure of which is incorporated herein by reference.

A preferred cGMP assay for use in accordance with the invention is a radioimmunoassay that monitors cGMP levels in cells and tissues. Such radioimmunoassay are commercially available such as from Amersham Pharmacia Biotech. That amersham assay utlizies a scintillation proximity assay and is further described in Amersham product literature. As referred to herein, a "cGMP assay" or other similar term means an assay as conducted with such an Amersham Pharmacia commercially available radioimmunoassay kit.

Preferred compounds for use with the therapeutic methods of the invention induce at least about a 5% increase in cGMP relative to the cGMP produced in the absence of the tested compound in such a standard in vitro cGMP assay, more preferably at least about a 10% or 20% increase in cGMP relative to a control, and still more preferably induce at least about 25%, 30%, 40%, 50%, 60%, 70%, 80%, 90% or about a 100% increase in cGMP relative to absence of the tested compound in such an assay.

Additionally preferred compounds in accord with the invention will exhibit an $ID_{50}$ of between from about 0.01 to about 10 mM, preferably about 0.1 to about 1 mM, more preferably about 0.5 mM or less in any one of the in vitro test methods for determining cGMP PDE or PDE5 inhibitory action as described in U.S. Pat. No. 6,100,270; WO-A-93/06104; WO-A-93/07149; WO-A-93/12095; WO-A-94/00453; and WO-A-94/05661.

More specific invention embodiments include preventing or treating a gastrointestinal disorder in a mammal suffering from or susceptible to the disorder. In one example, the method includes administering to the mammal a therapeutically effective amount of at least one of:

a) a phosphodiesterase (PDE) inhibitor in an amount sufficient augment nitric oxide (NO) in gastrointestinal neurons as measured in a gastric emptying assay, or b) insulin or a biologically active variant thereof, and/or an agent that can boost insulin effects or levels (e.g. by enhancing insulin release, or increasing cell sensitivity to insulin or enhancing insulin's actions) of a subject upon administration, in an amount sufficient to provide increased nitric oxide synthase (nNOS) levels in the gastrointestinal neurons or interstitial cells as measured in a standard nNOS protein expression assay.

Preferably, the PDE inhibitor decreases activity of a cyclic guanosine monophosphate (cGMP) specific PDE as determined by at least one of the standard PDE or PDE5 assay described herein. In some embodiments it will be useful to decrease activity of the type 5 PDE (PDE5) specifically. However in other embodiments, inhibition of the types I–IV enzymes, with or without inhibition of PDE5, may be more desirable to prevent or treat particular GI indications.

Also preferably, the PDE inhibitor has an $IC_{50}$ of at about 0.5 mM or less in the standard PDE or PDE5 assay. Such preferred PDE inhibitors will also desirably increase neuronal cyclic guanosine 3'-monophosphate (cGMP) in the neurons as measured by a standard cGMP assay.

The insulin agent, i.e. insulin, biologically active variant thereof, or agent that can enhance the effect or levels of insulin levels upon administration, may be a variety of therapeutics. Preferred biologically active variants of insulin are discussed below. Suitable agents that enhance insulin effects or levels include e.g. sulfonylureas such as glipizide, and thiazlidinediones such as rosiglitazone. PPAR-gamma receptors agonists in addition to thiazolidinediones also will be suitable. Suitable agents that can enhance insulin effects and insulin levels also are disclosed in e.g. U.S. Pat. Nos. 5,489,602; 5,811,439; 5,965,589; and 5,972,973. Methods for identifying additional agents that enhance insulin effects and insulin levels are disclosed in U.S. Pat. Nos. 5,466,610 and 6,100.047.

Also particularly preferred are various bioactive forms, particularly oral forms, of insulin that can be administered to a patient in accordance with the invention, particularly to increase nNos expression.

Preferred treatment methods particularly include administration of at least one e.g, about 1 to about, preferably about 2 to about 5, more preferably about one of compounds disclosed herein.

In addition to the above discussed PDE inhibitor compounds, suitable PDE inhibitor compounds for use in the methods of the invention are disclosed below, include compounds of the following Formulae I to XIII, which are generally preferred for use with the present invention. It should be appreciated however that the present invention is not limited by any particular PDE inhibitor compound, and the invention is applicable to any such PDE inhibitor compound now known or subsequently discovered or developed.

More specifically, in one invention embodiment, at least one of the administered compounds is a bicyclic heterocyclic PDE inhibitor such as as described in the U.S. Pat. No. 6,100,270, preferably at least one of the following pyrazolo[4,3-d]prymidin-7-ones, pryazolo[3,4-d]pyrimidin4-ones, a quinazolin-4-ones, a purin-6-ones, or pyrido[3,2-d]pyrimidin-4-ones set forth in the following Formulae I–V including pharmaceutically acceptable salts thereof.

Suitable PDE inhibitor compounds include those of the following Formula I:

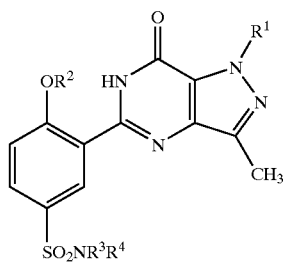

(I)

wherein in Formula I, $R^1$ is methyl or ethyl; $R^2$ is ethyl or n-propyl;

and $R^3$ and $R^4$ are each independently H, or $C_1$–$C_6$ alkyl optionally substituted with $C_5$–$C_7$ cycloalkyl or with morpholino; and pharmaceutically acceptable salts thereof.

Suitable PDE inhibitor compounds also include those of the following Formula II:

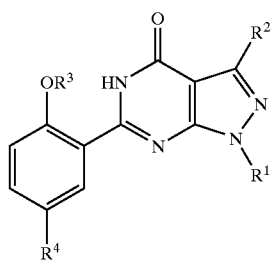

(II)

wherein in Formula II, $R^1$ is $C_1$–$C_6$ alkyl; $R^2$ is H, methyl or ethyl;

$R^3$ is $C_2$–$C_4$ alkyl;

$R^4$ is H; $C_1$–$C_4$ alkyl optionally substituted with $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; $SO_2NR^5R^6$; $CONR^5R^6$; $CO_2R^7$ or halo;

$R^5$ and $R^6$ are each independently H or $C_1$–$C_4$ alkyl; or, together with the nitrogen atom to which they are attached, form a pyrrolidino, piperidino, morpholino, 4-($NR^8$)-1-piperazinyl or 1-imidazolyl group wherein said group is optionally substituted with one or two $C_1$–$C_4$ alkyl groups;

$R^7$ is H or $C_1$–$C_4$ alkyl;

and $R^8$ is H; $C_1$–$C_3$ alkyl or (hydroxy)$C_2$–$C_3$ alkyl; and pharmaceutically acceptable salts thereof.

Additional suitable PDE inhibitor compounds include those of the following Formula (III):

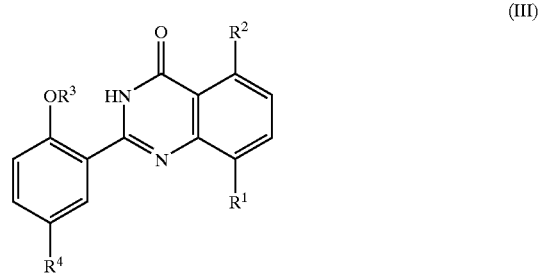

(III)

wherein in Formula III $R^1$ is H; $C_1$–$C_4$ alkyl; $C_1$–$C_4$ alkoxy or $CONR^5R^6$;

$R^2$ is H or $C_1$–$C_4$ alkyl;

$R^3$ is $C_2$–$C_4$ alkyl;

$R^4$ is H; $C_2$–$C_4$ alkanoyl optionally substituted with $NR^7R^8$; (hydroxy)$C_2$–$C_4$ alkyl optionally substituted with $NR^7R^8$; $CH=CHCO_2R^9$; $CH=CHCONR^7R^8$; $CH_2CH_2CO_2R^9$; $CH_2CH_2CONR^7R^8$; $SO_2NR^7R^8$; $SO_2NH(CH_2)_nNR^7R^8$ or imidazolyl;

$R^5$ and $R^6$ are each independently H or $C_1$–$C_4$ alkyl;

$R^7$ and $R^8$ are each independently H or $C_1$–$C_4$ alkyl; or, together with the nitrogen atom to which they are attached, form a pyrrolidino, piperidino, morpholino or 4-($NR^{10}$)-1-piperazinyl group wherein any of said groups is optionally substituted with $CONR^5R^6$;

$R^9$ is H or $C^1$–$C_4$ alkyl;

$R^{10}$ is H; $C_1$–$C_3$ alkyl or (hydroxy)$C_2$–$C_3$ alkyl;

and n is n2, 3 or 4;

with the proviso that $R^4$ is not H when $R^1$ is H, $C_1$–$C_4$ alkyl or $C_1$–$C_4$ alkoxy; and pharmaceutically acceptable salts thereof.

Suitable PDE inhibitor compounds include those of the following Formula IV:

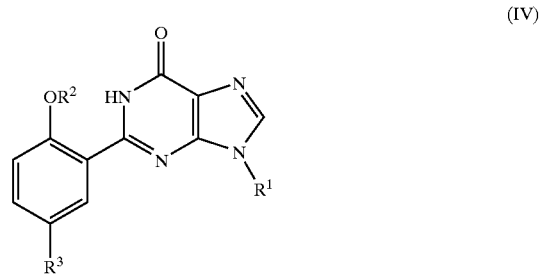

(IV)

wherein $R^1$ is $C_1$–$C_4$ alkyl; $R^2$ is $C_2$–$C_4$ alkyl;

$R^3$ is H or $SO_2NR^4R^5$;

$R^4$ and $R^5$ together with the nitrogen atom to which they are attached form a pyrrolidino, piperidino, morpholino or 4-($NR^6$)-1-piperazinyl group;

and $R^6$ is H or $C_1$–$C_3$ alkyl; and pharmaceutically acceptable salts thereof.

Additional suitable PDE inhibitor compounds include those of the following Formula (V):

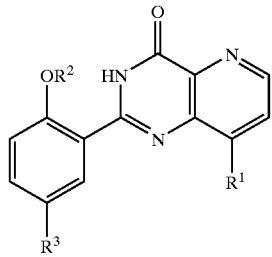

(V)

wherein in Formula V $R^1$ is H; $C_1$–$C_4$ alkyl; CN or $CONR^4R^5$; $R^2$ is $C_2$–$C_4$ alkyl;

$R^3$ is $SO_2NR^6R^7$; $NO_2$; $NH_2$; $NHCOR^8$; $NHSO_2R^8$ or $N(SO_2R^8)_2$;

$R^4$ and $R^5$ are each independently selected from H and $C_1$–$C_4$ alkyl;

$R^6$ and $R^7$ are each independently selected from H and $C_1$–$C_4$ alkyl optionally substituted with $CO_2R^9$, OH, pyridyl, 5-isoxazolin-3-onyl, morpholino or 1-imidazolidin-2-onyl; or, together with the nitrogen atom to which they are attached, form a pyrrolidino, piperidino, morpholino, 1-pyrazolyl or 4-($NR^{10}$)-1-piperazinyl group wherein any of said groups may optionally be substituted with one or two substituents selected from $C_1$–$C_4$ alkyl, $CO_2R^9$, $NH_2$ and OH;

$R^8$ is $C_1$–$C_4$ alkyl or pyridyl;

$R^9$ is H or $C_1$–$C_4$ alkyl;

and $R^{10}$ is H; $C_1$–$C_4$ alkyl or (hydroxy)$C_2$–$C_3$ alkyl; and a pharmaceutically acceptable salt thereof A preferred group of compounds of Formula I above include those wherein:

$R^3$ is H; methyl or ethyl;

$R^4$ is $C_1$–$C_6$ alkyl optionally substituted with cyclohexyl or with morpholino; and $R^1$ and $R^2$ are as previously defined for formula (I), and pharmaceutically acceptable salts thereof.

Preferred compounds of Formula II above include those wherein $R^1$ is n-propyl; $R^2$ is H or methyl; $R^3$ is ethyl or n-propyl; $R^4$ is H; ethyl substituted with $CONR^5R^6$ or $CO_2R^7$; vinyl substituted with $CONR^5R^6$ or $CO_2R^7$; acetyl substituted with $NR^5R^6$; $SO_2NR^5R^6$; $CONR^5R^6$; $CO_2R^7$ or bromo; $R^5$ and $R^6$ together with the nitrogen atom to which they are attached form a morpholino, 4-($NR^8$)-1-piperazinyl or 2,4-dimethyl-1-imidazolyl group; $R^7$ is H or t-butyl; and $R^8$ is methyl or 2-hydroxyethyl; and pharmaceutically acceptable salts thereof.

Preferred compounds of Formula III above include those where $R^1$ is H; methyl; methoxy or $CONR^5R^6$; $R^2$ is H or methyl; $R^3$ is ethyl or n-propyl; $R^4$ is H; acetyl optionally substituted with $NR^7R^8$; hydroxyethyl substituted with $NR^7R^8$; CH=$CHCO_2R^9$; CH=$CHCONR^7R^8$; $CH_2CH_2CO_2R^9$; $SO_2NR^7R^8$; $SO_2NH(CH_2)_3NR^7R^8$ or 1-imidazolyl; $R^5$ and $R^6$ are each independently H or ethyl; $R^7$ and $R^8$ together with the nitrogen atom to which they are attached form a piperidino, 4-carbamoylpiperidino, morpholino or 4-($NR^{10}$)-1-piperazinyl group; $R^9$ is H or t-butyl; and $R^{10}$ is H; methyl or 2-hydroxyethyl; with the proviso that $R^4$ is not H when $R^1$ is H, methyl or methoxy; and pharmaceutically acceptable salts thereof.

Preferred compounds of Formula IV above include those wherein $R^1$ and $R^2$ are each independently ethyl or n-propyl; $R^4$ and $R^5$ together with the nitrogen atom to which they are attached form a 4-($NR^6$)-1-piperazinyl group; and $R^3$ and $R^6$ are as previously defined for Formula IV; and pharmaceutically acceptable salts thereof.

Preferred compounds of Formula V above include compounds wherein $R^1$ is H; n-propyl; CN or $CONH_2$; $R^2$ is ethyl; $R^3$ is $SO_2NR^6R^7$; $NO_2$; $NH_2$; $NHCOCH(CH_3)_2$; $NHSO_2CH(CH_3)_2$; $NHSO_2$(3-pyridyl) or $N[SO_2$(3-pyridyl)]$_2$; $R^6$ is H; methyl or 2-hydroxyethyl; $R^7$ is methyl optionally substituted with 2-pyridyl or 5-isoxazolin-3-onyl; or ethyl 2-substituted with OH, $CO_2CH_2CH_3$, morpholino or 1-imidazolidin-2-onyl; or $R^6$ and $R^7$ together with the nitrogen atom to which they are attached form a (4-$CO_2R^9$)piperidino, 5-amino-3-hydroxy-1-pyrazolyl or 4-($NR^{10}$)-1-piperazinyl group; $R^9$ is H or ethyl; and $R^{10}$ is H; methyl or 2-hydroxyethyl.

A particularly preferred group of compounds is that of Formula III above wherein $R^1$ is methyl; $CONH_2$ or $CONHCH_2CH_3$; $R^2$ is H; $R^3$ is ethyl or n-propyl; $R^4$ is H; acetyl; 1-hydroxy-2-($NR^7R^8$)ethyl; CH=$CHCO_2C(CH_3)_3$; CH=$CHCONR^7R^8$; $SO_2NR^7R^8$ or 1-imidazolyl, $R^7$ and $R^8$ together with the nitrogen atom to which they are attached form a 4-($NR^{10}$)-1-piperazinyl group; and $R^{10}$ is methyl or 2-hydroxyethyl; with the proviso that $R^4$ is not H when $R^1$ is methyl; of formula (IV) wherein $R^1$ is n-propyl; $R^2$ is ethyl; and $R^3$ is 1-piperazinylsulphonyl or 4-methyl-1-piperazinylsulphonyl; and of formula (V) wherein $R^1$ is n-propyl or CN; $R^2$ is ethyl; $R^3$ is $SO_2NR^6R^7$; $NHSO_2CH(CH_3)_2$; $NHSO_2$(3-pyridyl) or $N[SO_2$(3-pyridyl)]$_2$; $R^6$ is H or methyl; $R^7$ is methyl; or ethyl 2-substituted with $CO_2CH_2CH_3$; morpholino or 1-imidazolidin-2-onyl; or $R^6$ and $R^7$ together with the nitrogen atom to which they are attached form a (4-$CO_2R^9$)piperidino or 4-($NR^{10}$)-1-piperazinyl group; $R^9$ is H or ethyl; and $R^{10}$ is H; methyl or 2-hydroxyethyl.

Especially preferred individual compounds of the invention include:

1-ethyl-5-[5-(n-hexylsulphamoyl)-2-n-propoxy-phenyl]-3-methyl-1,6-dihydro-7 H-pyrazolo[4,3-d]pyrimidin-7-one;

1-ethyl-5-(5-diethylsulphamoyl-2-n-propoxy-phenyl)-3-methyl-1,6-dihydro-7H-pyrazolo[4,3-d]-pyrimidin-7-one;

5-[5-(N-cyclohexylmethyl-N-methylsulphamoyl)-2-n-propoxyphenyl]-1-ethyl-3-m ethyl-1,6-dihydro-7H-pyrazolo[4,3-d]pyrimidin-7-one;

6-(5-bromo-2-n-propoxyphenyl)-3-methyl-1-n-propyl-1,5-dihydro-4H-pyrazolo[3,4-d]pyrimidin-4-one;

3-methyl-6-(5-morpholinosulphonyl-2-n-propoxyphenyl)-1-n-propyl-1,5-dihydro-4H-pyrazolo[3,4-d]pyrimidin-4-one;

6-[5-(2-carboxyvinyl)-2-n-propoxzphenyl]-3-methyl-1-n-propyl-1,5-dihydro-4H-pyrazolo[3,4-d]pyrimidin-4-one;

6-[5-(2-t-butoxycarbonylvinvy)-2-n-propoxyphenyl]-3-methyl-1-n-propyl-1,5-dihydro-4H-pyrazolo[3,4-d]pyrimidin-4-one;

3-methyl-6-[5-(2-morpholinocarbonylvinyl)-2-n-propoxyphenyl]-1-n-propyl-1,5-dihydro-4H-pyrazolo[3,4-d]pyrimidin-4-one;

3-methyl-6-[5-(2-morpholinocarbonylethyl)-2-n-propoxyphenyl]-1-n-propyl-1,5-dihydro-4H-pyrazolo[3,4-d]pyrimidin-4-one;

2-{2-ethoxy-5-[4-(2-hydroxyethyl)-1-piperazinyl-sulphonyl]phenyl}-8-methylquinazolin-4-(3H)-one;

2-{5-[4-(2-hydroxyethyl)-1-piperazinylsulphonyl]-2-n-propoxyphenyl}-8-methylquinazolin-4(3H)-one;

8-methyl-2-{5-[2-(4-methyl-1-piperazinylcarbonyl)-ethenyl]-2-n-propoxyphenyl}quinazolin-4(3H)-one;

8-carbamoyl-2-{2-ethoxy-5-[4-(2-hydroxyethyl)-1-piperazinylsulphonyl]phenyl}quinazolin-4(3H)-one;

8-ethylcarbamoyl-2-(2-n-propoxyphenyl)quinazolin-4(3H)-one;

2-[2-ethoxy-5-(4-ethoxycarbonylpiperidino-sulphonyl)phenyl]-8-n-propylpyrido[3,2-d]pyrimidin-4(3H)-one;

2-[5-(4-carboxypiperidinosulphonyl)-2-ethoxyphenyl]-8-n-propylpyrido[3,2-d]pyrimidin-4(3H)-one;

2-{2-ethoxy-5-[4-(2-hydroxyethyl)-1-piperazinylsulphonyl]phenyl}-8-n-propylpyrido[3,2-d]pyrimidin-4(3H)-one;

and 2-{2-ethoxy-5-[(bis-3-pyridylsulphonyl)amino]-phenyl}-8-n-propylpyrido[3,2-d]pyrimidin-4(3H)-one.

In another invention embodiment, at least one of the administered compounds is a tetracyclic cGMP specific PDE inhibitor such as those described in U.S. Pat. No. 6,143,746 and as set forth in the following Formulae VI–IX including pharmaceutically acceptable salts thereof.

Mores specifically, suitable compounds include those of the following Formula VI:

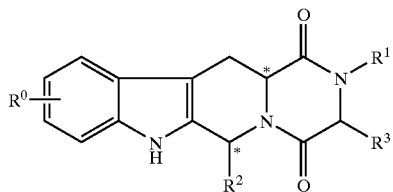

(VI)

wherein in Formula VI $R^0$ represents hydrogen, halogen, or $C_{1-6}$ alkyl;

$R^1$ represents hydrogen, $C_{1-6}$ alkyl, $C_{2-6}$ alkenyl, $C_{2-6}$ alkynyl, haloC$_{1-6}$ alkyl, $C_{3-8}$ cycloalkyl, $C_{3-8}$ cycloalkylC$_{1-3}$alkyl, arylC$_{1-3}$ alkyl, or heteroarylC$_{1-3}$ alkyl;

$R^2$ represents an optionally substituted monocyclic aromatic ring selected from benzene, thiophene, furan, and pyridine, or an optionally substituted bicyclic ring;

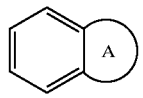

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur, and nitrogen; and $R^3$ represents hydrogen or $C_{1-3}$ alkyl, or $R^1$ and $R^3$ together represent a 3- or 4-membered alkyl or alkenyl chain; and pharmaceutically acceptable salts and solvates thereof. Examples of solvates include hydrates.

Suitable compounds also include those of the following Formula VII:

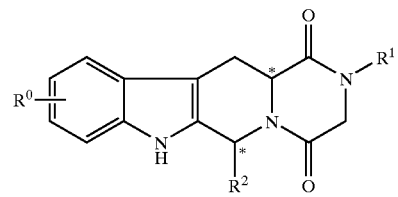

(VII)

wherein in Formula VII $R^0$ represents hydrogen, halogen, or $C_{1-6}$ alkyl;

$R^1$ represents hydrogen, $C_{1-6}$ alkyl, haloC$_{1-6}$ alkyl, $C_{3-8}$ cycloalkyl, arylC$_{1-3}$ alkyl, or heteroarylC$_{1-3}$ alkyl;

$R^2$ represents an optionally substituted monocyclic aromatic ring selected from benzene, thiophene, furan, and pyridine, or an optionally substituted bicyclic ring

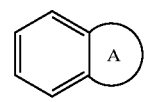

attached to the rest of the molecule via one of the benzene ring carbon atoms, and wherein the fused ring A is a 5- or 6-membered ring which can be saturated or partially or fully unsaturated and comprises carbon atoms and optionally one or two heteroatoms selected from oxygen, sulphur, and nitrogen; and pharmaceutically acceptable salts and solvates thereof. Examples of solvates include hydrates.

A further subgroup of compounds of Formula VI preferred for use in the methods of the invention, are compounds of the following Formula VIII:

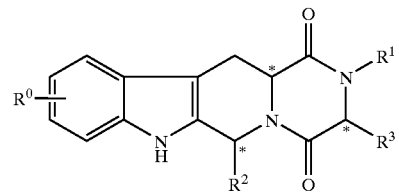

(VIII)

wherein in Formula VIII:

$R^0$ represents hydrogen, halogen, or $C_{1-6}$ alkyl;

$R^1$ represents hydrogen or $C_{1-6}$ alkyl;

$R^2$ represents the bicyclic ring

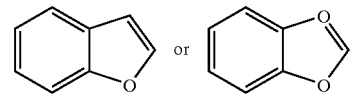

which can be optionally substituted by one or more groups selected from halogen and $C_{1-3}$ alkyl; and $R^3$ represents hydrogen or $C_{1-3}$ alkyl; and pharmaceutically acceptable salts and solvates thereof. Example of solvates include hydrates.

In Formula VII above, with respect to $R^1$, the term "aryl" as part of an arylC$_{1-3}$ alkyl group means phenyl or phenyl substituted by one or more (e.g., 1, 2, or 3) substituents selected from halogen, $C_{1-6}$ alkyl, $C_{1-6}$ alkoxy, and methylenedioxy. The term "heteroaryl" as part of a heteroarylC$_{1-3}$ alkyl group means thienyl, furyl, or pyridyl, each optionally substituted by one or more (e.g., 1, 2, or 3) substituents selected from halogen, $C_{1-6}$ alkyl, and $C_{1-6}$ alkoxy. The term "$C_3$-8 cycloalkyl" as a group or part of a $C_3$-8 cycloalkyl$C_{1-3}$ alkyl group means a monocyclic ring comprising three to eight carbon atoms. Examples of suitable cycloalkyl rings include the $C_3$-6 cycloalkyl rings cyclopropyl, cyclobutyl, cyclopentyl, and cyclohexyl.

In formula VII above, with respect to $R^2$, optional benzene ring substituents are selected from one or more (e.g., 1, 2, or 3) atoms or groups comprising halogen, hydroxy, $C_{1-6}$ alkyl, $C_{1-6}$ alkoxy, $CO_2R^b$, halo$C_{1-6}$ alkyl, halo$C_{1-6}$ alkoxy, cyano, nitro, and $NR^aR^b$, where $R^a$ and $R^b$ are each hydrogen or $C_{1-6}$ alkyl, or $R^a$ also can represent $C_{2-7}$ alkanoyl or $C_{1-6}$ alkylsulphonyl. Optional substituents for the remaining ring systems are selected from one or more (e.g., 1, 2, or 3) atoms or groups comprising halogen, $C_{1-6}$ alkyl, $C_{1-6}$ alkoxy, and aryl$C_{1-3}$ alkyl as defined above. The bicyclic ring

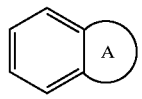

can, for example, represent naphthalene, a heterocycle such as benzoxazole, benzothiazole, benzisoxazole, benzimidazole, quinoline, indole, benzothiophene, benzofuran, or

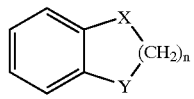

wherein n is an integer 1 or 2 and X and Y each can represent $CH_2$, O, S, or NH.

Unless otherwise indicated, in the above formulae, as well as other formulae described herein, the term "alkyl," as a group or part of a group, means a straight chain or, where available, a branched chain moiety containing the indicated number of carbon atoms. For example, it can represent a $C_{1-4}$ alkyl function as represented by methyl, ethyl, n-propyl, i-propyl, n-butyl, s-butyl, and t-butyl. The term "alkenyl" as used herein includes straight chained and branched alkenyl groups containing the indicated number of carbon atoms, such as vinyl and allyl groups. The term "alkynyl" as used herein includes straight chained and branched alkynyl groups containing the indicated number of carbon atoms, suitably acetylene.

Unless other indicated, in the above formulae, as well as other formulae disclosed herein, the term "halogen" herein means a fluorine, chlorine, bromine, or iodine atom.

Unless other indicated, in the above formulae, as well as other formulae disclosed herein, the term "halo$C_{1-6}$ alkyl" means an alkyl group as defined above comprising one to six carbon atoms substituted at one or more carbon atoms by one or more (e.g., 1, 2, or 3) halogen atoms. Similarly, a halo$C_{1-6}$ alkoxy group is a halo$C_{1-6}$ alkyl group as defined above linked to the $R^2$ benzene ring via an oxygen atom. Examples of halo$C_{1-6}$ alkyl groups include trifluoromethyl and 2,2,2-trifluoroethyl. An example of a halo$C_{1-6}$ alkoxy group is trifluoromethoxy. The term "$C_{2-7}$ alkanoyl" means a $C_{1-6}$ alkanoyl group where the $C_{1-6}$ alkyl portion is as defined above. An example of a suitable $C_{2-7}$ alkanoyl group is the $C_2$ alkanoyl group acetyl.

Unless other indicated, in the above formulae, as well as other formulae disclosed herein, when $R^0$ is a halogen atom or a $C_{1-6}$ alkyl group, this substituent can be sited at any available position on the phenyl portion of the tetracyclic ring. However, a particular site of attachment is the ring 10-position.

The compounds of Formula VI can contain two or more asymmetric centers, and, thus, can exist as enantiomers or diastereoisomers. In particular, in Formula VII above, two ring chiral centers are denoted with asterisks. It is to be understood that the invention includes both mixture and separate individual isomers of the compounds of Formula (VII).

The compounds of Formula VI also can exist in tautomeric forms, and the invention includes both mixtures and separate individual tautomers thereof.

A particular group of compounds for use in the methods of the invention are those compounds of Formula VI in which $R^0$ is hydrogen or halogen (e.g., fluorine), especially hydrogen.

Another particular group of compounds for use in the methods of the invention are those of Formula VI in which $R^1$ represents hydrogen, $C_{1-4}$ alkyl, halo$C_{1-4}$ alkyl, $C_3$-6 cycloalkyl, $C_3$-6 cycloalkylmethyl, pyridyl$C_{1-3}$ alkyl, furyl$C_{1-3}$ alkyl, or optionally substituted benzyl. Within this particular group of compounds, examples of $C_{1-4}$ alkyl groups are methyl, ethyl, n-propyl, i-propyl, and n-butyl. Examples of $C_3$-6 cycloalkylmethyl groups are cyclopropylmethyl and cyclohexylmethyl. Examples of optionally substituted, benzyl groups include benzyl and halobenzyl (e.g., fluorobenzyl).

A further group of compounds for use in the methods of the invention are those compounds of Formula VI in which $R^2$ represents an optionally substituted benzene, thiophene, furan, pyridine, or naphthalene ring, or an optionally substituted bicyclic ring

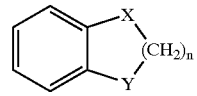

wherein n is 1 or 2, and X and Y are each $CH_2$ or O.
Within this particular group of compounds, examples of substituted benzene groups are benzene substituted by one of halogen (e.g., chlorine), hydroxy, $C_{1-3}$ alkyl (e.g., methyl, ethyl, or i-propyl), $C_{1-3}$ alkoxy (e.g., methoxy or ethoxy), $CO_2R^b$, halomethyl (e.g., trifluoromethyl), halomethoxy (e.g., trifluoromethoxy), cyano, nitro, or $NR^aR^b$ wherein $R^a$ and $R^b$ are each hydrogen or methyl, or $R^a$ is acetyl, or benzene substituted by dihalo (e.g., dichloro) or by $C_{1-3}$ alkoxy (e.g., methoxy) and one of halogen (e.g., chlorine) and hydroxy. An example of a substituted thiophene ring is a halo (e.g., bromo) substituted thiophene ring.

A still further particular group of compounds of Formula VI are those where $R^3$ represents hydrogen or $R^1$ and $R^3$ together represent a 3-membered alkyl chain.

A preferred group of compounds of the invention are the cis isomers of Formula VI represented by formula (IX)

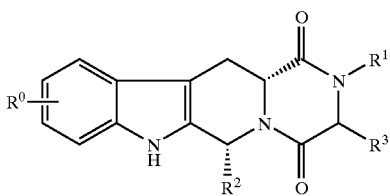

and mixtures thereof with their cis optical enantiomers, including racemic mixtures, and salts and solvates of these compounds in which $R^0$ is hydrogen or halogen and $R^1$, $R^2$, and $R^3$ are as defined previously. Examples of solvates include hydrates. Examples of halogen include flourine.

The single isomers represented by Formula IX, i.e., the 6R, 12aR isomers, are particularly preferred.

Within the above definitions for Formula IX, $R^1$ preferably can represent $C_{1-4}$ alkyl (e.g., methyl, ethyl, i-propyl, and n-butyl), $C_3$-6 cycloalkyl (e.g., cyclopentyl) or $C_3$-6 cycloalkylmethyl (e.g., cyclopropylmethyl).

$R^2$ preferably can represent a substituted benzene ring such as benzene substituted by $C_{1-3}$ alkoxy (e.g., methoxy) or by $C_{1-3}$ alkoxy (e.g., methoxy) and halogen (e.g., chlorine), particularly 4-methoxyphenyl or 3-chloro-4-methoxyphenyl, or $R^2$ preferably can represent 3,4-methylenedioxyphenyl.

A particularly preferred subgroup of compounds of the above formula are compounds wherein $R^0$ represents hydrogen.

A further preferred subgroup includes compounds wherein $R^1$ is selected from hydrogen, methyl, and isopropyl.

Preferably, $R^2$ represents the unsubstituted bicyclic ring

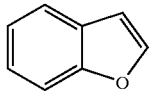

A still further subgroup of compounds of Formula IX, are compounds wherein $R^3$ represents hydrogen or methyl.

It is to be understood that the present invention covers all appropriate combinations of particular and preferred groupings hereinabove.

Particular compounds suitable for use in the methods of the invention include:

cis-2,3,6,7,12,12a-hexahydro-2-(4-pyridyl-methyl)-6-(3,4-methylenedioxyphenyl)-pyrazino[2',1';6,1]-pyrido[3,4-b]indole-1,4-dione;

cis-2,3,6,7,12,12a-hexahydro-6-(2,3-dihydrobenzo[b]furan-5-yl)-2-methyl-pyrazino[2',1';6,1]pyrido-[3,4-b]indole-1,4-dione;

cis-2,3,6,7,12,12a-hexahydro-6-(5-bromo-2-thienyl)-2-methylpyrazino[2',1';6,1]pyrido[3,4-b]indole-1,4-dione;

cis-2,3,6,7,12,12a-hexahydro-2-butyl-6-(4-methylphenyl)-pyrazino[2',1'; 6,1]pyrido[3,4-b]indole-1,4-dione;

(6R,12aR)-2,3,6,7,12,12a-hexahydro-2-isopropyl-6-(3,4-methylenedioxyphenyl)-pyrazino[2',1';6,1]pyrido-[3,4-b]indole-1,4-dione;

(6R,12aR)-2,3,6,7,12,12a-hexahydro-2-cyclopentyl-6-(3,4-methylenedioxyphenyl)-pyrazino[2',1';6,1]-pyrido[3,4-b]indole-1,4-dione;

(6R,12aR)-2,3,6,7,12,12a-hexahydro-2-cyclopropylmethyl-6-(4-methoxyphenyl)-pyrazino[2',1';6,1]-pyrido[3,4-b]indole-1,4-dione;

(6R,12aR)-2,3,6,7,12,12a-hexahydro-6-(3-chloro-4-methoxyphenyl)-2-methyl-pyrazino[2',1';6,1]pyrido[3,4-b]indole-1,4-dione;

(6R,12aR)-2,3,6,7,12,12a-hexahydro-2-methyl-6-(3,4-methylenedioxyphenyl)-pyrazino[2',1';6,1]pyrido[3,4-b]indole-1,4-dione;

(6R,12aR)-2,3,6,7,12,12a-hexahydro-6-(3,4-methylenedioxyphenyl)-pyrazino[2',1';6,1]pyrido[3,4-b]indole-1,4-dione;

(5aR, 12R, 14aS)-1,2,3,5,6,11,12,14a-octahydro-12-(3,4-methylenedioxyphenyl)-pyrrolo[1",2":4'5']-pyrazino[2',1';6,1]pyrido[3,4-b]indole-5-1,4-indione, (6R,12aR)-2,3,6,7,12,12a-hexahydro-6-(5-benzofuranyl)-2-methyl-pyrazino[2',1';6,1]pyrido[3,4-b]indole-1,4-dione;

(6R,12aR)-2,3,6,7,12,12a-hexahydro-6-(5-benzofuranyl)-pyrazino[2',1';6,1]pyrido[3,4-b]indole-1,4-dione;

(3S, 6R, 12aR)-2,3,6,7,12,12a-hexahydro-6-(5-benzofuranyl)-3-methyl-pyrazino[2',1';6,1]pyrido[3,4-b]indole-1,4-dione;

(3S, 6R, 12aR)-2,3,6,7,12,12a-hexahydro-6-(5-benzofuranyl)-2,3-dimethyl-pyrazino[2',1',6,1]pyrido[3,4-b]indole-1,4-dione;

(6R, 12aR)-2,3,6,7,12,12a-hexahydro-6-(5-benzofuranyl)-2-isopropyl-pyrazino[2',1',6,1]pyrido[3,4-b]indole-1,4-dione; and physiologically acceptable solvates (e.g., hydrates) thereof.

The invention is also compatible with administration of particular cGMP PDE inhibitors disclosed in U.S. Pat. No. 6,140,329, at least some of which compounds have been described in said U.S. Pat. No. 6,143,746. Preferred compounds of the U.S. Pat. No. 6,140,329 are set forth in the following Formula X including pharmaceutically acceptable salts thereof.

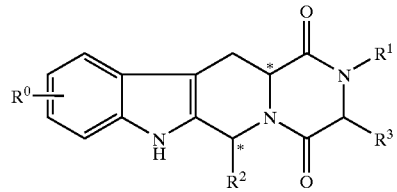

wherein in Formula X:
$R^0$ represents hydrogen, halogen or $C_{1-6}$ alkyl;
$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl$C_{1-3}$ alkyl, aryl$C_{1-3}$ alkyl or heteroaryl$C_{1-3}$ alkyl;
$R^2$ represents an optionally substituted monocyclic aromatic ring selected from benzene, thiophene, furan and pyridine or an optionally substituted bicyclic ring

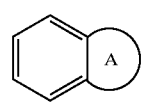

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and
$R^3$ represents hydrogen or $C_{1-3}$ alkyl, or $R^1$ and $R^3$ together represent a 3- or 4-membered alkyl or alkenyl chain; and pharmaceutically acceptable solvates thereof. Examples of solvates includes hydrates.

Additional suitable individual compounds of the invention for use in the treatment include:

Cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione;

Cis-2,3,6,7,12,12-hexahydro-6-(2,3-dihydrobenzo[b]furan-5-yl)-2-methyl-pyrazino[2',1':6,1]pyrido[3,4-b]indole-1,4-dione;

Cis-2,3,6,7,12,12a-hexahydro-6-(5-bromo-2-thienyl)-2-methyl-pyrazino[2',1':6,1]pyrido[3,4-b]indole-1,4-dione;

Cis-2,3,6,7,12,12a-hexahydro-2-butyl-6-(4-methylphenyl)-pyrazino[2',1':6,1]pyrido[3,4-b]indole-1,4-dione;

(6R,12aR)-2,3,6,7,12,12a-Hexahydro-2-isopropyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopentyl-6-(3,4-methylenedioxyphenyl)-pyrazino[2',1':6,1]pyrido[3,4-b]indole-1,4-dione;

(6R,12aR)-2,3,6,7,12, 12a-Hexahydro-2-cyclopropylmethyl-6-(4-methoxyphenyl)-pyrazino[2',1':6,1]pyrido[3,4-b]indole-1,4-dione;

(6R,12aR)-2,3,6,7,12,12a-Hexahydro-6-(3-chloro-4-methoxyphenyl)-2-methyl-pyrazino[2',1':6,1]pyrido[3,4-b]indole-1,4-dione;

(6R,12aR)-2,3,6,7,12,12a-Hexahydro-2-methyl-6-(3,4-methylenedioxyphenyl)-pyrazino[2',1':6,1]pyrido[3,4-b]indole-1,4-dione;

(6R,12aR)-2,3,6,7,12,12a-Hexahydro-6-(3,4-methylenedioxyphenyl)-pyrazino[2',1':6,1]pyrido[3,4-b]indole-1,4-dione;

(5aR,12R,14aS)-1,2,3,5,6,11,12,14a-Octahydro-12-(3,4-methylenedioxyphenyl)-pyrrolo[1",2":4',5']pyrazino[2',1':6,1]pyrido[3,4-b]indole-5-1,4-dione;

Cis-2,3,6,7,12,12a-hexahydro-2-cyclopropyl-6-(3,4-methylenedioxyphenyl)-pyrazino[2',1':6,1]pyrido[3,4-b]indole-1,4-dione;

(3 S,6R,12aR)-2,3,6,7,12,12a-hexahydro-3-methyl-6-(3,4-methylenedioxyphenyl)-pyrazino[2',1':6,1]pyrido[3,4-b]indole-1,4-dione;

and physiologically acceptable salts and solvates (e.g. hydrates) thereof.

Specifically suitable compounds for use in the methods of the invention include:

(6R,12aR)-2,3,6,7,12,12a-hexahydro-2-methyl-6-(3,4-methylenedioxyphenyl)-pyrazino[2',1':6,1]pyrido[3,4-b]indole-1,4-dione(Compound A); and (3S,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione (Compound B);

and physiologically acceptable salts and solvates (e.g. hydrates) thereof.

In another invention embodiment, at least one of the administered compounds is a carboline derivative or N-cinnamoyl derivative or (β) carbolines as described in the U.S. Pat. Nos. 6,043,252 and 6,117,881. Such preferred compounds are set forth in the following Formulae XI and XIII including pharmaceutically acceptable salts thereof.

Compounds of Formula XI are represented by the following structure:

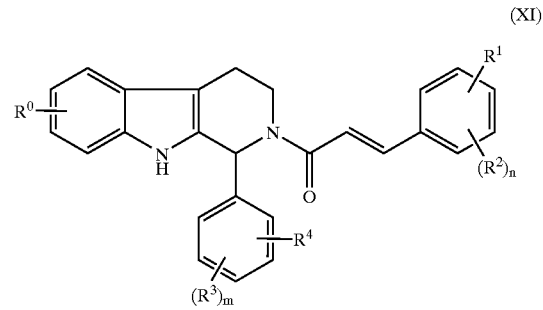

(XI)

wherein in that Formula XI:

$R^0$ represents hydrogen or halogen;

$R^1$ is selected from the group consisting of:

hydrogen, $NO_2$, trifluoromethyl, trifluoromethoxy, halogen, cyano, a 5- or 6-membered heterocyclic group containing at least one heteroatom selected from oxygen, nitrogen and sulphur, and is optionally substituted by —C(=O)$OR^a$ or $C_{1-4}$ alkyl, $C_{1-6}$ alkyl optionally substituted by —$OR^a$, $C_{1-3}$ alkoxy, C(=O)$R^a$, O—C(=O)$R^a$, C(=O)$OR^a$, $C_{1-4}$ alkyleneC(=O)$OR^a$, O—$C_{1-4}$ alkylene-C(=O)$OR^a$, $C_{1-4}$ alkylene-O—$C_{1-4}$ alkylene-C(=O)$OR^a$, C(=O)$NR^aSO_2R^c$, C(=O)$C_{1-4}$ alkyleneHet, $C_{1-4}$ alkylene$NR^aR^b$, $C_{2-6}$ alkenylene$NR^aR^b$, C(=O)$NR^aR^b$, C(=O)$NR^aR^c$, C(=O)$NR^aC_{1-4}$ alkyleneO$R^b$C(=O)$NR^a$ $C_{1-4}$ alkyleneHet, $OR^aOC_{2-4}$ alkylene $NR^aR^b$, $OC_{1-4}$ alkylene-CH(O$R^a$)CH$_2$$NR^aR^b$, O—$C_{1-4}$ alkylene Het, O—$C_{2-4}$ alkylene-O$R^a$, O—$C_{2-4}$ alkylene-$NR^a$—C(=O)$OR^b$, $NR^aR^b$, $NR^aC_{1-4}$ alkylene$NR^aR^b$, $NR^aC$(=O)$R^b$, $NR^aC$(=O)$NR^aR^b$, N(SO$_2$ $C_{1-4}$ alkyl)$_2$, $NR^a$(SO$_2$ $C_{1-4}$ alkyl), SO$_2$$NR^aR^b$, and OSO$_2$ trifluoromethyl; $R^2$ is selected from the group consisting of: hydrogen, halogen, O$R^a$, $C_{1-6}$ alkyl, NO$_2$, and $NR^aR^b$, or $R^1$ and $R^2$ are taken together to form a 3- or 4-membered alkylene or alkenylene chain component of a 5- or 6-membered ring, optionally containing at least one heteroatom;

$R^3$ is selected from the group consisting of: hydrogen, halogen, NO$_2$, trifluoromethoxy, $C_{1-6}$ alkyl, and C(=O)$OR^a$; $R^4$ is hydrogen, or $R^3$ and $R^4$ are taken together to form a 3- or 4-membered alkylene or alkenylene chain component of a 5- or 6-membered ring, optionally containing at least one heteroatom;

Het represents a 5- or 6-membered heterocyclic group containing at least one heteroatom selected from the group consisting of oxygen, nitrogen, and sulfur, and is optionally substituted with $C_{1-4}$ alkyl;

$R^a$ and $R^b$ can be the same or different, and are independently selected from hydrogen and $C_{1-6}$ alkyl;

$R^c$ represents phenyl or $C_{4-6}$ cycloalkyl, wherein the phenyl or $C_{4-6}$ cycloalkyl can be optionally substituted by one or more halogen atoms, one or more —C(=O) $OR^a$, or one or more —$OR^a$;

n is an integer selected from 1, 2 and 3;

m is an integer selected from 1 and 2;

and pharmaceutically acceptable salts and solvates thereof. Examples of solvates include hydrates.

In the above Formula XI, the term alkyl or alkylene as used herein respectively contains the indicated number of carbon atoms and includes straight chained and branched alkyl or alkylene groups, typically methyl, methylene, ethyl, and ethylene groups, and straight chained and branched propyl, propylene, butyl, and butylene groups. The term $C_{2-6}$ alkenylene as used with respect to Formula XI means groups that contain 2 to 6 carbon atoms and includes straight chained and branched alkenylene groups, in particular ethenylene or the like. In Formula XI, the term $C_{4-6}$ cycloalkyl denotes cyclic groups containing 4 to 6 carbon atoms, namely cyclobutane, cyclopentane, and cyclohexane. In Formula XI, the term halogen as used herein includes fluorine, chlorine, bromine, and iodine. In Formula XI, the term 5- or 6-membered heterocyclic group as used herein includes 5- or 6-membered heterocycloalkyl and heteroaryl groups, e.g., tetrahydrofuranyl, piperidyl, piperazinyl, pyrrolidinyl, morpholinyl, pyridyl, imidazolyl, furyl, and tetrazolyl. In Formula XI, appropriately, $R^0$ represents hydrogen. Alternatively, $R^0$ can represent halogen, in particular fluorine. In Formula XI, $R^1$ may suitably represent any of —$OR^a$, —O—$C_{2-4}$ alkyleneNR$^a$R$^b$, —O—$C_{1-4}$ alkyleneHet and —O—$C_{2-4}$ alkylene-OR$^a$. In particular, $R^1$ represents —O—$C_{2-4}$ alkyleneNR$^a$R$^b$, wherein $C_{2-4}$ alkylene can represent ethylene, and, $R^a$ and $R^b$ can independently represent methyl. Particularly suitably $R^2$ represents hydrogen. Alternatively, in the case where $R^1$ and $R^2$ together form a 3- or 4-membered alkylene or alkenylene chain component of a 5- or 6-membered ring, optionally containing at least one heteroatom as hereinbefore described, $R^1$ and $R^2$ together form a methylenedioxy chain, an ethyleneoxy chain, an ethylenedioxy chain, an ethenyleneoxy chain, a propylene chain, a butylene chain or —NR$^a$ ethylene-O—. Aptly, $R^1$ and $R^2$ together form methylenedioxy, propylene, or —N(CH$_3$)—(CH$_2$)$_2$—O—.

In the above Formula XI, suitably $R^3$ and $R^4$ taken together form a 3- or 4-membered alkylene or alkenylene chain component of a 5- or 6-membered ring, optionally containing at least one heteroatom as hereinbefore described. Particularly $R^3$ and $R^4$ together form a methylenedioxy chain, an ethyleneoxy chain, an ethylenedioxy chain, an ethenyleneoxy chain, a propylene chain, a butylene chain, or —NR$^a$ ethylene-O—. Aptly $R^3$ and $R^4$ together form a methylenedioxy chain, an ethyleneoxy chain, an ethylenedioxy chain, an ethenyleneoxy chain, or a propylene chain. In particular, $R^3$ and $R^4$ together form methylenedioxy or ethyleneoxy, most particularly ethyleneoxy.

A particular subgroup of compounds for use in the methods of the invention include those of the following formula (XII)

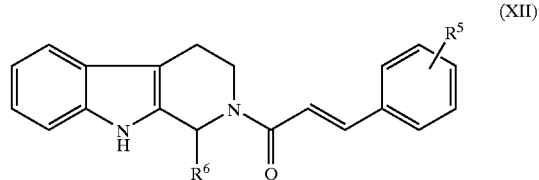

(XII)

wherein $R^5$ is selected from the group consisting of —OH, —OC$_{2-4}$ alkylene NR$^a$ R$^b$, and O—C$_{1-4}$ alkylene Het, wherein Het is as hereinbefore described, and $R^6$ represents

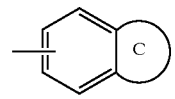

wherein C represents a 5- or 6-membered ring which can be saturated or partially or fully unsaturated, and comprises carbon atoms and optionally one or two heteroatoms selected from oxygen, sulphur and nitrogen, optionally substituted by $C_{1-4}$ alkyl;

and pharmaceutically acceptable salts and solvates thereof. Examples solvates include hydrates.

In that Formula XII, typically, $R^5$ represents —OC$_{2-4}$ alkylene NR$^a$R$^b$, in particular —OCH$_2$CH$_2$N(CH$_3$)$_2$. Alternatively, $R^5$ can represent —O—C$_{1-4}$ alkylene Het, where Het can be piperidyl, pyrrolidinyl (optionally substituted by $C_{1-4}$ alkyl, e.g., methyl) or morpholinyl.

Particularly $R^6$ represents

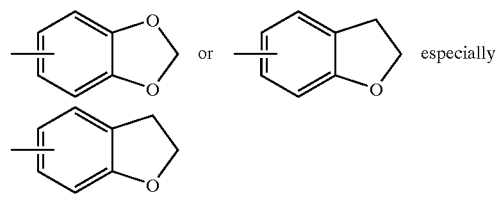

especially

Additional particular compounds for use in the methods of the invention include:

(E)-1-(1-Phenyl-1,3,4,9-tetrahydro-β-carbolin-2-yl)-3-phenylpropene-1-one;
(E)-1-(1-Phenyl-1,3,4,9-tetrahydro-β-carbolin-2-yl)-3-(4-nitrophenyl)propene-1-one;
(E)-1-(1-Phenyl-1,3,4,9-tetrahydro-β-carbolin-2-yl)-3-(4-trifluoromethylphenyl)propene-1-one;
(E)-1-(1-Phenyl-1,3,4,9-tetrahydro-β-carbolin-2-yl)-3-(4-methoxyphenyl)propene-1-one;
(E)-1-[1-(4-Methoxyphenyl)-1,3,4,9-tetrahydro-β-carbolin-2-yl]-3-(4-trifluoromethylphenyl) propene-1-one;
(E)—N-[4-[3-Oxo-3-(1-phenyl-1,3,4,9-tetrahydro-β-carbolin-2-yl)propenyl]phenyl]acetamide;
(E)-1-[1-(4-Methoxyphenyl)-1,3,4,9-tetrahydro-β-carbolin-2-yl]-3-phenylpropene-1-one;
(E)-1-[1-(3,4-Methylenedioxyphenyl)-1,3,4,9-tetrahydro-β-carbolin-2-yl]-3-phenylpropene-1-one;
(E)-1-(1-Phenyl-1,3,4,9-tetrahydro-β-carbolin-2-yl)-3-(4-formylphenyl) propene-1-one;
(E)—N-[4-[3-Oxo-3-(1-(4-nitrophenyl)-1,3,4,9-tetrahydro-β-carbolin-2-yl)propenyl]phenyl]acetamide;
(E)-1-[1-(4-Nitrophenyl)-1,3,4,9-tetrahydro-β-carbolin-2-yl]-3-phenylpropene-1-one;
(E)-1-[1-(4-Trifluoromethoxyphenyl)-1,3,4,9-tetrahydro-β-carbolin-2-yl]-3-phenylpropene-1-one;
(E)-1-[1-(4-Methylphenyl)-1,3,4,9-tetrahydro-β-carbolin-2-yl]-3-phenylpropene-1-one;
(E)—N-[4-[3-Oxo-3-(1-(3,4-methylenedioxyphenyl)-1,3,4,9-tetrahydro-β-carbolin-2-yl)-propenyl]phenyl]acetamide;
(E)-4-[3-Oxo-3-(1-phenyl-1,3,4,9-tetrahydro-β-carbolin-2-yl)-propenyl]benzoic acid, methyl ester;
(E)-1-[1-(2-Chlorophenyl)-1,3,4,9-tetrahydro-β-carbolin-2-yl]-3-phenylpropene-1-one;
(E)-1-(1-Phenyl-1,3,4,9-tetrahydro-β-carbolin-2-yl)-3-(3,4-methylenedioxyphenyl)-propene-1-one;

(E)-1-[1-(3,4-Methylenedioxyphenyl)-1,3,4,9-tetrahydro-β-carbolin-2-yl]-3-(4-bromophenyl)-propene-1-one;
(E)-1-[1-(4-Chlorophenyl)-1,3,4,9-tetrahydro-β-carbolin-2-yl]-3-phenylpropene-1-one;
(E)-1-[1-(3,4-Methylenedioxyphenyl)-1,3,4,9-tetrahydro-β-carbolin-2-yl]-3-(4-ethoxyphenyl)propene-1-one;
(E)-4-[3-Oxo-3-(1-(3,4-methylenedioxyphenyl)-1,3,4,9-tetrahydro-β-carbolin-2-yl)propenyl]acetic acid, phenyl ester;
(E)-1-[1-(3,4-Methylenedioxyphenyl)-1,3,4,9-tetrahydro-β-carbolin-2-yl]-3-(4-hydroxyphenyl)propene-1-one;
(E)-1-[1-(3,4-Methylenedioxyphenyl)-1,3,4,9-tetrahydro-β-carbolin-2-yl]-3-(4-formylphenyl)propene-1-one;
(E)-1-[4-[3-Oxo-3-(1-(3,4-methylenedioxyphenyl)-1,3,4,9-tetrahydro-β-carbolin-2-yl)-propenyl]phenyl]-3-phenylurea;
(E)-1-[1-(3,4-Methylenedioxyphenyl)-1,3,4,9-tetrahydro-β-carbolin-2-yl]-3-(4-aminophenyl)-propene-1-one;
(E)-1-[1-(3,4-Methylenedioxy-phenyl)-1,3,4,9-tetrahydro-β-carbolin-2-yl]-3-(4-nitrophenyl)-propene-1-one;
(E)-1-[1-(3,4-Methylenedioxyphenyl)-1,3,4,9-tetrahydro-β-carbolin-2-yl]-3-[(4-bis(methylsulfonyl)-aminophenyl]-propene-1-one;
(E)-4-[3-Oxo-3-[1-(3,4-methylenedioxyphenyl)-1,3,4,9-tetrahydro-β-carbolin-2-yl]-propenyl]benzoic acid, methyl ester;
(E)—N-[4-[3-Oxo-3-[1-(3,4-methylenedioxyphenyl)-1,3,4,9-tetrahydro-β-carbolin-2-yl]propenyl]phenyl]methanesulfonamide;
(E)-4-[3-Oxo-3-[1-(3,4-methylenedioxyphenyl)-1,3,4,9-tetrahydro-β-carbolin-2-yl]propenyl]benzamide];
(E)-4-[3-Oxo-3-[1-(3,4-methylenedioxyphenyl)-1,3,4,9-tetrahydro-β-carbolin-2-yl]-propenyl]benzoic acid;
(E)-1-[1-(3,4-Methylenedioxyphenyl)-1,3,4,9-tetrahydro-β-carbolin-2-yl]-3-(4-cyanophenyl)propene-1-one;
(E)-1-[1-(3,4-Methylenedioxyphenyl)-1,3,4,9-tetrahydro-β-carbolin-2-yl]-3-(4-trifluoromethylphenyl)propene-1-one;
(E)-1-[1-(3,4-Methylenedioxyphenyl)-1,3,4,9-tetrahydro-β-carbolin-2-yl]-3-(3,4-methylenedioxyphenyl)propene-1-one;
(E)-1-[1-(3,4-Methylenedioxyphenyl)-1,3,4,9-tetrahydro-β-carbolin-2-yl]-3-(4-chlorophenyl)-propene-1-one;
(E)-1-[1-(3,4-Methylenedioxyphenyl)-1,3,4,9-tetrahydro-β-carbolin-2-yl]-3-(4-trifluoromethoxyphenyl)propene-1-one;
(E)-1-[1-(3,4-Methylenedioxyphenyl)-1,3,4,9-tetrahydro-β-carbolin-2-yl]-3-(4-methylphenyl)propene-1-one;
(E)-[4-[3-Oxo-3-(1-(3,4-methylenedioxyphenyl)-1,3,4,9-tetrahydro-β-carbolin-2-yl)propenyl]phenyl]urea;
(E)-1-[1-(3,4-Methylenedioxyphenyl)-1,3,4,9-tetrahydro-β-carbolin-2-yl]-3-(4-hydroxymethylphenyl)propene-1-one;
(E)—N-Benzyl-4-[3-oxo-3-(1-(3,4-methylenedioxyphenyl)-1,3,4,9-tetrahydro-beta.-carbolin-2-yl)propenyl]benzamide;
(E)-1-[1-(3,4-Methylenedioxyphenyl)-1,3,4,9-tetrahydro-β-carbolin-2-yl]-3-(2,4-dichlorophenyl)propene-1-one;
(E)-1-[1-(3,4-Methylenedioxyphenyl)-1,3,4,9-tetrahydro-β-carbolin-2-yl]-3-(3-methoxy-4-hydroxyphenyl)propene-1-one;
(E)-1-[1-(3,4-Methylenedioxyphenyl)-1,3,4,9-tetrahydro-β-carbolin-2-yl]-3-(3-hydroxy-4-methoxyphenyl)propene-1-one;
(E)-1-[1-(3,4-Methylenedioxyphenyl)-1,3,4,9-tetrahydro-β-carbolin-2-yl]-3-(4-fluorophenyl)-propene-1-one;
(E)-1-[1-(3,4-Methylenedioxyphenyl)-1,3,4,9-tetrahydro-β-carbolin-2-yl]-3-indan-5-yl-1-propene-1-one;
(E)—N-[4-[3-Oxo-3-(1-(3,4-methylenedioxyphenyl)-1,3,4,9-tetrahydro-β-carbolin-2-yl)propenyl]benzoyl]benzenesulfonamide;
(E)-1-[1-(3,4-Methylenedioxyphenyl)-1,3,4,9-tetrahydro-β-carbolin-2-yl]-3-(3,4-dichlorophenyl)propene-1-one;
(E)-1-[1-(3,4-Methylenedioxyphenyl)-1,3,4,9-tetrahydro-β-carbolin-2-yl]-3-(3,4-dimethoxyphenol)propene-1-one;
(E)-1-[1-(3,4-Methylenedioxyphenyl)-1,3,4,9-tetrahydro-β-carbolin-2-yl]-3-(3,4-dihydroxyphenyl)propene-1-one;
(E)—N-Methyl-N-[4-[3-oxo-3-(1-(3,4-methylenedioxyphenyl)-1,3,4,9-tetrahydro-β-carbolin-2-yl)propenyl]phenyl]acetamide;
(E)-2,2-Dimethyl-N-[4-[3-Oxo-3-(1-(3,4-methylenedioxyphenyl)-1,3,4,9-tetrahydro-β-carbolin-2-yl)propenyl]phenyl]propionamide;
(E)-1-[1-(3,4-Methylenedioxyphenyl)-1,3,4,9-tetrahydro-β-carbolin-2-yl]-3-(3,5-dimethoxyphenyl)propene-1-one;
(E)—(N)-{4-[3-[1-(3,4-Methylenedioxyphenyl)-6-fluoro-1,3,4,9-tetrahydro-beta-carbolin-2-yl]-3-oxopropenyl]-phenyl}-acetamide;
(E)-1-[1-(3,4-Methylenedioxyphenyl)-1,3,4,9-tetrahydro-β-carbolin-2-yl]-3-(3,4,5-trimethoxyphenyl)propene-1-one;
(E)—N-[4-[3-Oxo-3-(1-(3,4-methylenedioxyphenyl)-1,3,4,9-tetrahydro-β-carbolin-2-yl)propenyl]phenyl]isobutyramide;
(E)-1-[1-(3,4-Methylenedioxyphenyl)-6-fluoro-1,3,4,9-tetrahydro-β-carbolin-2-yl]-3-phenylpropene-1-one;
(E)—N-(2-Methoxyethyl)-4-[3-oxo-3-(1-(3,4-methylenedioxyphenyl)-1,3,4,9-tetrahydro-β-carbolin-2-yl)propenyl]benzamide;
(E)-1-[1-(3,4-Methylenedioxyphenyl)-1,3,4,9-tetrahydro-β-carbolin-2-yl]-3-(3-hydroxyphenyl)propene-1-one;
(E)-1-[1-(3,4-Methylenedioxyphenyl)-1,3,4,9-tetrahydro-β-carbolin-2-yl]-3-(3-methoxyphenyl)propene-1-one;
(E)-1-[1-(3,4-Methylenedioxyphenyl)-1,3,4,9-tetrahydro-β-carbolin-2-yl]-3-(3-nitrophenyl)propene-1-one;
(E)-1-[1-(3,4-Methylenedioxyphenyl)-1,3,4,9-tetrahydro-β-carbolin-2-yl]-3-[4-(2-dimethylaminoethoxy)phenyl]propene-1-one;
(E)—N-(2-Morpholin-4-ylethyl)-4-[3-oxo-3-(1-(3,4-methylenedioxyphenyl)-1,3,4,9-tetrahydro-β-carbolin-2-yl)propenyl]benzamide;
(E)-1-[1-(3,4-Methylenedioxyphenyl)-1,3,4,9-tetrahydro-β-carbolin-2-yl]-3-[4-(1H-tetrazol-5-yl)phenyl]propene-1-one;
(E)-1-[1-(3,4-Methylenedioxyphenyl)-1,3,4,9-tetrahydro-β-carbolin-2-yl]-3-(3-aminophenyl)propene-1-one;
(E)—N-Cyclohexyl-4-[3-oxo-3-(1-(3,4-methylenedioxyphenyl)-1,3,4,9-tetrahydro-β-carbolin-2-yl)propenyl]benzamide;
(E)—N-(Tetrahydrofuran-2-ylmethyl)-4-[3-oxo-3-(1-(3,4-methylenedioxyphenyl)-1,3,4,9-tetrahydro-β-carbolin-2-yl)propenyl]benzamide;
(E)-1-[1-(3,4-Methylenedioxyphenyl)-1,3,4,9-tetrahydro-β-carbolin-2-yl]-3-(3-cyanophenyl)propene-1-one;
(E)—N-(4-Piperidine-4-carboxylic acid, ethyl ester)-4-[3-oxo-3-(1-(3,4-methylenedioxyphenyl)-1,3,4,9-tetrahydro-β-carbolin-2-yl)propenyl]benzamide;
(E)—N-(4-Piperidine-4-carboxylic acid)-4-[3-oxo-3-(1-(3,4-methylenedioxyphenyl)-1,3,4,9-tetrahydro-β-carbolin-2-yl)propenyl]benzamide;
(E)-3-[3-Oxo-3-[1-(3,4-methylenedioxyphenyl)-1,3,4,9-tetrahydro-(3-carbolin-2-yl]-propenyl]benzoic acid
(E)-1-[1-(3,4-Methylenedioxyphenyl)-1,3,4,9-tetrahydro-β-carbolin-2-yl]-3-(3-(4-methylpiperazine-1-carbonyl)-phenyl)propene-1-one
(E)—N-(2-Piperazin-1-ylethyl)-3-[3-oxo-3-(1-(3,4-methylenedioxyphenyl)-1,3,4,9-tetrahydro-β-carbolin-2-yl)propenyl]benzamide (E)-4-[3-Oxo-3-(1-(3,4-methylenedioxyphenyl)-1,3,4,9-tetrahydro-β-carbolin-2-yl)-propenyl]acetic acid ethyl ester (E)-1-[1-(3,4-Methylenedioxyphenyl)-1,3,4,9-tetrahydro-β-carbolin-2-yl]-3-(3-tetrazolophenyl)propene-1-one (E)-2-[3-Oxo-3-[1-(3,4-methylenedioxyphenyl)-1,3,4,9-tetrahydro-β-carbolin-2-yl]-propenyl]benzoic acid, methyl ester (E)-3-[3-Oxo-3-[1-(3,4-methylenedioxyphenyl)-1,3,4,9-tetrahydro-β-carbolin-2-yl]-propenyl]benzoic acid, methyl ester (E)-1-(4-[3-Oxo-3-(1-(3,4-methylenedioxyphenyl)-1,3,4,9-tetrahydro-1-carbolin-2-yl)-propenyl]phenyl)piperidine-4-carboxylic acid, ethyl ester (E)—N-(1-Ethylpyrrolidin-2-yl-methyl)-3-[3-oxo-3-(1-(3,4-methylenedioxyphenyl)-1,3,4,9-tetrahydro-β-carbolin-2-yl)propenyl]benzamide (E)-1-[1-(3,4-Methylenedioxyphenyl)-1,3,4,9-tetrahydro-β-carbolin-2-yl]-3-(3-(2-dimethylaminoethoxy)phenyl)propene-1-one (E)-1-[1-(3,4-Methylenedioxyphenyl)-1,3,4,9-tetrahydro-β-carbolin-2-yl]-3-(3,5-diterbutyl-4-hydroxyphenyl)propene-1-one (E)-3-[3-Oxo-3-[1-(4-methoxycarbonylphenyl)-1,3,4,9-tetrahydro-β-carbolin-2-yl]propenyl]benzoic acid, methyl ester (E)-2-[3-Oxo-3-[1-(3,4-methylenedioxyphenyl)-1,3,4,9-tetrahydro-β-carbolin-2-yl]propenyl]benzoic acid (E)-(4-[3-Oxo-3-(1-(3,4-methylenedioxyphenyl)-1,3,4,9-tetrahydro-β-carbolin-2-yl)propenyl]phenoxy)acetic acid, ethyl ester (E)-(4-[3-Oxo-3-(1-(3,4-methylenedioxyphenyl)-1,3,4,9-tetrahydro-β-carbolin-2-yl)-propenyl]phenyl)acetic acid (E)-(4-[3-Oxo-3-(1-(3,4-methylenedioxyphenyl)-1,3,4,9-tetrahydro-β-carbolin-2-yl)propenyl]phenoxy)acetic acid (E)-1-[1-(3,4-Methylenedioxyphenyl)-1,3,4,9-tetrahydro-β-carbolin-2-yl]-3-(3-nitro-4-chlorophenyl)propene-1-one (E)-1-[1-(3,4-Methylenedioxyphenyl)-1,3,4,9-tetrahydro-β-carbolin-2-yl]-3-(5-nitro-2-chlorophenyl)propene-1-one (E)-3-Chloro-4-[3-oxo-3-[1-(3,4-methylenedioxyphenyl)-1,3,4,9-tetrahydro-beta.-carbolin-2-yl]propenyl]benzoic acid, methyl ester (E)-(4-[3-Oxo-3-(1-(3,4-methylenedioxyphenyl)-1,3,4,9-tetrahydro-β-carbolin-2-yl)propenyl]benzyloxy)acetic acid (E)-1-[1-(3,4-Methylenedioxyphenyl)-1,3,4,9-tetrahydro-β-carbolin-2-yl]-3-(5-amino-2-chlorophenyl)propene-1-one (E)-3-Chloro-4-[3-oxo-3-[1-(3,4-methylenedioxyphenyl)-1,3,4,9-tetrahydro-beta-carbolin-2-yl]propenyl]benzoic acid (E)-1-[1-(3,4-Methylenedioxyphenyl)-1,3,4,9-tetrahydro-β-carbolin-2-yl]-3-(3,5-dibromo-4-hydroxyphenyl)propene-1-one (E)-1-[1-(3,4-Methylenedioxyphenyl)-1,3,4,9-tetrahydro-β-carbolin-2-yl]-3-(4-(2-dimethylaminopropoxy)phenyl)propene-1-one (E)-2-Chloro-5-[3-oxo-3-[1-(3,4-methylenedioxyphenyl)-1,3,4,9-tetrahydro-beta-carbolin-2-yl]propenyl]benzoic acid, methyl ester (E)-1-[1-(3,4-Methylenedioxyphenyl)-1,3,4,9-tetrahydro-β-carbolin-2-yl]-3-(4-(2-diisopropylaminoethoxy)phenyl)propene-1-one (E)-2-Chloro-5-[3-oxo-3-[1-(3,4-methylenedioxyphenyl)-1,3,4,9-tetrahydro-beta-carbolin-2-yl]propenyl]benzoic acid (E)-1-[1-(3,4-Methylenedioxyphenyl)-1,3,4,9-tetrahydro-β-carbolin-2-yl]-3-(3-hydroxy-4-nitro-phenyl)propene-1-one (E)-1-[1-(3,4-Methylenedioxyphenyl)-1,3,4,9-tetrahydro-β-carbolin-2-yl]-3-(3,5-dimethyl-4-hydroxyphenyl)propene-1-one (E)-1-[1-(3,4-Methylenedioxyphenyl)-1,3,4,9-tetrahydro-β-carbolin-2-yl]-3-(3-(2-dimethylaminoethoxy)-4-nitrophenyl)propene-1-one (E)-1-[1-(3,4-Methylenedioxyphenyl)-1,3,4,9-tetrahydro-β-carbolin-2-yl]-3-(3-(2-dimethylaminoethoxy)-4-aminophenyl)propene-1-one (E)-1-[1-(3,4-Methylenedioxyphenyl)-1,3,4,9-tetrahydro-β-carbolin-2-yl]-3-(3-nitro-4-hydroxy-5-methoxyphenyl)propene-1-one (E)-1-[1-(3,4-Methylenedioxyphenyl)-1,3,4,9-tetrahydro-β-carbolin-2-yl]-3-(3-chlorophenyl)propene-1-one (E)-1-[1-(4-Methoxy-phenyl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2,6-dichlorophenyl)propene-1-one (E)-1-[1-(3,4-Methylenedioxyphenyl)-1,3,4,9-tetrahydro-β-carbolin-2-yl]-3-(4-methylaminomethylphenyl)propene-1-one (E)-1-[1-(3,4-Methylenedioxyphenyl)-1,3,4,9-tetrahydro-β-carbolin-2-yl]-3-(3-methylphenyl)propene-1-one (E)—N-Methyl-(4-[3-oxo-3-(1-(3,4-methylenedioxyphenyl)-1,3,4,9-tetrahydro-beta-carbolin-2-yl)propenyl]benzenesulfonamide (E)-1-[1-(3,4-Methylenedioxyphenyl)-1,3,4,9-tetrahydro-β-carbolin-2-yl]-3-(3-hydroxy-4-acetylphenyl)propene-1-one (E)-1-[1-(2,3-Dihydrobenzofuran-5-yl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2-hydroxyphenyl)propene-1-one (E)-1-[1-(3,4-Methylenedioxyphenyl)-1,3,4,9-tetrahydro-β-carbolin-2-yl]-3-(3-nitro-2-piperidin-1-ylphenyl)propene-1-one (E)-1-[1-(2,3-Dihydrobenzofuran-5-yl)-1,3,4,9-tetrahydro-β-carbolin-2-yl]-3-phenylpropene-1-one (E)-1-[1-(4-Isopropylphenyl)-1,3,4,9-tetrahydro-β-carbolin-2-yl]-3-(3-nitrophenyl)propene-1-one (E)-1-[1-(2,3-Dihydrobenzofuran-5-yl)-1,3,4,9-tetrahydro-β-carbolin-2-yl]-3-(3-nitrophenyl)propene-1-one (E)—(R)-1-[1-(3,4-Methylenedioxyphenyl)-1,3,4,9-tetrahydro-β-carbolin-2-yl]-3-phenylpropene-1-one (E)-(S)-1-[1-(3,4-Methylenedioxyphenyl)-1,3,4,9-tetrahydro-β-carbolin-2-yl]-3-phenylpropene-1-one (E)-1-[1-(4-Methoxyphenyl)-1,3,4,9-tetrahydro-β-carbolin-2-yl]-3-(3-nitrophenyl)propene-1-one (E)-1-[1-(4-Methylphenyl)-1,3,4,9-tetrahydro-β-carbolin-2-yl]-3-(2-chloro-5-nitrophenyl)propene-1-one (E)—N-(Tetrahydrofuran-2-ylmethyl)-3-[3-oxo-3-(1-(3,4-methylenedioxy)-1,3,4,9-tetrahydro-β-carbolin-2-yl)propenyl]benzamide (E)-1-[1-(Indan-5-yl)-1,3,4,9-tetrahydro-β-carbolin-2-yl]-3-phenylpropene-1-one (E)-1-[1-(3,4-Methylenedioxyphenyl)-1,3,4,9-tetrahydro-β-carbolin-2-yl]-3-(3-acetylphenyl)propene-1-one (E)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one (E)-4-[3-Oxo-3-[1-(4-methoxyphenyl)-1,3,4,9-tetrahydro-β-carbolin-2-yl]propenyl]benzoic acid, methyl ester (E)-1-[1-(3,4-Methylenedioxyphenyl)-1,3,4,9-tetrahydro-β-carbolin-2-yl]-3-(4-methyl-3,4-dihydro-2H-benzo[1,4]-oxazin-6-yl)propene-1-one (E)-1-[1-(3,4-Methylenedioxyphenyl)-1,3,4,9-tetrahydro-β-carbolin-2-yl]-3-(2-hydroxy-5-nitrophenyl)propene-1-one (E)-4-[3-Oxo-3-[1-(2,3-dihydrobenzofuran-5-yl)-1,3,4,9-tetrahydro-β-carbolin-2-yl]propenyl]benzoic acid, methyl ester (E)-4-[3-Oxo-3-[1-(4-methoxyphenyl)-1,3,4,9-tetrahydro-β-carbolin-2-yl]propenyl]benzoic acid (E)-4-[3-Oxo-3-[1-(2,3-dihydrobenzofuran-5-yl)-1,3,4,9-tetrahydro-β-carbolin-2-yl]propenyl]benzoic acid (E)-1-[1-(Benzofuran-5-yl)-1,3,4,9-tetrahydro-β-carbolin-2-yl]-3-phenylpropene-1-one (E)-3-[3-Oxo-3-(1-(3,4-methylenedioxyphenyl)-,3,4,9-tetrahydro-β-carbolin-2-yl)-propenyl]phenyl)trifluoromethanesulfonic acid, phenyl ester (E)-1-[1-(3,4-Methylenedioxyphenyl)-1,3,4,9-tetrahydro-β-carbolin-2-yl]-3-[4-(2-hydroxyethoxy)phenyl]propene-1-one (E)-1-[1-(Benzofuran-5-yl-1,3,4,9-tetrahydro-β-carbolin-2-yl)]-3-(4-(2-dimethylaminoethoxy)phenyl)propene-1-one (E)-1-[1(3,4-Methylenedioxyphenyl)-1,3,4,9-tetrahydro-β-carbolin-2-yl]-3-(2-dimethylaminophenyl)propene-1-one (E)-1-[1-(3,4-Methylenedioxyphenyl)-1,3,4,9-tetrahydro-(3-carbolin-2-yl)-3-(2-1-ylphenyl)propene-1-one (E)-4-[3-Oxo-3-[1-(benzofuran-5-yl-1,3,4,9-tetrahydro-β-carbolin-2-yl]-propenyl]-benzoic acid, methyl ester (E)-4-[3-(1-Benzofuran-5-yl-1,3,4,9-tetrahydro-β-carbolin-2-yl)-3-oxo-propenyl]-benzoic acid (E)-4-[3-Oxo-3-(1-(3,4-methylenedioxyphenyl)-1,3,4,9-tetrahydro-β-carbolin-2-yl)propenyl]phenyl)trifluoromethanesulfonic acid, phenyl ester (E)-1-[1-(3,4-Methylenedioxyphenyl)-1,3,4,9-tetrahydro-β-carbolin-2-yl]-3-(2-(2-dimethylaminoethoxy)phenyl)propene-1-one (E)-1-[1-(3-Fluoro-4-methoxyphenyl)-1,3,4,9-tetrahydro-β-carbolin-2-yl]-3-phenylpropene-1-one (E)—(R)-1-[1-(2,3-Dihydrobenzofuran-5-yl)-1,3,4,9-tetrahydro-β-carbolin-2-yl)]-3-(4-dimethylaminoethoxy)phenyl)propene-1-one (E)-[1-(2,3-Dihydrobenzo[1,4]dioxin-6-yl)-1,3,4,9-tetrahydro-β-carbolin-2-yl]-3-phenylpropene-1-one (E)-1-[1-(2,3-Dihydrobenzofuran-5-yl)-1,3,4,9-tetrahydro-β-carbolin-2-yl)]pyrrolidin-1-ylethoxy)phenyl)propene-1-one (E)-1-[1-(3,4-Methylenedioxyphenyl)-1,3,4,9-tetrahydro-β-carbolin-2-yl]-3-[4-pyrrolidin-1-ylphenyl]propene-1-one (E)-(R)-1-[1-(2,3-Dihydrobenzofuran-5-yl)-1,3,4,9-tetrahydro-β-carbolin-2-yl]-3-(3-nitrophenyl)propene-1-one (E)-1-[1-(3,4-Methylenedioxyphenyl)-1,3,4,9-tetrahydro-β-carbolin-2-yl]-3-[4-imidazol-1-ylphenyl]propene-1-one (E)-4-[3-[1-(2,3-Dihydrobenzo[1,4]dioxin-6-yl)-1,3,4,9-tetrahydro-β-carbolin-2-yl]-3-oxo-propenyl]benzoic acid, methyl ester (E)-1-[1-(2,3-Dihydrobenzo[1,4]dioxin-6-yl)-1,3,4,9-tetrahydro-β-carbolin-2-yl]-3-(3-nitrophenyl)propene-1-one (E)-1-[1-(2,3-Dihydrobenzo[1,4]dioxin-6-yl)-1,3,4,9-tetrahydro-β-carbolin-2-yl)]-3-(4-(2-dimethylaminoethoxy)phenyl)propene-1-one (E)-1-[1-(3-Fluoro-4-methoxyphenyl)-1,3,4,9-tetrahydro-β-carbolin-2-yl)]-3-(4-(2-dimethylaminoethoxy)phenyl)propene-1-one (E)-4-[3-[1-(2,3-Dihydrobenzo[1,4]dioxin-6-yl)-1,3,4,9-tetrahydro-β-carbolin-2-yl]-3-oxopropenyl]benzoic acid (E)-(R)-1-[1-(2,3-Dihydrobenzofiran-5-yl)-1,3,4,9-tetrahydro-β-carbolin-2-yl]-3-phenylpropene-1-one (E)-(S)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one (E)-1-[1-(2,3-Dihydrobenzofuran-5-yl)-1,3,4,9-tetrahydro-β-carbolin-2-yl]-3-(4-aminophenyl)propene-1-one (E)-(S)-1-[1-(2,3-Dihydrobenzofiran-5-yl)-1,3,4,9-tetrahydro-β-carbolin-2-yl]-3-phenylpropene-1-one (E)-(S)-1-[1-(2,3-Dihydrobenzofuran-5-yl)-1,3,4,9-tetrahydro-β-carbolin-2-yl]-3-(3-nitrophenyl)propene-1-one (E)-(R)-1-[1-(2,3-Dihydrobenzofuran-5-yl)-1,3,4,9-tetrahydro-β-carbolin-2-yl)]-3-(4-(1-(S)-methylpyrrolidin-2-yl-methoxy)phenyl)propene-1-one (E)-(R)-1-[1-(2,3-Dihydrobenzofuran-5-yl)-1,3,4,9-tetrahydro-β-carbolin-2-yl]-3-(3-hydroxyphenyl)propene-1-one (E)-(R)-1-[1-(2,3-Dihydrobenzofuran-5-yl)-1,3,4,9-tetrahydro-β-carbolin-2-yl)]-3-(4-(2-dimethylamino-1-methylethoxy)phenyl)propene-1-one (E)-1-(1-Phenyl-1,3,4,9-tetrahydro-1-carbolin-2-yl)-3-(4-(4-methylpyperazin-1-yl)-phenyl)propene-1-one (E)-(R)-1-[1-(3,4-Methylenedioxyphenyl)-1,3,4,9-tetrahydro-β-carbolin-2-yl)]-3-(4-(1-(S)-methylpyrrolidin-2-yl-methoxy)phenyl)propene-1-one (E)-(R)-1-[1-(3,4-Methylenedioxyphenyl)-1,3,4,9-tetrahydro-β-carbolin-2-yl)]-3-(4-(2-dimethylamino-1-methylethoxy)phenyl)propene-1-one (E)-(R)-1-[1-(3,4-Methylenedioxyphenyl)-1,3,4,9-tetrahydro-β-carbolin-2-yl)]-3-(4-(2-dimethylaminopropoxy)phenyl)propene-1-one (E)-4-[3-Oxo-3-[1-(3,4-fluorophenyl)-1,3,4,9-tetrahydro-p-carbolin-2-yl]propenyl]benzoic acid, methyl ester (E)-(R)-[1-(2,3-Dihydrobenzofuran-5-yl)-1,3,4,9-tetrahydro-β-carbolin-2-yl)]-3-(4-(2-diethylaminoethoxy)phenyl)propene-1-one (E)-(R)1-[1-(2,3-Dihydrobenzofuran-5-yl)-1,3,4,9-tetrahydro-β-carbolin-2-yl)]-3-(4-(2-dimethylaminopropoxy)phenyl)propene-1-one (E)-4-[3-Oxo-3-[1-(3,4-difluorophenyl)-1,3,4,9-tetrahydro-β-carbolin-2-yl]propenyl]benzoic acid (E)-(R)-1-[1-(2,3-Dihydrobenzofuran-5-yl)-1,3,4,9-tetrahydro-β-carbolin-2-yl]-3-(4-aminophenyl)propene-1-one (E)-(R)-1-[1-(3,4-Methylenedioxyphenyl)-1,3,4,9-tetrahydro-β-carbolin-2-yl]-3-(4-aminophenyl)propene-1-one (E)-(R)-1-[1-(3,4-Methylenedioxyphenyl)-1,3,4,9-tetrahydro-β-carbolin-2-yl]-3-(4-(2-pyrrolidin-1-ylethoxy)phenyl)propene-1-one (E)-(R)-1-[1-(3,4-Methylenedioxyphenyl)-1,3,4,9-tetrahydro-β-carbolin-2-yl)]-3-(4-(2-diethylaminoethoxy)phenylpropene-1-one (E)-1-1[-(3-Fluoro-4-methoxyphenyl)-1,3,4,9-tetrahydro-β-carbolin-2-yl)]-3-(3-nitrophenyl)propene-1-one (E)-(R)-1-[1-(2,3-Dihydrobenzofuran-5-yl)-1,3,4,9-tetrahydro-β-carbolin-2-yl]-3-(4-trifluoromethylphenyl)propene-1-one (E)-(R)-1-[1-(2,3-Dihydrobenzofiran-5-yl)-1,3,4,9-tetrahydro-β-carbolin-2-yl]-3-(3-trifluoromethylphenyl)propene-1-one (E)-(R)-1-[1-(2,3-Dihydrobenzofiran-5-yl)-1,3,4,9-tetrahydro-β-carbolin-2-yl]-3-(2-morpholin-4-ylethoxy)phenyl)propene-1-one (E)-(R)-1-[1-(2,3-Dihydrobenzofuran-5-yl)-1,3,4,9-tetrahydro-β-carbolin-2-yl]-3-(4-(2-(ethylmethylamino)ethoxy)phenyl)propene-1-one (E)-1-[1-(2,3-Dihydrobenzofuran-5-yl)-1,3,4,9-tetrahydro-β-carbolin-2-yl]-3-(4-(3-(dimethylamino)propenyl)phenyl)propene-1-one (E)-(R)-1-[1-(2,3-Dihydrobenzofiran-5-yl)-1,3,4,9-tetrahydro-β-carbolin-2-yl]-3-(4-(3-dimethylamino-2-hydroxypropoxy)phenyl)propene-1-one (E)-(R)-1-(1-(2,3-Dihydrobenzofuran-5-yl)-1,3,4,9-tetrahydro-β-carbolin-2-yl)-3-(4-formylphenyl)propene-1-one (E)-(R)-1-[1-(2,3-Dihydrobenzofuran-5-yl)-1,3,4,9-tetrahydro-β-carbolin-2-yl]-3-(4-propylaminomethyl)phenyl)propene-1-one (E)-(R)-1-[1-(2,3-Dihydrobenzofiran-5-yl)-1,3,4,9-tetrahydro-β-carbolin-2-yl]-3-[4-(2-dimethylaminoethylamino)phenylpropene-1-one (E)-(R)-1-[1-(2,3-Dihydrobenzofuran-5-yl)-1,3,4,9-tetrahydro-β-carbolin-2-yl]-3-(4-(2-aminoethoxy)phenyl)propene-1-one (E)-(R)-1-[1-(2,3-Dihydrobenzofuran-5-yl)-1,3,4,9-tetrahydro-β-carbolin-2-yl]-3-(4-hydroxyphenyl)propene-1-one (E)-(R)-1-[1-(2,3-Dihydrobenzofuran-5-yl)-1,3,4,9-tetrahydro-β-carbolin-2-yl]-3-(4-(4-methylpiperazin-1-yl)phenylpropene-1-one (E)-(R)-1-[1-(2,3-Dihydrobenzofuran-5-yl)-1,3,4,9-tetrahydro-β-carbolin-2-yl]-3-(4-methylaminomethyl)phenyl)propene-1-one (E)-(R)-1-[1-(2,3-Dihydrobenzofuran-5-yl)-1,3,4,9-tetrahydro-β-carbolin-2-yl]-3-(4-isopropylaminomethyl)phenyl)propene-1-one (E)-(R)-1-[1-(2,3-Dihydrobenzofuran-5-yl)-1,3,4,9-tetrahydro-β-carbolin-2-yl]-3-(4-dimethylaminomethyl)phenyl)propene-1-one (E)-(R)-1-[1-(2,3-Dihydrobenzofuran-5-yl)-1,3,4,9-tetrahydro-β-carbolin-2-yl]-3-[4-(3-dimethylaminopropoxy)phenyl]propene-1-one (E)-(R)-1-[1-(2,3-Dihydrobenzo furan-5-yl)-1,3,4,9-tetrahydro-β-carbolin-2-yl]-3-(4-(2-piperidin-1-ylethoxy)phenyl)propene-1-one (E)-1-[1-(3,4-Methylenedioxyphenyl)-1,3,4,9-tetrahydro-β-carbolin-2-yl)-3-(4-(2-piperidin-1-yl-ethoxy)phenyl]propene-1-one (E)-(R)-[2-(4-{3-[1-(2,3-Dihydrobenzofuran-5-yl)-1,3,4,9-tetrahydro-β-carbolin-2-yl]-3-oxopropenyl}-phenoxy)ethyl]methylcarbamic acid, tertbutyl ester (E)-(R)-1-[1-(2,3-Dihydrobenzofuran-5-yl)-1,3,4,9-tetrahydro-carbolin-2-yl]-3-[4-(2-methylaminoethoxy)phenyl]propene-1-one and pharmaceutically acceptable salts and solvates (e.g., hydrates) thereof.

A specific compound of the invention is:

(E)-(R)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one, and pharmaceutically acceptable salts and solvates (e.g., hydrates) thereof.

In another invention embodiment, at least one of the administered compounds is a chemical compound described in the U.S. Pat. Nos. 6,143,757 and 6,001,847. Such preferred compounds are set forth in the following Formula XIII including pharmaceutically acceptable salts thereof.

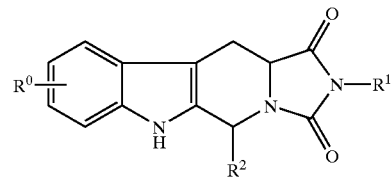

wherein in Formula XIII:

$R^0$ represents hydrogen, halogen, or $C_{1-6}$alkyl;

$R^1$ is selected from the group consisting of:

(a) hydrogen, (b) $C_{1-6}$alkyl, optionally substituted with one or more substituents selected from phenyl, halogen, —$CO_2R_a$ and —$NR_aR_b$, (c) $C_{3-6}$cycloalkyl, (d) phenyl, and (e) a 5- or 6-membered heterocyclic ring containing at least one heteroatom selected from oxygen, nitrogen and sulphur, and being optionally substituted with one or more $C_{1-6}$alkyl, and optionally linked to the nitrogen atom to which $R_1$ is attached via $C_{1-6}$alkyl;

$R_2$ is selected from the group consisting of:

(f) $C_{3-6}$cycloalkyl, (g) phenyl, optionally substituted with one or more substituents selected from —$OR_a$, —$NR_aR_b$, halogen, hydroxy, trifluoromethyl, cyano, and nitro, (h) a 5- or 6-membered heterocyclic ring containing at least one heteroatom selected from oxygen, nitrogen and sulphur; and (i) a bicyclic ring

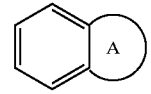

attached to the rest of the molecule via one of the benzene ring carbon atoms, wherein A is a 5- or 6-membered heterocyclic ring as defined in (h); and $R_a$ and $R_b$, independently, represent hydrogen or $C_{1-6}$alkyl.

In the above Formula XIII, the term "$C_{1-6}$alkyl" denotes any straight or branched alkyl chain containing 1 to 6 carbon atoms, and includes methyl, ethyl, n-propyl, iso-propyl, n-butyl, pentyl, hexyl, and the like. The term "halogen" denotes fluorine, chlorine, bromine, and iodine.

A particular group of compounds according to Formula XIII are those wherein $R_0$ represents any of hydrogen, methyl, bromine, and fluorine, but the definition of $R_0$ given in Formula XIII includes within its scope other $C_{1-6}$-alkyl and halogen groups.

In Formula XIII above, $R_1$ preferably can represent a substituent selected from methyl, ethyl (optionally substituted by one or more chlorine atoms), butyl, cyclohexyl and benzyl. Other $R_1$ substituents include hydrogen; cycloalkyl groups, such as cyclopropyl; $C_{1-6}$alkyl, typically ethyl or propyl, substituted by an —$NR_aR_b$ substituent, such as a dimethylamino substituent; phenyl optionally linked to the nitrogen atom to which $R_1$ is attached via a $C_{1-6}$alkyl chain, such as ethyl or the like; and $C_{1-6}$alkyl, e.g., methyl, substituted by —$CO_2R_a$, such as —$CH_2CO_2Et$ (Et is $CH_2CH_3$) and the like.

Suitable heterocyclic rings within the definition of $R_1$ of Formula XIII include pyridyl, morpholinyl, piperazinyl, pyrrolidinyl, and piperidinyl. Generally, such heterocyclic rings are linked to the nitrogen atom to which $R_1$ is attached via a $C_{1-6}$alkyl chain, more appropriately a $C_{1-4}$alkyl chain.

A particular substituent represented by $R_2$ is

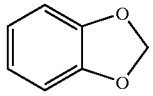

Other $R_2$ substituents include thienyl, pyridyl, furyl, and phenyl, wherein phenyl can be substituted with one or more substituents selected from —$OR_a$ (e.g., methoxy), —$NR_aR_b$ (e.g., dimethylamino), halogen (in particular chlorine or fluorine), hydroxy, trifluoromethyl, cyano, and nitro. Alternatively, $R_2$ can represent a $C_{3-6}$cycloalkyl group, such as cyclohexyl or the like.

The pharmaceutically acceptable salts of the compounds of Formula XIII that contain a basic center are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulphonate, benzenesulphonate, and p-toluenesulphonate salts. Compounds of Formula XIII also can provide pharmaceutically acceptable metal salts, in particular alkali metal salts, with bases. Examples include the sodium and potassium salts.

It is to be understood that the present invention covers all appropriate combinations of particular and preferred groupings hereinabove.

Additional particular compounds of the above formulae suitable for use in the methods of the invention include:

Cis-2-benzyl-5-(3,4-methylenedioxyphenyl)-5,6,11,11a-tetrahydro-1H-imidazo[1',5':1,6]pyrido[3,4-b]indole-1,3(2H)-dione;
Trans-2-benzyl-5-(3,4-methylenedioxyphenyl)-5,6,11,11a-tetrahydro-1H-imidazo[1',5':1,6]pyrido[3,4-b]indole-1,3(2H)-dione;
Cis-5-(4-methoxyphenyl)-2-methyl-5,6,11,11a-tetrahydro-1H-imidazo[1',5':1,6]pyrido[3,4-b]indole-1,3(2H)-dione;
Cis-2-ethyl-5-(4-methoxyphenyl)-5,6,11,11a-tetrahydro-1H-imidazo[1',5':1,6]pyrido[3,4-b]indole-1,3(2H)-dione;
Trans-2-ethyl-5-(4-methoxyphenyl)-5,6,11,11a-tetrahydro-1H-imidazo[1',5':1, 6]pyrido[3,4-b]indole-1,3(2H)-dione;
Trans-2-ethyl-5-(3,4-methylenedioxyphenyl)-5,6,11,11a-tetrahydro-1H-imidazo [1',5':1,6]pyrido[3,4-b]indole-1,3 (2H)-dione;
Trans-2-ethyl-5-(2-thienyl)-5,6,11,11a-tetrahydro-1H-imidazo-[1',5':1,6]pyrido[3,4-b]indole-1,3(2H)-dione;
Trans-5-(4-dimethylaminophenyl)-2-ethyl-5,6,11,11a-tetrahydro-1H-imidazo[1',5':1,6]pyrido[3,4-b]indole-1,3 (2H)-dione;
Trans-2-butyl-9-methyl-5-phenyl-5,6,11,11a-tetrahydro-1H-imidazo[1',5':1,6]pyrido[3,4-b]indole-1,3(2H)-dione;
Trans-9-bromo-2-butyl-5-phenyl-5,6,11,11a-tetrahydro-1H-imidazo[1',5':1,6']pyrido[3,4-b]indole-1,3(2H)-dione;
Cis-2-butyl-5-(4-methoxyphenyl)-5,6,11,11a-tetrahydro-1H-imidazo[1',5':1,6]pyrido[3,4-b]indole-1,3(2H)-dione;
Trans-2-butyl-5-(4-methoxyphenyl)-5,6,11,11a-tetrahydro-1H-imidazo[1',5':1,6]pyrido[3,4-b]indole-1,3(2H)-dione;
Cis-2-butyl-5-9-fluoro-5-(4-methoxyphenyl)-5,6,11,1a-tetrahydro-1H-imidazo[1',5':1,6]pyrido[3,4-b]indole-1,3 (2H)-dione;
Trans-2-butyl-9-fluoro-5-(4-methoxyphenyl)-5,6,11,11a-tetrahydro-1H-imidazo[',5':1,6]pyrido[3,4-b]indole-1,3 (2H)-dione;
Trans-2-butyl-5-(3,4-methylenedioxyphenyl)-5,6,11,11a-tetrahydro-1H-imidazo[1',5':1,6]pyrido[3,4-b]indole-1,3 (2H)-dione;
Cis-2-butyl-5-(3-chlorophenyl)-5,6,11,11a-tetrahydro-1H-imidazo[1',5':1,6]pyrido[3,4-b]indole-1,3(2H)-dione;
Trans-2-butyl-5-(3-chlorophenyl)-5,6,11,11a-tetrahydro-1H-imidazo[1',5':1,6]pyrido[3,4-b]indole-1,3(2H)-dione;
Cis-2-butyl-5-(4-chlorophenyl)-5,6,11,11a-tetrahydro-1H-imidazo[1',5':1,6]pyrido[3,4-b]indole-1,3(2H)-dione;
Trans-2-butyl-5-(4-chlorophenyl)-5,6,11,11a-tetrahydro-1H-imidazo[1',5':1,6]pyrido[3,4-b]indole-1,3(2H)-dione;
Trans-2-butyl-5-(4-fluorophenyl)-5,6,11,11a-tetrahydro-1H-imidazo[1',5':1,6]pyrido[3,4-b]indole-1,3(2H)-dione;
Trans-2-butyl-5-(4-hydroxyphenyl)-5,6,11,11a-tetrahydro-1H-imidazo[1',5':1,6]pyrido[3,4-b]indole-1,3(2H)-dione;
Cis-2-butyl-5-(4-trifluoromethylphenyl)-5,6,11,11a-tetrahydro-1H-imidazo-[1',5':1,6]pyrido[3,4-b]indole-1,3 (2H)-dione;
Cis-2-butyl-5-(4-cyanophenyl)-5,6,11,11a-tetrahydro-1H-imidazo[1',5':1,6]pyrido[3,4-b]indole-1,3(2H)-dione;
Trans-2-butyl-5-(4-cyanophenyl)-5,6,11,11a-tetrahydro-1H-imidazo[1',5':1,6]pyrido[3,4-b]indole-1,3(2H)-dione;
Cis-2-butyl-5-(4-nitrophenyl)-5,6,11,11a-tetrahydro-1H-imidazo[1',5':1,6]pyrido[3,4-b]indole-1,3(2H)-dione;
Trans-2-butyl-5-(4-nitrophenyl)-5,6,11,11a-tetrahydro-1H-imidazo[1',5':1,6]pyrido[3,4-b]indole-1,3(2H)-dione;
Cis-2-butyl-5-(3-pyridyl)-5,6,11,11a-tetrahydro-1H-imidazo[1',5':1,6]pyrido[3,4-b]indole-1,3(2H)-dione;
Cis-2-butyl-5-(3-thienyl)-5,6,11,11a-tetrahydro-1H-imidazo[1',5':1,6]pyrido[3,4-b]indole-1,3(2H)-dione;
Trans-2-butyl-5-(3-thienyl)-5,6,11,11a-tetrahydro-1H-imidazo[1',5':1,6]pyrido[3,4-b]indole-1,3(2H)-dione;
Cis-2-butyl-5-(3-furyl)-5,6,11,11a-tetrahydro-1H-imidazo[1',5':1,6]pyrido[3,4-b]indole-1,3(2H)-dione;
Trans-2-butyl-5-(3-furyl)-5,6,11,11a-tetrahydro-1H-imidazo[1',5':1,6]pyrido[3,4-b]indole-1,3(2H)-dione;
Cis-2-cyclohexyl-5-(4-methoxyphenyl)-5,6,11,11a-tetrahydro-1H-imidazo[1',5':1,6]pyrido[3,4-b]indole-1,3 (2H)-dione;
Trans-2-cyclohexyl-5-(4-methoxyphenyl)-5,6,11,11a-tetrahydro-1H-imidazo[1',5':1,6]pyrido[3,4-b]indole-1,3 (2H)-dione;
Cis-2-cyclohexyl-9-fluoro-5-(4-methoxyphenyl)-5,6,11,11a-tetrahydro-1H-imidazo [1',5':1,6]pyrido[3,4-b]indole-1,3(2H)-dione;
Trans-2-cyclohexyl-9-fluoro-5-(4-methoxyphenyl)-5,6,11,11a-tetrahydro-1H-imidazo [1',5':1,6]pyrido[3,4-b]indole-1,3(2H)-dione;
Trans-2-benzyl-5-phenyl-5,6,11,11a-tetrahydro-1H-imidazo[1',5':1,6]pyrido[3,4-b]indole-1,3(2H)-dione;
Cis-2-benzyl-5-(4-methoxyphenyl)-5,6,11,11a-tetrahydro-1H-imidazo[1',5':1,6]pyrido[3,4-b]indole-1,3(2H)-dione;
Trans-2-benzyl-5-(4-methoxyphenyl)-5,6,11,11a-tetrahydro-1H-imidazo[1', 5':1,6]pyrido[3,4-b]indole-1,3 (2H)-dione;
(5R,11aR)-2-benzyl-5-(3,4-methylenedioxyphenyl)-5,6,11,11a-tetrahydro-1H-imidazo [1',5':1,6]pyrido[3,4-b]indole-1,3(2H)-dione;
Trans-2-benzyl-5-(4-hydroxyphenyl)-5,6,11,11a-tetrahydro-1H-imidazo[1',5':1,6]pyrido[3,4-b]indole-1,3 (2H)-dione;
Trans-2-(2-chloroethyl)-5-(4-methoxyphenyl)-5,6,11,11a-tetrahydro-1H-imidazo[1',5':1,6]pyrido[3,4-b]indole-1,3 (2H)-dione;

Cis-2-benzyl-5-cyclohexyl-5,6,11,11a-tetrahydro-1H-imidazo[1',5':1,6]pyrido[3,4-b]indole-1,3(2H)-dione;

Trans-2-benzyl-5-cyclohexyl-5,6,11,11a-tetrahydro-1-H-imidazo[1',5':1,6]pyrido[3,4-b]indole-1,3(2H)-dione;

Trans-2-butyl-5-phenyl-5,6,11,11a-tetrahydro-1H-imidazo[1',5':1,6]pyrido[3,4-b]indole-1,3(2H)-dione;

Trans-2-cyclohexyl-5-phenyl-5,6,11,11a-tetrahydro-1H-imidazo[1',5':1,6]pyrido[3,4-b]indole-1,3(2H)-dione;

Cis-2-cyclohexyl-5-phenyl-5,6,11,11a-tetrahydro-1H-imidazo[1',5':1,6]pyrido[3,4-b]indole-1,3(2H)-dione;

Trans-2-ethoxycarbonylmethyl-5-(4-methoxypheny)-5,6,11,11a-tetrahydro-1H-imidazo[1',5':1,6]pyrido[3,4-bindole-1,3(2H)-dione;

Trans-5-(4-methoxyphenyl)-2-[2-(2-pyridyl)-ethyl]5,6,11,11a-tetrahydro-1H-imidazo [1',5':1,6]pyrido[3,4-b]indole-1,3(2H)-dione;

Trans-2-cyclopropyl-5-phenyl-5,6,11,11a-tetrahydro-1H-imidazo[1',5':1,6]pyrido[3,4-b]indole-1,3(2H)-dione;

Trans-2-phenethyl-5-phenyl-5,6,11,11a-tetrahydro-1H-imidazo[1',5':1,6]pyrido[3,4-b]indole-1,3(2H)-dione;

Trans-5-phenyl-2-(2-pyridylmethyl)-5,6,11,11a-tetrahydro-1H-imidazo[1',5':1,6]pyrido[3,4-b]indole-1,3(2H)-dione;

Trans-5-phenyl-2-(4-pyridylmethyl)-5,6,11,11a-tetrahydro-1H-imidazo[1',5':1,6]pyrido[3,4-b]indole-1,3(2H)-dione;

Trans-5-(4-methoxyphenyl)-2-(3-pyridylmethyl)-5,6,11,11a-tetrahydro-1H-imidazo[1',5':1,6]pyrido[3,4-b]indole-1,3(2H)-dione;

Trans-2-(2-dimethylaminoethyl)-5-(4-methoxyphenyl)-5,6,11,11a-tetrahydro-1H -imidazo[1',5':1,6]pyrido[3,4-b]indole-1,3(2H)-dione;

Trans-2-(3-dimethylaminopropyl)-5-(4-methoxyphenyl)-5,6,11,11a-tetrahydro-1-H-imidazo[1',5':1,6]pyrido[3,4-b]indole-1,3(2H)-dione;

Trans-2-(2-morpholin-4-yl-ethyl)-5-phenyl-5,6,11,11a-tetrahydro-1-H-imidazo[1',5':1,6]pyrido[3,4-b]indole-1,3(2H)-dione;

Trans-5-(4-methoxyphenyl)-2-[3-(4-methyl-piperazin-1-yl)-propyl]-5,6,11,11a-tetrahydro-1-H-imidazo1',5':1,6]pyrido[3,4-b]indole-1,3(2H)-dione;

Trans-5-(4-methoxyphenyl)-2-(2-pyrrolidin-1-yl-ethyl)-5,6,11,11a-tetrahydro-1-H-imidazo[1',5':1,6]pyrido[3,4-b]indole-1,3(2H)-dione;

Trans-5-(4-methoxyphenyl)-2-[2-(1-methyl-pyrrolidin-2-yl)-ethyl]-5,6,11,11a-tetrahydro-1H-imidazo-[1',5':1,6]pyrido[3,4-b]indole-1,3(2H)-dione;

Trans-5-(4-methoxyphenyl)-5,6,11,11a-tetrahydro-1-H-imidazo[1',5':1,6]pyrido[3,4-b]indole-1,3(2H)-dione;

Cis-5-(4-methoxyphenyl)-5,6,11,11a-tetrahydro-1H-imidazo[1',5':1,6]pyrido[3,4-b]indole-1,3(2H)-dione;

and pharmaceutically acceptable salts and solvates thereof.

Particularly preferred compounds of the invention are:

(5R, 11aR)-2-benzyl-5-(3,4-methylenedioxyphenyl)-5,6,11,11a-tetrahydro-1H-imidazo[1',5':1,6]pyrido[3,4-b]indole-1,3(2H)-dione;

Cis-2-cyclohexyl-5-(4-methoxyphenyl)-5,6,11,11a-tetrahydro-1-H-imidazo[1',5':1,6]pyrido[3,4-b]indole-1,3(2H)-dione;

Trans-2-butyl-5-(4-methoxyphenyl)-5,6,11,11a-tetrahydro-1-H-imidazo[1',5':1,6]pyrido[3,4-b]indole-1,3(2H)-dione;

Cis-2-benzyl-5-(3,4-methylenedioxyphenyl)-5,6,11,11a-tetrahydro-1-H-imidazo[1',5':1,6]pyrido[3,4-b]indole-1,3(2H)-dione;

and pharmaceutically acceptable salts and solvates thereof.

As discussed, the invention is compatible with a variety of insulin molecules (e.g., porcine, rabbit, mouse, or human insulins) including biologically active variants thereof including allelic variants. By the term "biological variant" particularly as that term is used to reference a human insulin is meant a molecule having at least one amino acid substitution, deletion or addition when compared to the full-length and mature sequence of human insulin as set forth at pg. 1464 of Kahn, C. R. et al in *The Pharmacological Basis of Therapeutics*, $8^{th}$ ed. (Gilman, A. G et al. eds) McGraw-Hill, Inc. New York.

More particular biologically active variants of the full-length and mature insulin sequence will preferably exhibit at least about 80 or 85%, preferably 90%, more preferably at least about 95%, and more preferably at least about 100% of the activity of the full-length and mature insulin sequence just mentioned. Methods for determining insulin activity are known in include what is sometimes referred to herein as a standard in vitro insulin assay. That assay refers to administering a quantity of insulin to a fasting rabbit and determining the concentration of blood glucose in that rabbit. The standard in vitro insulin assay is more specifically described in Kahn, C. R. as well as references cited therein. One unit of insulin is equal to the amount required to reduce the concentration of blood glucose in the standard in vitro insulin assay to about 45 mg/dl (2.5 mM) after several hours or less.

Biologically active variants of the full-length and mature insulin sequence suitably will have substantial sequence identity with unmodified insulin, e.g. at least about 70%, 80% or 85%, preferably 90%, more preferably at least about 95% sequence identity to unmodified primate, rabbit or rodent insulin, preferably unmodified primate insulin such as human insulin, where such sequence identity is determined by BLAST program.

Particular insulin preparations in accord with this invention are recombinant human insulins including between about 20 to about 40 Units of insulin/mg. Typical formulations include about 1 to about 5 mg of insulin per ml. More concentrated insulin solutions are also available having up to about 500 U/ml.

Methods for making biologically active insulin variants are known and generally involve making mutations at the nucleic acid level, eg., substitutions, additions or deletions (contiguous or non-contiguous) that can provide for substantially homologous nucleic acid sequences encoding the variant. In particular, a given nucleotide sequence can be mutated in vitro or in vivo, to create variations in the nucleotides, e.g., to form new or additional restriction endonuclease sites or to destroy preexisting ones and thereby to facilitate further in vitro modification. Any technique for mutagenesis known in the art can be used including, but not limited to, in vitro site-directed mutagenesis (Hutchinson et al., *J. Biol. Chem.*, 253:6551 (1978)), use of TAB Registered TM linkers (Pharmacia), PCR-directed mutagenesis, and the like.

Unless specified otherwise, the term "pharmaceutically acceptable" or "physiologically acceptable" salts and/or solvates is meant salts of the compounds of the invention which contain a basic centre are, for example, non-toxic acid addition salts formed with inorganic acids such as hydrochloric, hydrobromic, sulphuric and phosphoric acid, with organo-carboxylic acids, or with organo-sulphonic acids. The compounds of the invention can also provide pharmaceutically acceptable metal salts, in particular non-toxic alkali metal salts, with bases. Examples include the sodium and potassium salts. For a review on suitable pharmaceutical salts, see *J. Pharm. Sci.*, 1977, 66,1.

Compounds of the invention can be suitably prepared in accordance with methods described in the U.S. Pat. Nos. 6,100,270; 6,006,735; 6,143,757; 6,143,746; 6,140,329; 6,117,881; 6,043,252; 6,001,847; 5,981,527; and 6,207,829 B1. Some therapuetic compounds are available commercially such as sildenafil (Viagra™).

As discussed, preferred human recombinant insulin is also obtainable from several commercial sources. See The Physician's Desk Reference, supra.

The invention further provides more particular methods for preventing or treating a diabetic gastropathy in a mammal, preferably a primate, rodent or rabitt, more preferably a human subject. In one embodiment, the method includes administering to the mammal a therapeutic amount of at least one of the following:

a) one or more of the compounds represented above by Formulae I-XIII above, above as those formulae are set forth above as well as pharmaceutically acceptable salts thereof, and b) insulin or a biologically active variant thereof, including allelic variants, preferably human insulin provided in a pharmaceutically acceptable and sterile formulation, or a compound that enhance insulin effect or levels in a subject.

In one embodiment of the forgoing method, the administered compound is at least one of the compounds represented by Formulae I–V as those formulae are set forth above as well as pharmaceutically acceptable salts thereof. Preferably, the administered compound is at least one of a pyrazolo[4,3-d]prymidin-7-one, a pryazolo[3,4-d] pyrimidin4-one, a quinazolin-4-one, a purin-6-one, or a pyrido[3,2-d]pyrimidin-4-one or a pharmaceutically acceptable salt thereof. More preferably, the administered compound of the method is at least one of the following compounds:

a) 5-[2-ethoxy-5-(4-methylpiperazin-1-ylsulphonyl) phenyl]-1-methyl-3-n-propyl-1,6-dihydro-7H-pyrazolo [4,3d]pyrimidin-7-one (sildenafil), b) 1-ethyl-5-[5-(n-hexylsulphamoyl)-2-n-propoxy-phenyl]-3-methyl-1,6-dihydro-7 H-pyrazolo[4,3-d]pyrimidin-7-one, c) 1-ethyl-5-(5-diethylsulphamoyl-2-n-propoxy-phenyl)-3-methyl-1,6-dihydro-7H-pyrazolo[4,3-d]-pyrimidin-7-one, d) 5-[5-(N-cyclohexylmethyl-N-methylsulphamoyl)-2-n-propoxyphenyl]-1-ethyl-3-m ethyl-1,6-dihydro-7H-pyrazolo[4,3-d]pyrimidin-7-one;

e) 6-(5-bromo-2-n-propoxyphenyl)-3-methyl-1-n-propyl-1,5-dihydro-4H-pyrazolo[3,4-d]pyrimidin-4-one, f) 3-methyl-6-(5-morpholinosulphonyl-2-n-propoxyphenyl)-1-n-propyl-1,5-dihydro -4H-pyrazolo[3,4-d]pyrimidin-4-one, g) 6-[5-(2-carboxyvinyl)-2-n-propoxzphenyl]-3-methyl-1-n-propyl-1,5-dihydro-4H -pyrazolo[3,4-d]pyrimidin-4-one, h) 6-[5-(2-t-butoxycarbonylvinvy)-2-n-propoxyphenyl]-3-methyl-1-n-propyl-1,5-dihydro-4H-pyrazolo[3,4-d] pyrimidin-4-one, i) 3-methyl-6-[5-(2-morpholinocarbonylvinyl)-2-n-propoxyphenyl]-1-n-propyl-1,5-dihydro-4H-pyrazolo[3, 4-d]pyrimidin-4-one, j) 3-methyl-6-[5-(2-morpholinocarbonylethyl)-2-n-propoxyphenyl]-1-n-propyl-1,5-dihydro-4H-pyrazolo[3, 4-d]pyrimidin-4-one, k) 2-{2-ethoxy-5-[4-(2-hydroxyethyl)-1-piperazinylsulphonyl]phenyl}-8-methylquinazolin-4-(3H)-one, l) 2-{5-[4-(2-hydroxyethyl)-1-piperazinylsulphonyl]-2-n-propoxyphenyl}-8-methylquinazolin-4(3H)-one, m) 8-methyl-2-{5-[2-(4-methyl-1-piperazinylcarbonyl)-ethenyl]-2-n-propoxyphenyl}quinazolin-4(3H)-one, n) 8-carbamoyl-2-{2-ethoxy-5-[4-(2-hydroxyethyl)-1-piperazinylsulphonyl]phenyl}quinazolin-4(3H)-one, k) 8-ethylcarbamoyl-2-(2-n-propoxyphenyl)quinazolin-4(3H)-one,1) 2-[2-ethoxy-5-(4-ethoxycarbonylpiperidinosulphonyl)phenyl]-8-n-propylpyrido[3,2-d]pyrimidin-4 (3H)-one, m) 2-[5-(4-carboxypiperidinosulphonyl)-2-ethoxyphenyl]-8-n-propylpyrido[3,2-d]pyrimidin-4(3H)-one, n) 2-{2-ethoxy-5-[4-(2-hydroxyethyl)-1-piperazinylsulphonyl]phenyl}-8-n-propylpyrido[3,2-d]pyrimidin-4 (3H)-one, o) 2-{2-ethoxy-5-[(bis-3-pyridylsulphonyl)amino]-phenyl}-8-n-propylpyrido[3,2-d]pyrimidin-4(3H)-one;

or a pharmaceutically acceptable salt thereof.

Specifically preferred is administration of sildenafil (Viagra™)

As also discussed above, typical subjects for administration in accordance with the invention are mammals, such as primates, especially humans. For veterinary applications, a wide variety of subjects will be suitable, e.g. livestock such as cattle, sheep and the like; and domesticated animals, particularly pets such as dogs and cats.

In the therapeutic methods of the invention, a subject such as a mammal is suitably selected that is need of treatment, e.g. a subject that is suffering from a GI disorder such as those specified above, preferably a diabetic gastropathy, and then administering to such selected subject a therapeutic compound in accordance with the invention.

Compounds of the invention are suitably administered to a subject in a protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an acidic group is present on a therapeutic compound, a pharmaceutically acceptable salt of an organic or inorganic base can be employed such as an ammonium salt, or salt of an organic amine, or a salt of an alkali metal or alkaline earth metal such as a potassium, calcium or sodium salt. Specifically suitable pharmaceutically acceptable salts also have been disclosed above. Also contemplated are suitable solvates of such compounds as described previously.

In the methods of the invention, a therapeutic compound such as insulin or a PDE inhibitor compound may be administered to a subject by a variety of routes including parenteral (including intravenous, subcutaneous, intramuscular and intradermal), topical (including buccal, sublingual), oral, nasal and the like.

Therapeutic compounds for use in the methods of the invention can be employed, either alone or in combination with one or more other therapeutic agents including one or more prokinetic agents, as a pharmaceutical composition in mixture with conventional excipient, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc. Tablets, capsules and syrups or other fluids are generally preferred for oral administration.

A single or combination of more than one distinct therapeutic compound may be administered in a particular therapy. In this regard, a particular therapy can be optimized by selection of an optimal therapeutic compound, particularly optimal PDE inhibitor compound, or optimal "cocktail" of multiple insulin variants and or PDE inhibitor compounds. Such optimal compound(s) can be readily identified by those skilled in the art, such as by the in vitro and in vivo assays of the examples which follow.

Also, as mentioned above, other pharmaceutical agents may be administered in coordination with administration of a therapeutic compound of the invention, particularly a PDE inhibitor compound. For example, a prokinetic agent, particularly at least one of metoclopramide, domperidone, erythromycin or cisapride, e.g. separately or substantially simultaneously such as by formulating the two agents as a unitary pharmaceutical composition for administration to a patient.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. At least some therapeutic compounds such as sildenafil (Viagra™) and recombinant human insulin have been previously used clinically and thus safety of such compounds is established. Also, doses employed in such prior clinical applications will be provide further guidelines for preferred dosage amounts for methods of the present invention.

Further provided by the present invention are methods for preventing or treating at least one GI disorder in a mammal, which mammal has been subjected to or will be subjected to treatment with a therapeutic amount of at least one prokinetic agent. Examples of suitable prokinetic agents include those described by Gilman, Ed., supra, for example, one or more of metoclopramide, domperidone, erythromycin or cisapride. Choice and dosage of a particular prokinetic agent for use with the invention will be guided by recognized parameters including the GI disorder to be treated, the height and weight of the individual, etc. Preferred administration protocols for the administration of prokinetic agents have been reported in Gilman, E. D., supra.

As has been discussed and will be more apparent from the examples following, we evaluated the role of nNOS in gastropyloric function by monitoring gastric emptying and pyloric neurophysiology in ex vivo organ bath preparations using mice with targeted genomic delerion of nNOS. We found delayed gastric emptying and a loss of NO mediated nonadrenergic, noncholinergic (NANC) relaxation in the pylorus of nNOS$^{-/-}$ mice. Using two models of diabetes in mice, we found that diabetic mice develop delayed, gastric emptying and a loss of NO-mediated NANC relaxation in the pylorus that resembles the phenotype of nNOS$^{-/-}$ mice. nNOS protein and mRNA are depleted in pyloric myenteric neurons of diabetic mice consistent with a lack of NO-mediated pyloric relaxation. Insulin treatment reverses the abnormal physiology of diabetic mice and restores pyloric nNOS protein and mRNA. Treatment of diabetic animals with sildenfil, a cGMP phosphodiesterase inhibitor that augments NO signaling, reverses delayed gastric emptying. Accordingly, the key features of diabetics gastropathy in mice reflect a reversible downregulation of nNOS.

All documents mentioned herein are incorporated herein by reference. The following non-limiting examples are illustrative of the invention.

The following Examples 1–4 are provided in the following reference: C. C. Watkins, et al. (2000) *J. of Clin. Invest.* 106: 373; the disclosure of which is incorporated herein by reference.

EXAMPLE 1 nNOS$^{-/-}$ mice Have Delayed Gastric Emptying and Lack Pyloric NANC Relaxation.

Figure 1B:
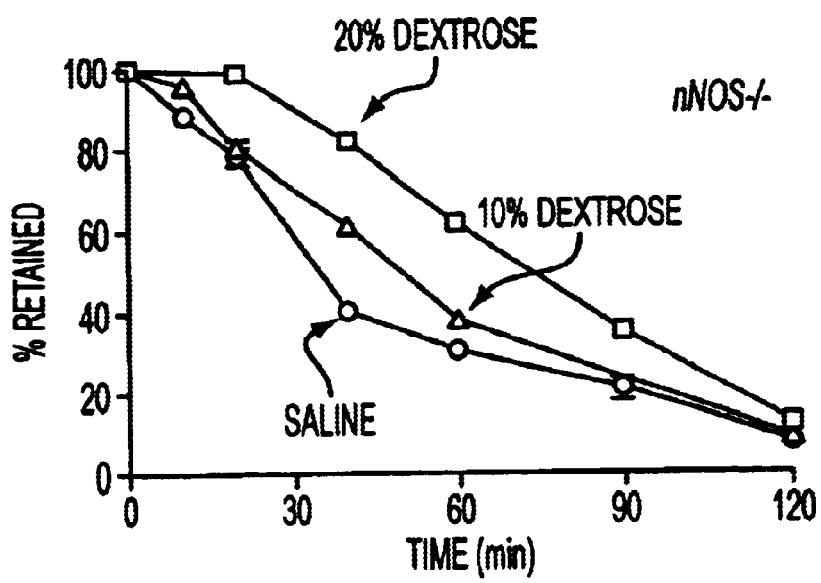
Figure 1C:
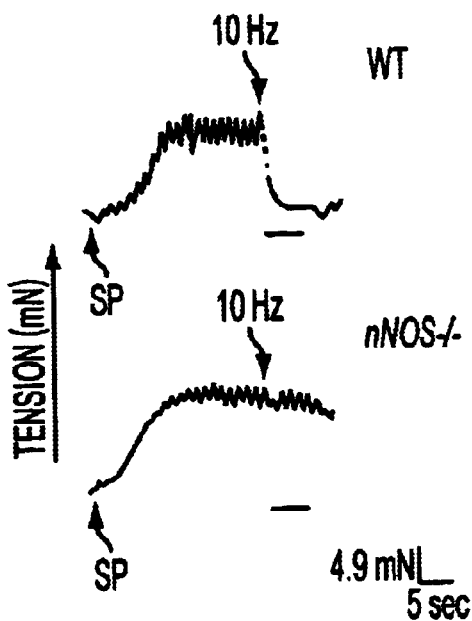
Figure 1D:
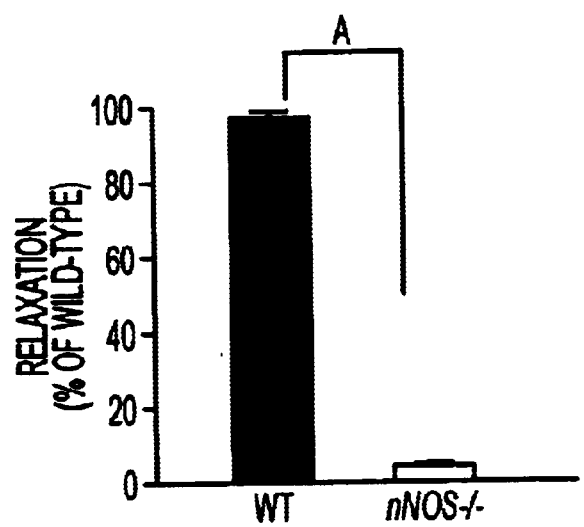

The pyloric hypertrophy and gastric dilation of nNOS$^{-/-}$ mice suggests a key role for NO in pyloric function (15). nNOS is expressed throughout the stomach, pylorus, and intestine (33–35), and all of these tissues contribute to the coordinated regulation of gastric emptying (10) in different ways. Thus, we wanted to determine the overall functional effect of genomic deletion of nNOS on gatropyloric physiology in nNOS$^{-/-}$ mice. To address this, a spectrophotometric method was adapted to measure gastric emptying of liquid meals in mice (30, 36). In these experiments, mice underwent oral-gastric intubation with a small catheter followed by instillation of a liquid containing a known quantity of phenol red. At appropriate times thereafter, the phenol red remaining in the stomach was quantified spectrophotometrically. Saline empties rapidly with at $t_{1/2}$ of 8 minutes, whereas 10% and 20% dextrose empty more slowly ($t_{1/2}$=24 and 32 minutes for 10% and 20% dextrose, respectively), reflecting a normal physiological slowing of gastric emptying in response to increased caloric load (FIG. 1a). In nNOS$^{-/-}$ mice, a substantial delay was observed in gastric emptying for saline ($t_{1/2}$=34 minutes), 10% dextrose ($t_{1/2}$=50 minutes), and 20% dextrose ($t_{1/2}$=75 minutes, FIG. 1b). Thus, gastric emptying is delayed in nNOS$^{-/-}$ mice, consistent with a key role for nNOS in gastric emptying.

Because localized pyloric contractions can obstruct gastric outflow (9, 10), impaired pyloric relaxation may account for delayed gastric emptying in nNOS$^{-/-}$ mice. To assess this possibility, we used ex vivo organ bath preparations of mouse pylori. nNOS$^{-/-}$ pylori have normal responses to acetylcholine (Ach), substance P (SP), and sodium nitroprusside (SNP), suggesting that smooth muscle function is not affected by loss of nNOS. Under NANC conditions, pylori were precontracted with 0.1 micromolar SP, and NO-dependent relaxation was elicited by electrical field stimulation. Wild-type pylori demonstrate substantial NANC relaxation in response to EFS (FIGS. 1, c and d). This relaxation is mediated by NO as it is blocked by nNOS inhibitors, including 0.1 mM L-NNA and 0.1 mM. Under the same conditions, NANC relaxation is nearly abolished in nNOS$^{-/-}$ pylori (FIGS. 1, c and d). EFS-induced relaxations in wild-type pylori are completely blocked by 0.1 micromolar TTX, consistent with a neuronal source of NO. These results suggest that nNOS-derived NO accounts for NANC relaxation in the pylorus and that loss of NO-mediated NANC relaxation causes delayed gastric emptying.

FIG. 1 is explained in more detail as follows: nNOS$^{-/-}$ mice have delayed gastric emptying and loss of NO-dependent NANC relaxation. Gastric emptying in (a) wild-type (WT) mice and (b) nNOS$^{-/-}$ mice. As described in Methods, phenol red-labeled saline (circles), 10% dextrose (triangles), or 20% dextrose (squares) was instilled into the stomachs of groups of mice, five to ten animals for each time point. The mice were sacrificed at the indicated times to determine the fraction of phenol red remaining in their stomachs as a measure of gastric emptying. Individual data points represent the mean (±SEM) for five to 10 determinations at each time point derived from groups of individual mice. In some instances, the error bars are small and contained within the symbol. The delay in gastric emptying observed in response to increased caloric content is consistent with known gastric physiology and is preserved in nNOS$^{-/-}$ mice. (c) EFS-evoked NANC relaxations were monitored from wild-type and nNOS$^{-/-}$ pylori as described (see Methods). After precontraction with SP (0.1 micromolar ), wild-type pylori demonstrate relaxation (>95%) in response to EFS (40 V, 10 Hz, 5 ms pulse for duration of 5 seconds), whereas relaxation is nearly absent in nNOS$^{-/-}$ pylori (<5%). All EFS-evoked relaxations were blocked with 0.1 micromolar TTX and the nNOS inhibitors L-NNA (0.1 mM) and 7-Nt (0.1 mM). The examples shown are from a representative experiment. (d) Quantification of NANC-induced relaxations in response to EFS for wild-type and nNOS$^{-/-}$ pylori. Several pylori representing wild-type and nNOS$^{-/-}$ mice were used to quantitatively the degree of NANC relaxation in response to EFS. Data shown are the means (±SEM) if several determinations for each group of mice (n=20 for wild-type and 10 for nNOS$^{-/-}$ pylori).$^A$p, 0.01 compared with wild-type specimens.

EXAMPLE 2
Diabetic Mice Have Delayed Gastric Emptying and Decreased NO-dependent NANC Relaxation Similar to Those of nNOS$^{-/-}$ mice.

Figure 2A:
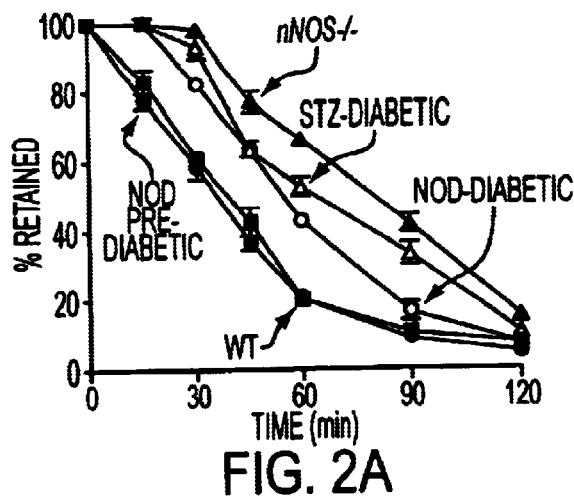
FIGS. 2A–C and 2E are graphs showing that diabetic mice have delayed gastric emptying that is not due to hyperglycemia and enlarged stomach.

The delayed gastric emptying observed in the nNOS$^{-/-}$ mice is similar to human diabetic gastropathy (4–6, 37–39). In addition, previous reports have suggested that nNOS expression may be altered in diabetic rates (25–27). To ascertain whether nNOS plays a role in diabetic gastropathy, gastropyloric function was evaluated in two models of diabetes in mice. NOD mice develop diabetes spontaneously, around 14 weeks of age, through autoimmune destruction of the pancreatic B cells (40). Thus, young NOD mice (NOD prediabetic) have normal insulin and glucose levels, although older NOD-diabetic mice have insulin-deficient diabetes. A second model of diabetes in mice uses STZ, a toxic glucose derivative selectively taken up by pancreatic B cells (29). We induced diabetes with a single injection of STZ (200 mg/kg; as discussed in Methods) and studied the gastropyloric function of the STZ-diabetic mice after 8 weeks. NOD-prediabetic mice have normal gastric emptying rates, similar to age-matched, wild-type controls, whereas gastric emptying is markedly delayed in NOD-diabetic mice (FIG. 2a). Like NOD-diabetic mice, STZ-diabetic mice have substantially delayed gastric emptying, resembling that of nNOS$^{-/-}$ mice (FIG. 2a). Thus delayed gastric emptying occurs in two distinct models of diabetes in mice.

Figure 2B:
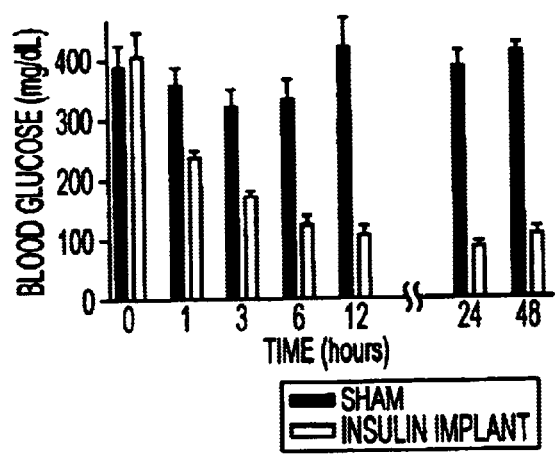
Figure 2C:
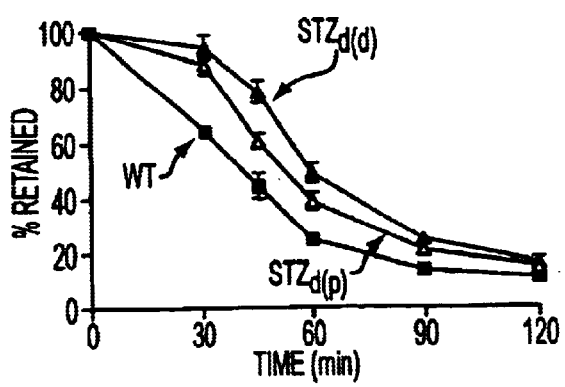
Figure 2D:
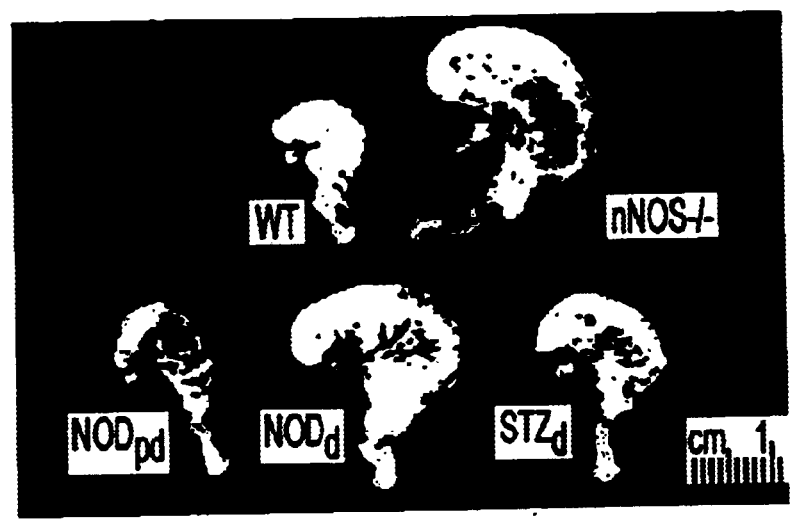
FIG. 2D is a photograph showing various wild-type and (non-obese diabetic) NOD mutant stomachs.
Figure 2E:
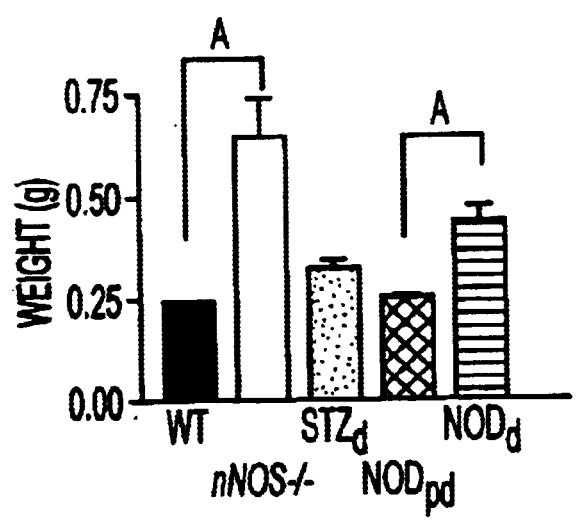

Hyperglycemia, including blood glucose levels within the normal postprandial range, can delay gastric emptying in normal and diabetic humans (41–47), although increased pyloric contractions may not contribute to delayed gastric emptying during euglycemia (48). Thus, hyperglycemia alone might explain the delay in gastric emptying observed in diabetic mice. To address this possibility, we treated STZ-diabetic animals with insulin using subcutaneous implant (see Methods) and monitored serum glucose levels. Glucose levels declined from nearly 400 mg/dL to approximately 100 mg/dL by 12 hours after insulin therapy, whereas sham-operated animals had no significant changes in their serum glucose levels (FIG. 2b). We monitored gastric emptying in sham-operated STZ-diabetic, insulin treated STZ-diabetic and wild-type mice. The $t_{1/2}$ of gastric emptying in wild-type mice is 36 minutes compared with 60 minutes for the STZ-diabetic animals (FIG. 2c). After insulin treatment for 12 hours, we find only a modest increase in the gastric emptying rate with a $t_{1/2}$ of 54 minutes (FIG. 2c). Thus hyperglycemia alone cannot account for the delayed gastric emptying observed in diabetic mice.

Given that delayed gastric emptying in nNOS$^{-/-}$ mice is associated with enlargement of the stomach, we monitored the size and weight of the stomach from mice with and without diabetes (FIGS. 2, d and e). By 30–32 weeks of age (16–18 weeks after the onset of diabetes), NOD-diabetic mice develop gastric enlargement that resembles that of the nNOS$^{-/-}$ specimens (FIG. 2d). This enlargement is reflected in the weight of the stomachs obtained from NOD-diabetic animals (FIG. 2e). The stomachs from STZ-diabetic mice (8 weeks after STZ treatment) often appear somewhat larger than wild-type specimens, but the weights of STZ-diabetic stomachs are not statistically different from those of wild-type specimens (FIGS. 2, d and e). Thus NOD-diabetic mice develop gastric enlargement after 16–18 weeks of diabetes, similar to nNOS$^{-/-}$ mice.

Figure 3A:
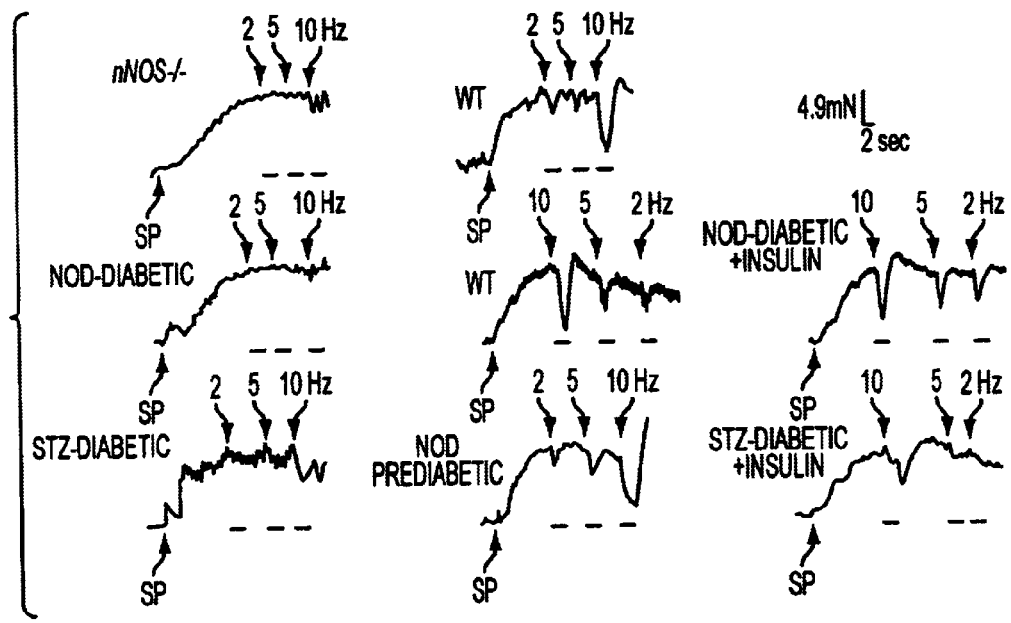
FIGS. 3A and 3B are graphs showing that pylori from diabetic mice lack NO-mediated NANC relaxation and reversal by insulin treatment.
Figure 3B:
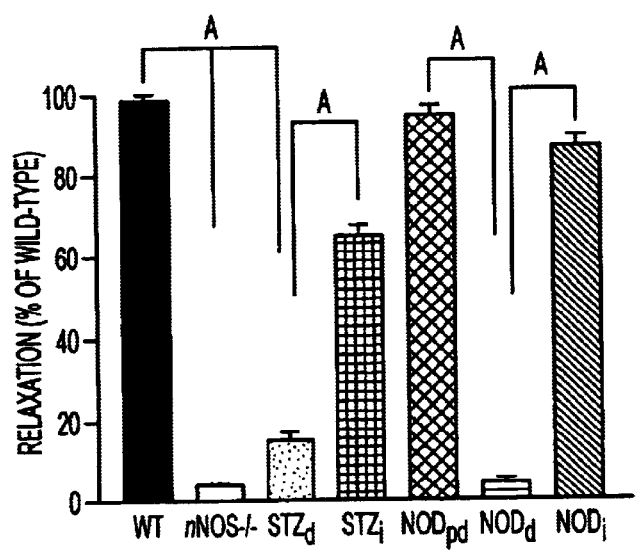

Because delayed gastric emptying in nNOS$^{-/-}$ mice reflects loss of pyloric NO-dependent NANC transmission, we monitored NO-dependant NANC transmission in pylori derived from diabetic mice using ex vivo organ bath preparations. Pylori from NOC-diabetic and STZ-diabetic have responses to SP, Ach, and SNP that resemble wild-type pylori. NNOS$^{-/-}$ pylori have a nearly complete loss of NANC relaxation at 2, 5, and 10 HZ, whereas NOD-prediabetic pylori resemble wild-type mice with maximal relaxation at 10 Hz (FIG. 3a). In contrast, NANC relaxation in NOD-diabetic and STZ-diabetic pylori is greatly reduced (FIG. 3a). To quantify the loss of NO-medicated relaxation, we analyzed data derived from the first NANC relaxation obtained in response to EFT (10 Hz) from multiple pylori representing each group of animals (FIG. 3b). Both STZ-diabetic and NOD-diabetic pylori have a dramatic reduction in NO-dependent NANC relaxation, mimicking nNOS$^{-/-}$ pylori (FIG. 3b). The data suggest that delayed gastric emptying in diabetic mice reflects a loss of NO-mediated pyloric relaxation.

FIG. 2 is explained in more detail below.

Diabetic mice have delayed gastric emptying that is not due to hyperglycermia and enlarged stomachs. (a) Gastic emptying (20% dextrose) in diabetic mice. NOD-prediabetic mice (filled circles), age 10 weeks, have gastric emptying rates similar to wild-type mice (filled squares). STZ-diabetic mice (open triangles) and NOD diabetic mice (open circles) exhibit significantly delayed gastric emptying, similar to that of nNOS$^{-/-}$ mice (filled triangles). Each data point represents the mean (±SEM) from groups of four to six animals. All diabetic animals exhibit some delay in gastric emptying, and this is reflected in the error bars (SEM) as shown. In some instances, the error bars are small and contained within the symbols. This experiment has been repeated twice with the same results. (b) Serum glucose levels of STZ-diabetic mice after insulin treatment. STZ-diabetic mice were either sham operated (n=5) or treated with subcutaneous placement of an insulin-releasing implant (n=5; see Methods). Then, serum glucose levels were determined at the indicated time points. The data shown are the means (±SEM) of five measurements for each time point. Serum glucose levels decline to around 100 mg/dL by 12 hours and remain at similar levels for 48 hours. (c) Gastric emptying in STZ-diabetic mice after 12 hours of insulin treatment. STZ-diabetic mice were either sham operated (STZd) or created with subcutaneous placement of an insulin-releasing implant ($STZ_{ds}$) 12 hours before determination of gastric emptying. The data shown are the means (±SEM) for five to seven measurements per time point. (d) Stomachs excised from wild-type, NOD-prediabetic ($NOD_{pd}$), $nNOS^{-/-}$, $NOD^-$ diabetic ($NOD_d$) and STZ-diabetic ($STZ_d$) mice were photographed to demonstrate the enlargement of the stomach in NOD-diabetic mice. The pictures are representative of five to eight specimens examined for each group of animals. (e) Stomachs from wild-type, NOD-prediabetic, $nNOS^{-/-}$, $NOD^-$diabetic and STZ-diabetic mice were weighted after fasting for 4 hours. Data shown are the means (±SEM) for five specimens in each group. The stomachs from the NOD-diabetic and $nNOS^{-/-}$ mice weighed significantly more than those from wild-type mice. $^a p<0.05$ for $nNOS^{-/-}$ stomachs compared with wild-type and for NOD-diabetics specimens compared with NOD-prediabetic.

FIG. 3 is explained in more detail as follows. Pylori from diabetic mice lack NO-medicated NANC relaxation: reversal by insulin treatment. (a) EFS-evoked NO-medicated NANC relaxations are substantially reduced at 2,5, and 10 Hz in $nNOS^{-/-}$ pylori compared with wild-type pylori. NOD-prediabetic pylori reassembled with the wild-type mice with maximal relaxation at 10 Hz. NOD-diabetic pylori have nearly absent NANC relaxation at 2, 5, and 10 Hz, resembling that of $nNOS^{-/-}$ pylori, whereas insulin treatment (1 week) of NOD-diabetic animals partially restores NANC relaxation. NANC relaxations in pylori from STZ-diabetic mice are significantly reduced, similar to pylori from $nNOS^{-/-}$ mice, and insulin treatment (1 week) of STZ-diabetic animals restores NANC relaxation. In control experiments, we compared responses of wild-type pylori to EFS stimulation as 2, 5, and 10 Hz or in the reverse order 10, 5, and 2 HZ, and we observed no apparent differences. The results shown are representative samples of five to ten pyloric preparations from different animals. (b) Quantification of NANC relaxation in response to EFS in diabetic pylori. Several pylori, representing the indicated groups of mice, were used to quantitatively analyze the degree of NANC relaxation in response to EFS. Data shown are the means (=SEM) of several determinations for each group of mice: n=10 for wild-type; n=8 for $nNOS^{-/-}$; n=5 for NOD-prediabetic; n=8 for STZ-diabetic; n=5 for insulin treated NOD-diabetic (NOD); and n=8 for insulin-treated STZ-diabetic (STZ). $^a P<0.01$ for $nNOS^{-/-}$ and STZ-diabetic compared with wild-type specimens, for NOD-diabetic compared with NOD-prediabetic specimens, for insulin-created NOD-diabetic specimens compared with NOD-diabetic specimens, and for insulin-created STZ-diabetic specimens compared with STZ-diabetic samples.

EXAMPLE 3

$nNOS^{-/-}$ protein and mRNA Expression is Lost in Diabetic Mice.

Figure 4A:
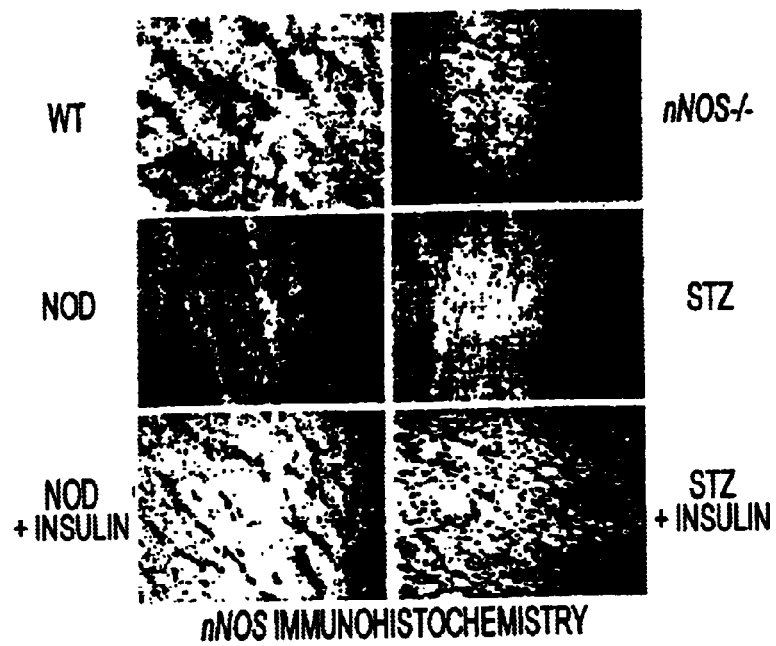
FIG. 4A is a representation of a photomicrograph showing that nNOS protein expression in the pyloric myenteric neurons is depleted in diabetic mice.
Figure 4B:
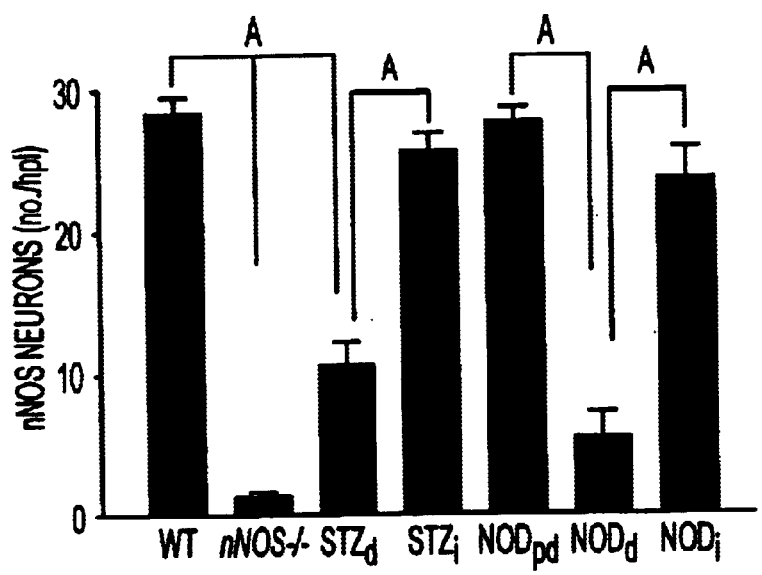
FIG. 4B is a graph showing quantification of the data shown in FIG. 4A.
Figure 5A:
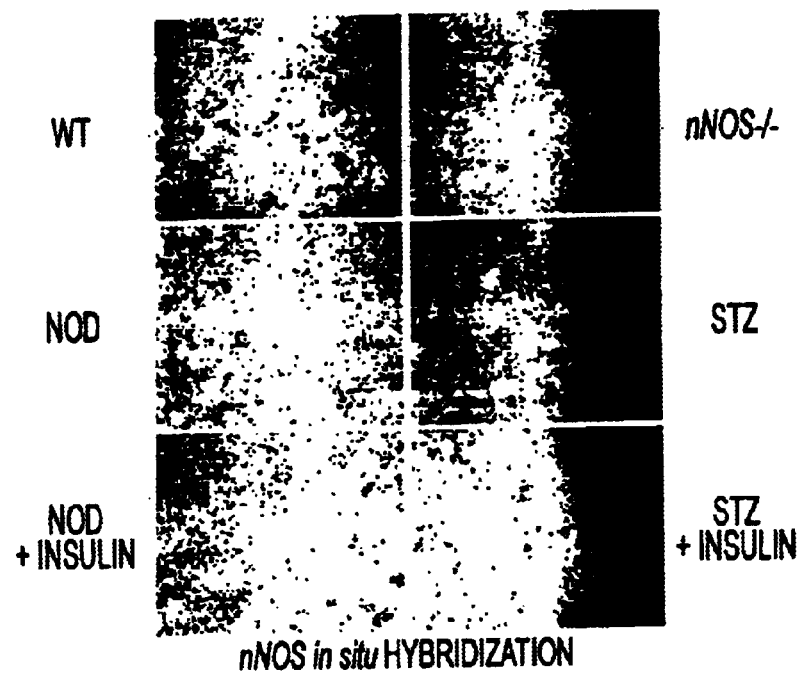
FIG. 5A is a representation of a photomicrograph showing that nNOS mRNA expression in the pyloric myenteric neurons is depleted in diabetic mice.
Figure 5B:
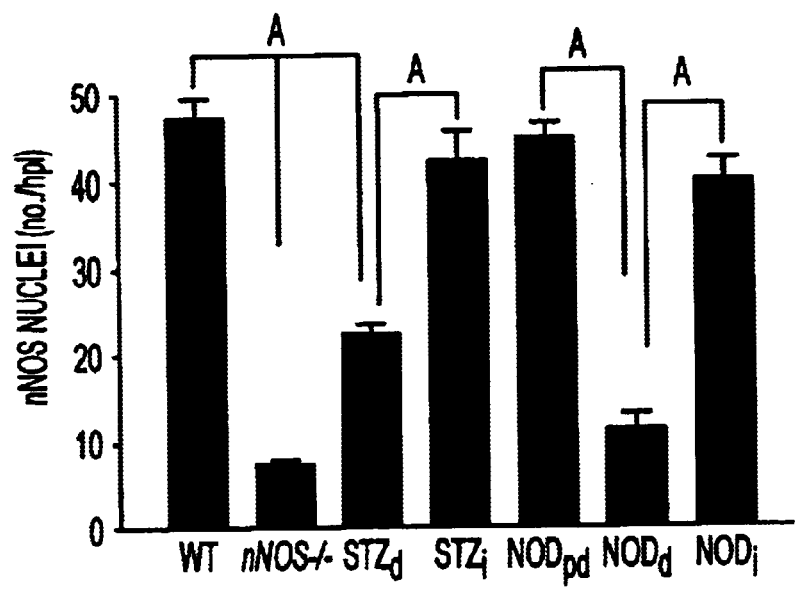
FIG. 5B is a graph showing quantification of the data shown in FIG. 5A.

Since diabetic and $nNOS^{-/-}$ mice have similar abnormal gastropyloric physiology, we wondered whether nNOS expression is altered in diabetic pylori. Thus, we examined the expression of the NNOS protein by immunohistochemistry and nNOS mRNA by in situ hybridization. Immunohistochemistry reveals discrete staining for nNOS in myenteric neurons in wild-type (FIG. 4a) and NOD-prediabetic pylon. Staining is absent in $nNOS^{-/-}$ mice (FIG. 4a), confirming the antibody's specificity. NNOS staining is nearly abolished in NOC-diabetic and substantially reduced in STZ-diabetic pylori (FIG. 4a). To quantify these changes, we determined the number of nNOS-positive neurons per high power field (hpf). NNOS-positive neurons are reduced about 65% in the STZ-diabetic pylori and by about 80% in the NOD-diabetic mice (FIG. 4b). In situ-hybridization reveals markedly decreased nNOS mRNA expression in $nNOS^{-/-}$, NOD-diabetic, and STZ-diabetic pylori (FIG. 5a(. nNOS-positive nuclei are reduced by 78% in NOD-diabetic pylori and by 53% in STZ-diabetic pylori (FIG. 5b).

FIG. 4 is explained in more detail as follows. NNOS protein expression in the pyloric myenteric neurons is depleted in diabetic mice: reversal by insulin treatment. (a) Immunohistochemical analysis of NNOS protein expression. nNOS is present in wild-type but not $nNOS^{-/-}$ pyloric myenteric neurons, whereas NNOS expression is lost in both NOD-diabetic and STZ-diabetic mice. Insulin treatment (1 week) of NOD-diabetic and STZ-diabetic animals reverse the loss of nNOS expression. (b) Quantification of NNOS protein expression. The number of nNOS-expressing neurons per hpg (×40) was determined, for ten microscopic fields, for each group of animals, with SEM as shown by the error bars. These results have been obtained in two separate experiments with four to six mice per group. $^{\wedge}P<0.01$ for $nNOS^{-/-}$ and STZ-diabetic samples compared with wild-type samples, for NOD-diabetic compared with NOD-prediabetic samples, for insulin-treated NOD-diabetic compared with NOD-diabetic samples, and for insulin-treated STZ-diabetic compared with STZ-diabetic specimens.

Figure 6:
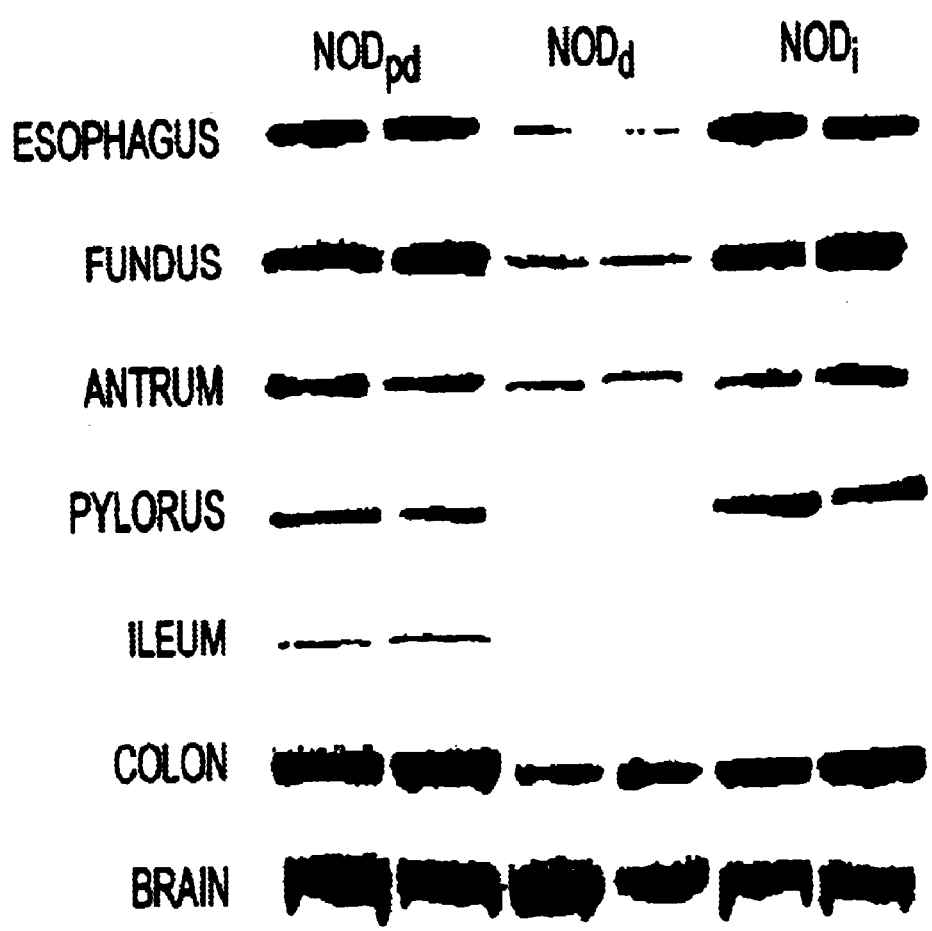
FIG. 6 is a representation of a Western immunoblot showing that nNOS protein is depleted throughout the intestine of NOD mice and reversal by insulin.

To ascertain whether the diabetes-induced depletion of nNOS expression is unique to the pylorus or is a general feature of all intestinal tissues, we monitored NNOS expression by Western bloc in various intestinal tissues derived from NOD-prediabetic, NOD-diabetic, and insulin-treated NOD-diabetic mice (FIG. 6). We find a pronounced depletion of NNOS in the pylorus, esophagus, and ileum (FIG. 6). In the antrum and body (fundus) of the stomach, we find a partial depletion of nNOS expression in NOD-diabetic tissues (FIG. 6), consistent with previous reports in diabetic rats (26, 27). A partial depletion of nNOS is also observed in the colon (FIG. 6). We find no change in the expression of nNOS in the brain, suggestion that the depletion of NNOS in diabetes may be specific to the enteric nervous system (ENS). Thus, in diabetic mice, downregulation of nNOS occurs throughout the intestine, but is most pronounced in the pylorus, esophagus, and ileum.

Figure 7:
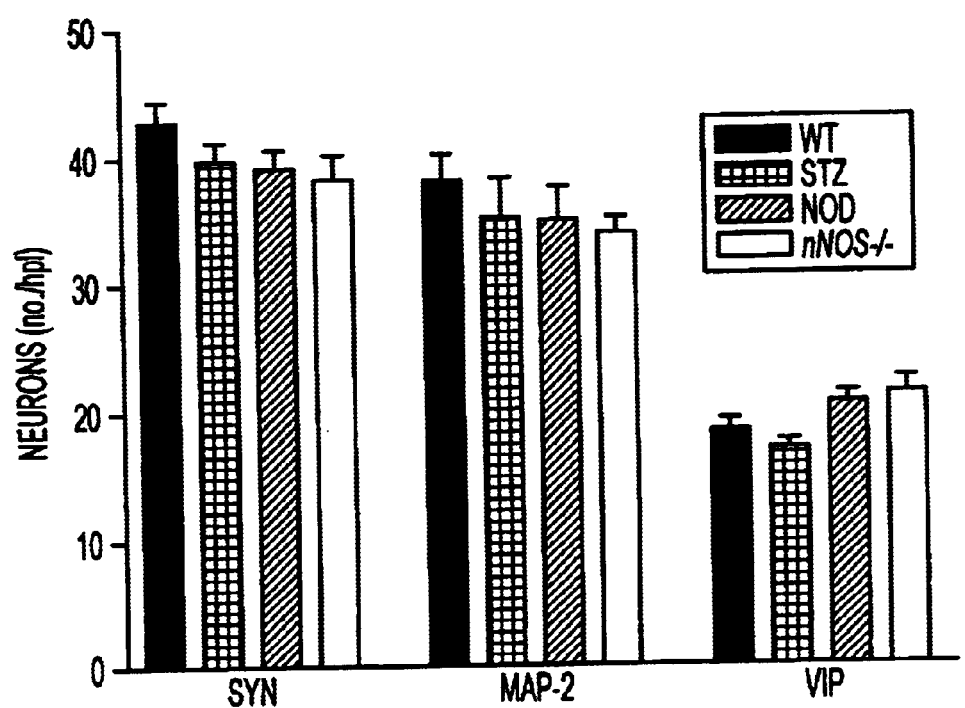
FIG. 7 is a graph illustrating that pylori of diabetic mice have a loss of nNOS expression without a loss of neurons.

Decreased nNOS protein and mRNA levels may reflect changes in NNOS expression or result form loss of the neurons that express nNOS. To determine whether loss of enteric neurons accounts for the decrease in nNOS immunoreactive neurons, we stained pyloric samples using antibodies to the neuronal markers, synaptophysin (SYN), microtubule-associated protein-2 (MAP-2), and neurofilament (NF; data not shown). MAP-2 and SYN immunoreactivity are not altered in $nNOS^{-/-}$; NOD-diabetic, or STZ-diabetic pylori, indicating that neuronal loss does not account for depletion of nNOS expression (FIG. 7). We also monitored vasoactive intestinal peptide (VIP) expression, as VIP and nNOS may colocalize within myenteric neurons (49–50). VIP staining is preserved in both NOD-diabetic and STZ-diabetic pylori (FIG. 7). These data indicate that the diminished NNOS does not reflect loss of myenteric neurons.

Figure 8:
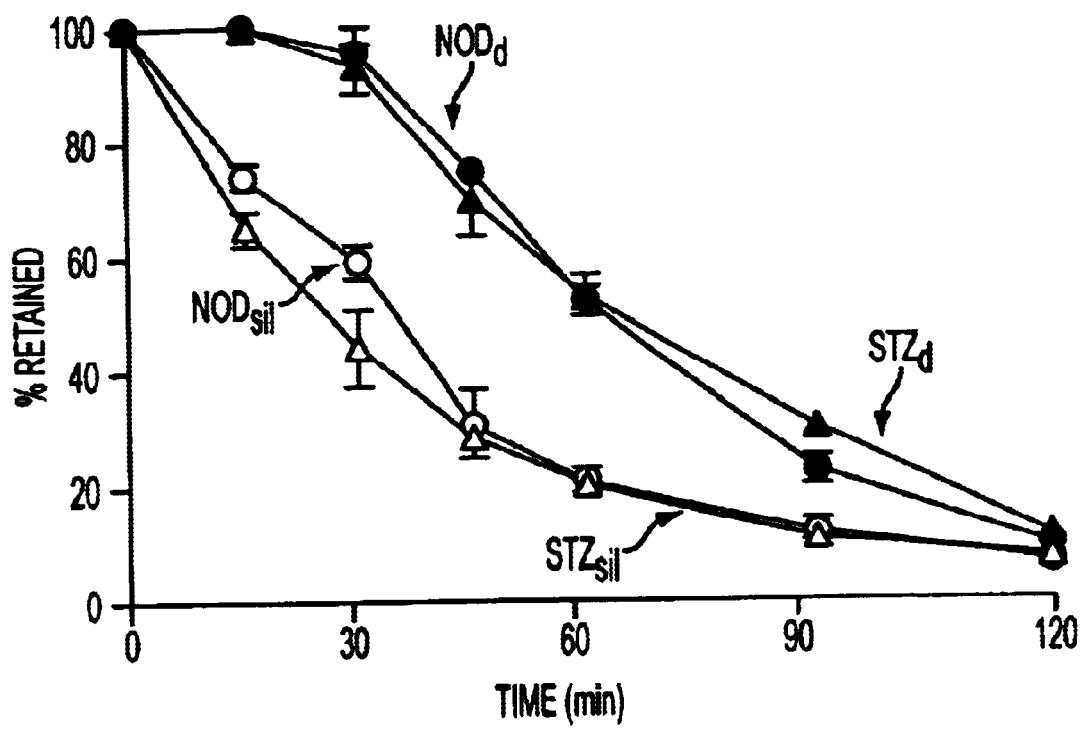
FIG. 8 is a graph showing that type 5 phosphodiesterase (PDE5) inhibition reverses delayed gastric emptying in diabetic mice.

Sildenafil reverses delayed gastric emptying in diabetic mice. Conceivably, the expression of several proteins is reduced by the insulin depletion that occurs in diabetic animals. NNOS mediates smooth muscle relaxation through the activation of cGMP production by soluble guanylate cyclase in smooth muscle cells. Some disorders of NO-dependant smooth muscle relaxation, such as impotence, can be treated by inhibition of the cGMP specific phosphodiesterase-5 (PDE5) that breaks down cGMP (52, 53). To determine whether the loss of NNOS accounts for delayed gastric emptying, we used sildenafil. This was used because the PDE5 is enriched in the pylorus (54). Inhibition of PDE5 allows the accumulation of cGMP in the presence of lower NO levels. We wondered whether treatment of diabetic animals with sildenafil would accelerate gastric emptying. Accordingly, we treated STZ-diabetic and NOD-diabetic mice with sildenafil (1 mg/kg) and monitored gastric emptying. Sildenafil reverses the delayed gastric emptying of both STZ-diabetic and NOD-diabetic mice with the $t_{1/2}$ for gastric emptying of 30 and 36 minutes for sildenafil-treated STZ-diabetic and sildenafil-treated NOD-diabetic animals, respectively (FIG. 8). These data implicate impaired NO signaling as the mechanism through which delayed gastric emptying develops in diabetic mice.

FIG. 5 is explained below.

nNOS mRNA expression in the pyloric myenteric neurons is depleted in diabetic mice: reversal by insulin treatment (a) In situ hybridization analysis of NNOS expression. nNOS mRNA expression is present in wild-type and depleted nNOS pyloric myenteric neurons where as NNOS mRNA expression is significantly decreased in both NOD-diabetic and STZ-diabetic mice. (b) Quantification of NNOS mRNA expression. The number of positive nuclei for NNOS mRNA per hpf was determined for ten microscopic fields, for each treatment group, with SEM as shown by the error bars. These results have been obtained in two separate experiments with four to six mice per-group. $P<0.01$ for nNOS$^{-/-}$ and STZ-diabetic samples compared with wild-type samples, for insulin-treated NOD-diabetic compared with NOD-diabetic samples, and for insulin treated STZ-diabetic compared with STZ diabetic specimens.

FIG. 6 is explained in more detail as follows. nNOS protein is depleted throughout the intestines in NOD mice: reversal by insulin. Western blot analysis of nNOS protein expression was performed using samples from several regions of intestine derived from NOD-prediabetic, NOD-diabetic, and insulin-treated NOD-diabetic mice. nNOS protein is nearly completely depleted in the pylorus, esophagus, and ileum, with only partial depletion in other intestinal regions. There is no apparent change in nNOS expression in the brain. Insulin treatment (1 week) completely reverses the loss of nNOS protein. The results are shown in duplicate and are representative of six animals for each group.

FIG. 7 is explained more fully as follows. Pylori of diabetic mice have a loss of nNOS expression without a loss of neurons. Myenteric neurons were quantified by counting the number of positive neurons per hpf. No change in expression of SYN, MAP2, or BIP was observed for with STZ-diabetic or NOD-diabetic mice. The data shown are the means (=SEM) of determinations form at least ten microscopic fields, with the experimenter blinded to the treatment condition of the animals from which the histological sections were derived.

FIG. 8 is explained in more detail as follows. PDE5 inhibition reverses delayed gastric emptying in diabetic mice. NOD-diabetic and STZ-diabetic mice were treated with sildenafil (sf), as described in Methods, 20 minutes before determining gastric emptying. The data shown are means (=SEM) of quadruplicate determinations representing four animals for each data point. Sildenafil treatment of diabetic animals reveres delayed gastric emptying in diabetic animals.

EXAMPLE 4 nNOS Expression and NO-dependent NANC Relaxation are Restored by Insulin Treatment.

Figure 9A:
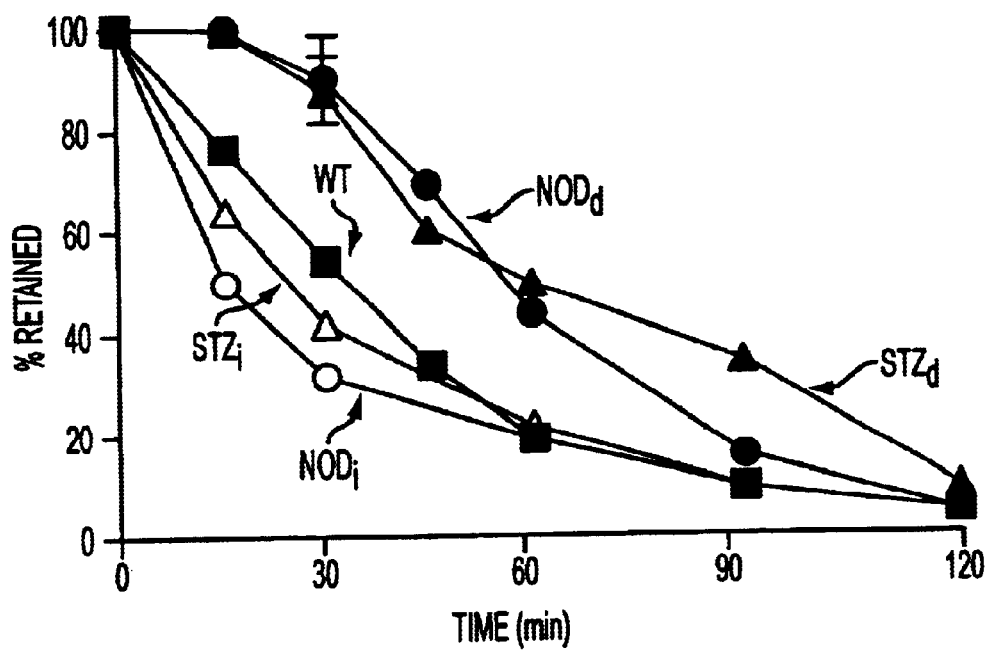
FIGS. 9A and 9B are graphs showing that insulin treatment reverses delayed gastric emptying.

Both NOD-diabetic and STZ-diabetic mice have elevated serum glucose with low insulin levels. We corrected these abnormalities by treatment with an implantable insulin device (Table 1). After 1 week of insulin treatment, gastric emptying in both NOD-diabetic and STZ-diabetic mice is restored to normal (FIG. 9a). Insulin treatment also restores EFS-induced NANC relaxation in pylori from insulin-treated NOD-diabetic or STZ-diabetic animals (FIGS. 3, b and c). The restorative effect of insulin on EFS-induced relaxations from insulin-treated NOD-diabetic pylori was greater than that observed in insulin-treated STZ-diabetic pylori. This finding may reflect the more dramatic loss of NNOS expression observed in the NOD-diabetic mice (FIGS. 4b and 5b).

Figure 9B:
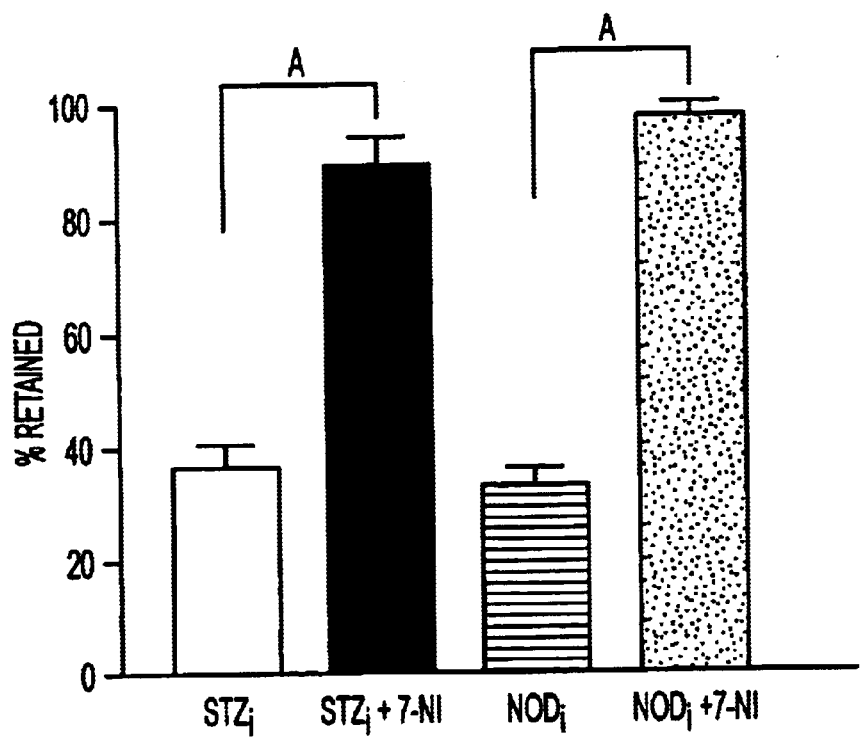

Insulin treatment is likely to alter the expression of numerous genes. To determine whether the induction of nNOS expression mediates the effect of insulin on gastric emptying, we monitored gastric emptying at 30 minutes in insulin-treated STZ-diabetic and insulin-treated NOD-diabetic mice after administration of the nNOS inhibitor 7-NI. 7-NI reverses the restoration of normal gastric emptying in insulin-treated diabetic mice (FIG. 9b), indicating that nNOS caralyric activity mediates the effect of insulin treatment on gastric emptying. As insulin restores NANC relaxation in diabetic pylori, we tested NANC relaxation in the presence of 0.1 mM 7-NI. Under these conditions, NANC relaxation is completely blocked, indicating that nNOS expression also accounts for restorative effects of insulin on pyloric relaxation.

Insulin treatment returns NNOS protein expression in NOD-diabetic and STZ-diabetic pylori to near normal levels (FIGS. 4, a and b). In situ hybridization reveals that insulin treatment also substantially restores NNOS mRNA in both NOD-diabetic and STZ-diabetic pylori (FIGS. 5, a and b). The depletion of nNOS expression throughout the intestine is fully reversible by insulin, although diabetes induces only a partial depletion of nNOS protein in some intestinal tissues (FIG. 6).

FIG. 9 is explained more fully as follows. Insulin treatment reverses delayed gastric emptying. (a) Insulin treatment (1 week) of STZ-diabetic and NOD-diabetic mice reverses delayed gastric emptying (20% dextrose). The data shown are the means (=SEM) of quadruplicate determinations representing four animals for each data point. (b) Inhibition of nNOS with 7-NI delays gastric emptying in insulin-treated diabetic mice. Diabetic mice were treated with insulin (1 week) and subsequently treated with the nNOS inhibitor 7-NI (50 mg/kg) as described in Methods. Gastric emptying was measured, and mice were sacrificed at 30 minutes. Data shown are means (=SEM) of five determinations reflecting five animals in each group. $P<0.01$ for 7-NI-injected, insulin-treated NOD-diabetic animals compared with insulin-treated NOD-diabetic mice and for 7-NI-injected, insulin-treated STZ-diabetic animals compared with insulin treated STZ-diabetic animals.

The following Materials and Methods were employed, as needed, in the foregoing Examples 1–4.

Animals. Mice were allowed free access to food and water except when fasted, as indicated for experiments. The weights and serum glucose levels of groups of animals used for experiments are given in Table 1. Wild-type mice (C57BL/6) were purchased from The Jackson Laboratory (Bar Harbor, Me., USA). nNOS$^{-/-}$ mice were obtained following targeted genomic deletion of nNOS (15) and have the genetic background of C57BL/6 mice (28). For STZ-induced diabetes, adult male mice (C57BL/6) were injected intraperitoneally with a single dose of STZ (200 mg/kg in 0.1 M sodium citrate) as described elsewhere (29), whereas control mice were injected with an equal volume of vehicle (sodium citrate). STZ-treated mice were used for experiments 8 weeks after STZ injection. After STZ treatment, serum glucose levels were monitored weekly by tail vein sampling of animals fasted for 12 hours with the Accu-Check Easy Blood Glucose Monitor (model 788; Boehringer Mannheim, Indianapolis, Ind., USA). The average serum glucose levels for wild-type animals and the STZ diabetic mice 8 weeks after injection were 99 mg/dL and 388 mg/dL, respectively (Table 1). Adult male nonobese diabetic (NOD/LtJ [NOD]) mice were obtained at 8–10 weeks of age (The Jackson Laboratory). Serum glucose levels were also monitored weekly with the Accu-Check monitor. NOD-prediabetic mice and NOD-diabetic mice had average serum glucose levels of 88 mg/dL and 232 mg/dL, respectively (Table 1). For the indicated experiments, NOD-prediabetic mice were sacrificed at 10 weeks of age after serum glucose levels were confirmed, whereas NOD-diabetic mice were sacrificed at 30–32 weeks of age after elevated serum glucose levels were confirmed.

Insulin treatment was given using LinBit, a sustained-release insulin implant (0.1 U/d/implant; LinShin Canada Inc., Toronto, Ontario, Canada). After brief anesthesia with diethyl ether, the insulin implant was quickly immersed in Betadine solution (McKesson, San Francisco, Calif., USA) and implanted subcutaneously with a 12-gauge needle. Serum glucose levels were monitored, and insulin-treated animals were used for experiments after 12 hours or 1 week of insulin therapy, as indicated. The serum glucose levels after 1 week of insulin treatment are shown (Table 1), as are the serum glucose levels after 12 hours of insulin treatment (see FIG. 2b).

As indicated, insulin-treated diabetic mice were treated with the nNOS inhibitor 7-nitroindazole (7-NI; Lancaster, Wyndham, N.H., USA) by two intraperitoneal injections (50 mg/kg) of a suspension in sesame oil (Sigma Chemical Co., St. Louis, Miss., USA) given 24 hours and 30 minutes before determination of gastric emptying. In other experiments, NOD-diabetic and STZ-diabetic mice were treated with sildenafil (1 mg/kg in water; Pfizer, Groton, Conn., USA) by intraperitoneal injection 20 minutes before determination of gastric emptying. For all experiments, control animals were similarly injected with vehicle (either sesame oil or water).

Gastric emptying. Gastric emptying of liquids was determined as described previously (30). For any experiments using diabetic mice, serum glucose levels of all animals were confirmed immediately before monitoring gastric emptying. Adult mice were sedated briefly (<30 seconds) with diethyl ether. Mice fully recovered from sedation in less than 1 minute. During brief sedation, oral-gastric intubation was accomplished with a 21-gauge needle fitted with a thin plastic catheter (8 cm in length). Then, 0.2 mL of 1 mg/mL phenol red-labeled 20% dextrose (or other solution, if indicated) was instilled into the stomach. Mice were placed in clean, empty cages until the time of sacrifice. At the indicated time (0–120 minutes), mice were rapidly sacrificed by cervical dislocation and the stomach was excised. The duodenum was ligated, followed by transverse resection of the lower esophagus, and the stomach was removed from the body cavity. Excised stomachs were homogenized with a polytron (Brinkmann, Westbury, N.Y., USA) homogenizer in 3 mL of 95% ethyl alcohol. After centrifugation (40,000 g for 20 minutes), an aliquot of the supernatant was used to determine phenol red content. Standard curve was constructed and found to be linear over the range of 1–20 microgram of phenol red. Phenol red content was monitored at 410 nm, at which a single peak of absorbance was observed when extracted with ethanol. Thus, gastric emptying data are presented as the percent of phenol red retained, which is calculated as the mean (±SEM) of several measurements from several animals for each time point as indicated in the figure legends. The time required to empty 50% of the phenol red containing meal (half-time [$t_{1/2}$]) was derived directly from the graphed data.

Organ bath physiology. Mice were sacrificed by cervical dislocation, and the gastrointestinal tract from the lower esophageal sphincter to the distal duodenum was removed from the body cavity and placed in Ca$^2$-free Krebs-Henseleit (KH) buffer. The pyloric sphincter muscle was dissected in Ca$^2$-free KH and mounted between two L-shaped tissue hooks. The ex vivo preparations were then placed in 25-nL chambers containing KH buffer (Sigma Chemical Co.) at 37° C. and continuously bubbled with 95% $O_2$, 5% $CO_2$. Tension was monitored with an isometric force transducer and recorded with a chart recorder. For routine experiments, pylori were equilibrated in KH buffer for 1 hours with 4.9 mN of tension applied. Then, pylori were pretreated with atropine (1.0 micromolar, propanolol (1.0 micromolar), and indomethatin (10.0 micromolar) for 30 minutes to block cholinergic-, adrenergic-, and prostaglandin-mediated responses, respectively. Ex vivo preparations of pylori have regular phasic contractions but do not develop significant spontaneous tone (tonic contraction) that would allow the direct measurement of relaxation. Thus, precontraction of the pyloric muscles with substance P(SP) was used to generate tonic muscle contraction and allow the measurement of relaxation. Pylori were contracted with 0.1 micromolar SP, and those specimens demonstrating a sustained tonic contraction were used for experiments. NANC relaxations were induced 10–20 seconds after contraction with SP by electrical field stimulation (ET S; 40 V, 2–10 Hz, 5 ms pulse for a duration of 5 or 2 seconds, as indicated). For quantitative determination of relaxation, we used several pylori from any given treatment condition, as indicated in the figure legends, and used the relaxation obtained from the first EFS under NANC conditions. In some experiments, pylori were stimulated first with 10 Hz followed by 5 and then 2 Hz, whereas in others, the order of stimulation was reversed. In wild-type pylori, responses to EFS were similar regardless of the order of stimulation. In other experiments, we observed similar responses to 2,5 or 10 Hz given as single stimuli after SP contraction. To confirm the role of neuronal depolarization in evoking NANC relaxations, retrodotoxin (TTX; 0.1 micromolar; Research Biochemical, Natick, Mass., USA) was used. The NO dependence of NANC relaxation was confirmed by incubation with either 0.1 mM N-nitro-[.-arginine (L-NNA; Sigma Chemical Co.) or 0.1 mM 7-NI for 30 minutes before EFS.

Immunohistochemistry. For nondiabetic studies, wild-type animals or 10-week-old NOD-prediabetic animals were used. For diabetic studies, we used animals 8 weeks after STZ injection (STZ diabetic) or 30-week-old NOD mice (NOD-diabetic). Pylori or other tissues were dissected and immediately imbedded (Tissue-Tek OCT 4583; Sakura Finetek Inc., Torrence, Calif., USA) and placed in dry ice and allowed to freeze. Routine sections (10 micrometer) were cut using a cryostat (−19° C.; Leica Microm, Allendale, N.J., USA). For immunostaining, slides were fixed for 5 minutes in 4.0% paraformaldehyde, washed in PBS, and permeablized with 0.1% Triton X-100 in PBS. Then, slides were incubated overnight at 4° C. with primary antibodies as indicated; anti-nNOS (1:8, 000; DiaSorin, Stillwater, Minn., USA), anti-synaptophysin (1:500; Sigma Chemical Co.), anti-VIP (1:4,000; Calbiochem-Nov-abiochem Corp., San Diego, Calif., USA), and anti-Map-Z (1:200; Boehringer Mannheim). The antigens were visualized using the appropriate secondary antibodies and the Vectastain ABC kit (Vector Laboratories, Burlingame, Calif., USA).

In situ hybridization. In situ hybridization for nNOS was performed as described previously (31,32).

Western blot analysis. Mouse tissues were homogenized in ice-cold buffer containing 50 mM Tris (pH 7.4, 25° C.), 100 mM NaCl, 1 mM EGTA, and protease inhibitors (4 microgram/mL leupeptin, 2 microgram/mL antipain, 2 microgram/mL pepstatin, and 1 mM PMSF). After centrifugatin (1.5 minutes, 16,000 g), the supernatants were collected and protein content was determined (Coomassie protein assay; Pierce Chemical Co., Rockville, Ill., USA). Samples (50 microgram protein) were subjected to SDS-PAGE (4–12% gradient gel; Bis-tris NuPage; Novex, San Diego, Calif., USA) and then transferred to PVDF membranes (Immobilon-P; Millipore Corp., Bedford, Mass., USA). For Western blot analysis, blots were incubated in blocking buffer (PBS, 0.1% Tween-20, 5% non-fat milk) for 30 minutes at 25° C. Then, the blots were incubated in blocking buffer with primary antibody (anti-nNOS antibody, MAB1265; Transduction Laboratories, Lexington, Ky., USA) at a dilution of 1:1,000 for 1 hour at 25° C. with gentle agitation, followed by three 5-minute washes with blocking buffer. Blots were then incubated with secondary antibody (goat anti-mouse IgG; Amersham Life Sciences Inc., Arlington Heights, Ill., USA) at a dilution of 1:5,000 in blocking buffer for 30 minutes at 25° C., followed by three 5 minute washes with blocking buffers and then two 5-minute washes with PBS. Immunote-active proteins were visualized using enhanced chemiluminescence (Renaissance Western Blot Chemiluminescence (Renaissance Western Blot Chemiluminescence Reagent Plus; NEN Life Science Products Inc., Boston, Mass., USA).

Statistical analysis. Data were analyzed using GraphPad Prism software (version 2.01; GraphPad Software Inc., San Diego, Calif., USA). Significance was analyzed using a paired, two-tailed, Student's test, and, unless otherwise indicated, data are presented as mean values (±SEM). As indicated, single comparisons of groups of experimental mice were made to the appropriate control group.

Discussion

Gastoropathy is an important cause of morbidity for diabetic patients. Using two models of diabetes in mice, it has been discovered that diabetic mice develop selective depletion of NNOS protein and mRNA and delayed gastric emptying in conjunction with the loss of NO-mediated NANC neurotransmission that mimics the phenotype of mice harboring a genomic deletion of NNOS. The examples above provide data that is consistent with recent reports of decreased NNOS expression and NANC relaxation in the gastric specimens of diabetic rats (25–27).

At least two lines of evidence support NNOS deficiency as causal in diabetic gastropathy in these mouse models. First, sildenafil, a potent and selective PDE5 inhibitor that augments the effects of reduced NO levels, is able to restore gastric emptying in diabetic mice. Second, treatment of diabetic animals with insulin restores myenteric nNOS protein and mRNA, restores NO-mediated NANC neurotransmission, and reverses delayed gastric emptying. Thus delayed gastric emptying in diabetic mice results from a reversible loss of nNOS expression within myenteric neurons that can be reversed with sildenafil.

Gastric emptying results form the coordinated activity of the proximal stomach (fundus), antrum, pylorus, and duodenum (10). Loss of fundal relaxation in nNOS$^{-/-}$ or diabetic mice can accelerate gastric emptying, whereas loss of pyloric or duodenal relaxation may delay gastric emptying. In both nNOS$^{-/-}$ and diabetic mice, the loss of NNOS is associated with delayed gastric emptying consistent with a major physiological effect on pyloric function. This finding is supported by our findings of more pronounced depletion of nNOS in the pylorus compared with the fundus and antrum and with the anatomic changes observed in these animals. Interestingly, in patients with recently diagnosed diabetes, some investigators have described accelerated gastric emptying (39, 55, 56). These findings may reflect predominant loss of nNOS in the fundus or antrum in early diabetes.

Diabetic patients manifest motility disturbances in the small intestine and colon as well as the stomach (5, 6), and recent evidence suggests that NO mechanisms regulate human small intestinal motility (66). In diabetes, diarrhea may reflect diminished small intestinal motility allowing bacteria overgrowth, whereas constipation may result from poor motility in the colon. It is believed that decreased NNOS expression we observe in intestinal tissues other than the pylorus contributes to other diabetic gastrointestinal syndromes. Interestingly, diabetic gastropathy and other diabetic gastrointestinal syndromes may worsen when patients are not taking insulin or have poor glucose control associated with illness (5, 6, 67). Symptomatic improvement often follows resumption of insulin therapy or improved control of serum glucose levels. Accordingly, reversible decreases in nNOS expression, as reported here, may underlie the relapsing and remitting clinical course associated with diabetic gastrointestinal syndromes.

Other gastrointestinal disorders, unrelated to diabetes, may also result from dysregulation of nNOS in myenteric neurons. For example, pylori from infants with hypertrophic pyloric stenosis display a selective loss of NNOS (16, 17). In this condition, loss of nNOS leads to pyloric hypertrophy and complete blockade of gastric emptying. In the esophagus, loss of nNOS expressing neurons is associated with dysfunction of the lower esophageal sphincter resulting in achalasia (68–78). Functional bowel disorders, including irritable bowl syndrome and functional dyspepsia, affect a large group of patients who may have motility disturbances (71, 72). Recent reports suggest that delayed gastric emptying is common in these patients (73, 74).

The examples shown above have therapeutic implications. Currently, the major drugs used in treating diabetic gastropathy include domperidone, metoclopramide, cisapride, and erythomycin (5,6). These drugs act by increasing stomach contractions. Their limited clinical utility may reflect the finding that abnormalities in diabetic gastropathy are primarily in the NANC relaxation rather than the contractile component of gastopyloric function. Drugs that enhance the effect of NO, or of its effector, cGMP, would presumably cause pyloric relaxation. We found that treatment for diabetic mice with the PDE5 inhibitor sildenafil reverses delayed gastric emptying. This finding is consistent with a recent study demonstrating enrichment of PDE5 in the pylorus (54). Interestingly, a recent report suggest that sildenafil can inhibit esophageal motility in patients with achalasia (74). Thus, PDE5-selective inhibitors, such as sildenafil, will be effective in the treatment of diabetic gastropathy and related conditions.

Accordingly, an in one aspect, the invention provides useful methods for preventing or treating Gastrointestinal dysfunctions common in diabetic patients. In genetic (nonobese diabetic) and toxin-elicited (streptozotoein) models of diabetics in mice, the results described herein demonstrate defects in gastric emptying and nonadrenergie, noncholinergic relaxation of pyloric muscle, which resemble defects in mice harboring a deletion of the neuronal nitric oxide synthase gene (nNO5). The diabetic mice manifest pronounced reduction in pyloric NNOS protein and mRNA. The decline of NNOS in diabetic mice does not result from loss of myenteric neurons. nNOS expression and pyloric function are restored to normal levels by insulin treatment. Thus diabetic gastropathy in mice reflects an insulin-sensitive reversible loss of nNOS. In diabetic animals, delayed gastric emptying can be reversed with a phosphodiesterase inhibitor, sildenafil. The invention has important therapeutic use and may help clarify the etiology of diabetic gastropathy.

The following specific references, also incorporated by reference, are indicated in the examples and discussion above by a number in parentheses.

1. Porte, D., Jr., and Halter, J. B. 1999. The clinical syndrome of diabetes mellitus. In *Diabetic neuropathy*. P. J. Dyck and P. K. Thomas, editors. W. B. Saunders Co. Philadelphia, Pa., USA. 1–28.

2. Foster, D. W. 1998. Diabetes mellitus. In *Harrison's principles of internal medicine*. A. S. Fauci et al., editors. McGraw-Hill. New York, N.Y., USA. 2060–2081.

3. Feldman, M., and Schiller, L. R. 1983. Disorders of gastrointestinal motility associated with diabetes mellitus. *Ann. Intern. Med.* 98:378–384.

4. Abrahamsson, H. 1995. Gastrointestinal motility disorders in patients with diabetes mellitus. *J. Intern. Med.* 237:403–409.

5. Koch, K. L. 1999. Diabetic gastropathy: gastric neuromuscular dysfunction in diabetes mellitus: a review of symptoms, pathophysiology, and treatment. *Dig. Dis. Sci.* 44:1061–1075.

6. Verne, G. N., and Sninsky, C. A. 1998. Diabetes and the gastrointestinal tract. *Gastroenterol. Clin. North Am.* 27:861–874.

7. Kassander, P. 1958. Asymptomatic gastric retention in diabetes (gastroparesis diabeticorum). *Ann. Intern. Med.* 48:797–812.

8. Hoogerwerf, W. A., Pasricha, P. J., Kalloo, A. N., and Schuster, M. M. 1999. Pain: the overlooked symptom in gastroparesis. *Am. J. Gastroenterol.* 94:1029–1033.

9. Tougas, G., et al. 1992. Relation of pyloric motility to pyloric opening and closure in healthy subjects. *Gut.* 33:466–171.

10. Horowitz, M., Dent, J., Fraser, R., Sun, W., and Hebbard, G. 1994. Role and integration of mechanisms controlling gastric emptying. *Dig. Dis. Sci.* 39 (Suppl.):7S-13S.

11. Mearin, F., Camilleri, M., and Malagelada, J. R. 1986. Pyloric dysfunction in diabetics with recurrent nausea and vomiting. *Gastroenterology.* 90:1919–1925.

12. Tomita, R., Tanjoh, K., Fujisaki, S., and Fukuzawa, M. 1999. The role of nitric oxide (NO) in the huma pyloric sphincter. *Hepatogastroenterology.* 46:2999–3003.

13. Stark, M. E., and Szurszewski, J. H. 1992. role of nitric oxide in gastrointestinal and hepatic function and disease. *Gastroenterology.* 103:1928–1949.

14. Bult, H., et al. 1990. Nitric oxide as in inhibitory non-adrenergic noncholinergic neurotransmitter. *Nature.* 345:346–347.

15. Huang, P. L., Dawson, T. M., Bredt, D. S., Snyder, S. H., and Fishman, M. C. 1993. Targeted disruption of the neuronal nitric oxide synthase gene. *Cell.* 75:1273–1286.

16. Vanderwinden, J. M., Mailleux, P., Schiffmann, S. N., Vanderhaeghen, J. J., and De Laet, M. H. 1992. Nitric oxide synthase activity in infantile hypertrophic pyloric stenosis. *N. Eng. J. Med.* 327:511–515.

17. Chung, E., et al. 1996. Genetic evidence for the neuronal nitric oxide synthase gene (NOS1) as a susceptibility locus for infantile pyloric stenosis. *Am. J. Hum. Genet.* 58:363–370.

18. Sun, W. M., et al. 1996. Effects of glyceryl trinitrate on the pyloric motor response to intraduodenal triglyceride infusion in humans. *Eur. J. Clin. Invest.* 26:657–664.

19. Sun, W. M., et al. 1998. Effects of nitroglycerin on liquid gastric emptying and antropyloroduodenal motility. *Am. J. Physiol.* 275:G1173-G1178.

20. Konturek, J. W., Thor, P., and Domschke, W. 1995. Effects of nitric oxide on antral motility and gastric emptying in humans. *Eur. J. Gastroenterol. Hepatol.* 7:97–102.

21. Konturek, J. W. Fischer, H., Gromotka, P. M., Konturek, S. J., and Domschke, W. 1999. Endogenous nitric oxide in the regulation of gastric secretory and motor activity in humans. *Aliment. Pharmacol. Ther.* 13:1683–1691.

22. Anvari, M., Paterson, C. A., and Daniel, E. E. 1998. Role of nitric oxide mechanisms in control of pyloric motility and transpyloric flow of liquids in conscious dogs. *Dig. Dis. Sci.* 43:506–512.

23. Plourde, V., Quintero, E., Suto, G., Coimbra, C., and Tache, Y. 1994. Delayed gastric emptying induced by inhibitors of nitric oxide synthase in rats. *Eur. J. Pharmacol.* 256:125–129.

24. Orihata, M., and Sarna, S. K. 1994. Inhibition of nitric oxide synthase delays gastric emptying of solid meals. *J. Pharmacol. Exp. Ther.* 271:660–670.

25. Jenkinson, K. M., and Reid, J. J. 1995. Effect of diabetes on relaxations to non-adrenergic, non-cholinergic nerve stimulation in longitudinal muscle of the rat gastric fundus. *Br. J. Pharmacol.* 116:1551–1556.

26. Wrzos, H. F., Cruz, A., Polavarapu, R., Shearer, D., and Ouyang, A. 1997. Nitric oxide synthase (NOS) expression in the myenteric plexus of streptozotocin-diabetic rats. *Dig. Dis. Sci.* 42:2106–2110.

27. Takahashi, T., Nakamura, K., Itoh, H. Sima, A. A., and Owyang, C. 1997. Impaired expression of nitric oxide synthase in the gastric myenteric plexus of spontaneously diabetic rats. *Gastroenterology.* 113:1535–1544.

28. Agarwal, M. K. 1980. Streptozotocin: mechanisms of action: proceedings of a workshop held on Jun. 21, 1980, Washington, D.C. *FEBS Lett.* 120:1–3.

29. Kuo, W. H., Wadwa, K. S., and Ferris, C. D. 1998. Cephalosporin antibiotics accelerate gastric emptying in mice. *Dig. Dis. Sci.* 43:1690–1694.

30. Schaeren-Wiemers, N., and Gerfin-Moser, A. 1993. A single protocol to detect transcripts of various types and expression levels in neural tissue and cultured cells: in situ hybridization using digoxigenin-labelled cRNA probes. *Histochemistry.* 100:431–440.

31. Eliasson, M. J., Blackshaw, S., Schell, M. J., and Snyder, S. H. 1997. Neuronal nitric oxide synthase alternatively spliced forms: prominent functional localizations in the brain. *Proc. Natl. Acad. Sci. USA.* 94:3396–3401.

32. Mashimo, H., He, X. D., Huang, P. L., Fishman, M. C., and Goyal, R. K. 1996. Neuronal constitutive nitric oxide synthase is involved in murine enteric inhibitory neurotransmission. *J. Clin. Invest.* 98:8–13.

33. Li, C. G., and Rand, M. J. 1990. Nitric oxide and vasoactive intestinal polypeptide mediate non-adrenergic, non-cholinergic inhibitory transmission to smooth muscle of the rat gastric fundus. *Eur. J. Pharmacol.* 191:303–309.

34. Lefebvre, R. A., Smits, G. J., and Timmermans, J. P. 1995. Study of NO and VIP as non-adrenergic non-cholinergic neurotransmitters in the pig gastric fundus. *Br. J. Parmacol.* 116:2017–2026.

35. Grunewald, K. K., and Tucker, T. J. 1985. Gastric emptying in exercised mice. *Comp. Biochem. Physiol. A.* 80:173–175.

36. Horowitz, M., et al. 1991. Relationships between oesophageal transit and solid and liquid gastric emptying in diabetes mellitus. *Eur. J. Nucl. Med.* 18:229–234.

37. Horowitz, M., et al. 1989. Gastric and oesophageal emptying in patients with type 2 (non-insulin-dependent) diabetes mellitus. *Diabetologia.* 32:151–159.

38. Kong, M. F., Macdonald, I. A., and Tattersall, R. B. 1996. Gastride emptying in diabetes. *Diabet. Med.* 13:112–119.

39. Delovitch, T. L., and Singh, B. 1997. The nonobese diabetic mouse as a model of autoimmune diabetes: immune dysregulation gets the NOD. *Immunity.* 7:727–738.

40. Jones, K. L., et al. 1999. The effect of erythromycin on gastric emptying is modified by physiological changes in the blood glucose concentration. *Am. J. Gastroenterol.* 94:2074–2079.

41. MacGregor, I. L., Gueller, R., Watts, H. D., and Meyer, J. H. 1976. The effect of acute hyperglycemia on gastric emptying in man. *Gastroenterology.* 70:190–196.

42. Schvarcz, E., et al. 1997. Physiological hyperglycemia slows gastric emptying in normal subjects and patients with insulin-dependent diabetes mellitus. *Gastroenterology.* 113:60–66.

43. Samsom, M., et al. 1997. Gastrointestinal motor mechanism in hyperglycaemia induced delayed gastric emptying in type I diabetes mellitus. *Gut.* 40:641–646.

44. Hebbard, G. S., Samsom, M., Sun, W. M., Dent, J., and Horowitz, M. 1996. Hyperglycemia affects proximal gastric motor and sensory function during small intestinal triglyceride infusion. *Am. J. Physiol.* 271:G814-G819.

45. Fraser, R., Horowitz, M., and Dent, J. 1991. Hyperglycaemia stimulates pyloric motility in normal subjects. *Gut.* 32:475–478.

46. Fraser, R. J., et al. 1990. Hyperglycaemia slows gastric emptying in type 1 (insulin-dependent) diabetes mellitus. *Diabetologia.* 33:675–680.

47. Fraser, R., Horowitz, M. Maddox, A., and Dent, J. 1993. Organization of antral, pyloric and duodenal motility in patients with gastroparesis. *Journal of Gastrointestinal Motility.* 5:167–175.

48. Aimi, Y., et al. 1993. Histochemical localization of nitric oxide synthase in rate enteric nervous system. *Neuroscience.* 53:553–560.

49. Costa, M., et al. 1992. Projections and chemical coding of neurons with immunotreactivity for nitric oxide synthase in the guinea-pig small intestine. *Neurosci. Lett.* 148:121–125.

50. Berezin, I., Snyder, S. H., Bredt, D. S., and Daniel, E. E. 1994. Ultrastructural localization of nitric oxide synthase in canine small intestine and colon. *Am. J. Physiol.* 266:C981–C989.

51. Corbin, J. D., and Francis, S. H. 1999. Cyclic GMP phosphodiesterase-5: target of sildenafil. *J. Biol. Chem.* 274:13729–13732.

52. Goldstein, I., et al. 1998. Oral sildenafil in the treatment of erectile dysfunction. Sildenafil Study Group. *N. Engl. J Med.* 338:1397–1404.

53. Kotera, J., et al. 1989. Novel alternative splice variants of cGMP-binding cGMP-specific phosphodiesterase. *J. Biol. Chem.* 273:26982–26990.

54. Lipp, R. W., et al. 1997. Evidence of accelerated gastric emptying in long-standing diabetic patients after ingestion of a semisolid meal. *J. Nucl. Med.* 38:814–818.

55. Phillips, W. T., Schwartz, J. G., and McMahan, C. A. 1992. Rapid gastric emptying of an oral glucose solution in type 2 diabetic patients. *J. Nucl. Med.* 33:1496–1500.

56. Zhang, X., et al. 1993. Nitric oxide synthase-like immunoreactivity in lumbar dorsal root ganglia and spinal cord of rat and monkey and effect of peripheral axotomy. *J. Comp. Nurol.* 335:563–575.

57. Wu, W., et al. 1994. Neuronol nitric oxide synthase is induced in spinal neurons by traumatic injury. *Neuroscience.* 61:719–726.

58. Yamamoto, R., Bredt, D. S., Dawson, T. M., Snyder, S. H., and Stone, R. A. 1993. Enhanced expression of nitric oxide synthase by rat retina following pterygopalatine parasympathetic denervation. *Brain Res.* 631:83–88.

59. Liu, M., Seino. S., and Kirchgessner, A. L. 1999. Identification and characterization of glucoresponsive neurons in the enteric nervous system. *J. Neurosci.* 19:10305–10317.

60. Brenman, J. E., Xia, H., Chao, D. S., Black, S. M., and Bredt, D. S. 1997. Regulation of neuronal nitric oxide synthase through alternative transcripts. *Dev. Neurosci.* 19:224–231.

61. Hall, A. V., et al. 1994. Structural organization of the human neuronal nitric oxide synthase gene (NOS 1). *J. Biol. Chem.* 269:33082–33090.

62. Wang, Y., and Marsden, P. A. 1995. Nitric oxide synthases: gene structure and regulation. *Adv. Pharmacol.* 34:71–90.

63. Wang, Y., et al. 1999. RNA diversity has profound effets on the translation of neuronal nitric oxide synthase. *Proc. Natl. Acad. Sci. USA.* 96:12150–12155.

64. Wang, Y., Newton, D. C., and Marsden, P. a. 1999. neuronal NOS: gene structure, mRNA diversity, and functional relevance. *Crit. Rev. Neurobiol.* 13:21–43.

65. Russo, A., Fraser, R., Adachi, K., Horowitz, M., and Boeckxstaens, G. 1999. Evidence that nitric oxide mechanisms regulate small intestinal motility in humans. *Gut.* 44:72–76.

66. Malcolm, A., and Camilleri, M. 1999. Assessment of gastrointestinal function. In *Diabetic neuropathy.* P. J. Dyck and P. K. Thomas, editors. W. B. Saunders Co. Philadelphia, Pa., USA. 211–221.

67. Pasricha, P. J., Huang, R. L. Rai, R. and Ferris, C. D. 1997. Achalasia and other motor disorders. In *Gastrointestinal disease: an endoscopic approach.* A. J. Dimarino and S. B. Benjamin, editors. Blackwell Science Inc. Malden, Mass., USA. 205–240.

68. DeGiorgio, R., et al. 1999. Esophageal and gastric nitric oxide synthesizing innervation in primary achalasia. *Am. J. Gastroenterol.* 94:2357–2362.

69. Mearin, F., et al. 1993. Patients with achalasia lack nitric oxide synthase in the gastro-oesophageal junction. *Eur. J. Clin. Invest.* 23:724–728.

70. Maxwell, P. R., Mendall, M. A., and Kumar, D. 1997. Irritable bowel syndrome. *Lancet.* 350:1691–1695.

71. Lynn, R. B., and Friedman, L. S. 1993. Irritable bowel syndrome. *N. Engl. J. Med.* 329:1940–1945.

72. Evans, P. R., Bak, Y. T., Shuter, B., Hoschl, R., and Kellow, J. E. 1997. Gastroparesis and small bowel dysmotility in irritable bowel syndrome. *Dig. Dis. Sci.* 42:2087–2093.

73. Pfaffenbach, B., Adamek, R. J. Bartholomaus, C., and Wegener, M. 1997. Gastric dysrhythmias and delayed gastric emptying in patients with functional dyspepsia. *Dig. Dis. Sci.* 42:2094–2099.

74. Bortolotti, M., Man, C., Lopilato, C., Porrazzo, G., and Miglioli, M. 2000. Effects of sildenafil on esophageal motility of patients with idiopathic achalasia. *Gastroenterology.* 118:253–257.

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method for treating a gastrointestinal disorder in a mammal suffering from the disorder, the method comprising administering to the mammal a therapeutically effective amount of sildenafil.

2. The method of claim 1, wherein the gastrointestinal disorder is characterized by motility disturbances in at least one of small intestine, colon and stomach.

3. The method of claim 1, wherein the disorder is characterized by diarrhea or constipation.

4. The method of claim 1, wherein the disorder is associated with diabetes.

5. A method for enhancing cGNP in a gastrointestinal organ comprising administering an effective amount of sildenafil to a mammal in need thereof.

6. The method of claim 5, wherein the mammal is a human.

7. The method of claim 5, wherein the organ is stomach, antrum, pylorus or intestine.

* * * * *